(12) United States Patent
Banner et al.

(10) Patent No.: US 8,729,061 B2
(45) Date of Patent: May 20, 2014

(54) PYRROLIDINE DERIVATIVES

(71) Applicant: Hoffmann-La Roche Inc., Nutley, NJ (US)

(72) Inventors: David Banner, Basel (CH); Wolfgang Haap, Loerrach (DE); Bernd Kuhn, Reinach BL (CH); Thomas Luebbers, Loerrach (DE); Jens-Uwe Peters, Grenzach-Wyhlen (DE); Tanja Schulz-Gasch, Ziefen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/681,470

(22) Filed: Nov. 20, 2012

(65) Prior Publication Data

US 2013/0137687 A1    May 30, 2013

(30) Foreign Application Priority Data

Nov. 25, 2011   (EP) .................................... 11190756

(51) Int. Cl.
*A01N 57/00* (2006.01)
*A61K 31/675* (2006.01)
*A61K 31/66* (2006.01)
*A01N 43/00* (2006.01)
*A61K 31/33* (2006.01)

(52) U.S. Cl.
USPC .............. 514/183; 514/79; 514/127; 514/128

(58) Field of Classification Search
None
See application file for complete search history.

(56) References Cited

U.S. PATENT DOCUMENTS

2010/0267722 A1   10/2010   Sanchez et al.

FOREIGN PATENT DOCUMENTS

WO   2007/137080   11/2007
WO   2009/100225   8/2009

OTHER PUBLICATIONS

Burns-Kurtis et al., "Cardiovascular Research" 62(3):610-620 (2004).
Wang et al., "J. Biol. Chem." 281(9):6020-6029 (2006).
Burden et al., "Clin. Cancer Res." 15(19):6042-6051 (2009).
Roberts, R., "Drug News & Perspectives" 18(10):605-614 (2005).
Shi et al., "Circulation Research" 92(5):493-500 (2003).
Hardegger et al., Angewandte Chemie International Edition 50(1):314-318 (2011).
International Search Report for PCT/EP2012/073073 dated Dec. 19, 2012.
Aikawa et al., "Circulation" 119(13):1785-1794 (2009).
Bromme, D., "Current Protocols in Protein Science" ((Suppl. 21)),:21.2.1-21.2.14 (2000).
Cheng et al., "American Journal of Pathology" 164(1):243-251 (2004).
Williams et al., "Pulmonary Pharmacology & Therapeutics" 22(1):27-32 (2009).

*Primary Examiner* — Craig Ricci
*Assistant Examiner* — Jared D Barsky

(57) ABSTRACT

The invention relates to a compound of formula (I)

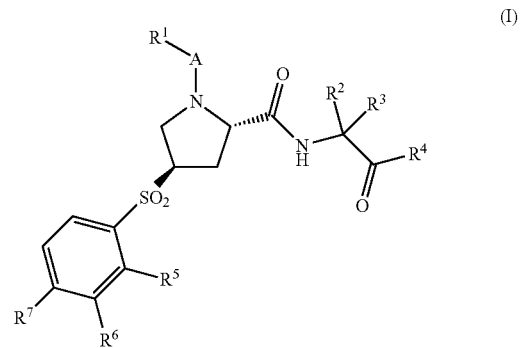

wherein A and $R^1$ to $R^7$ are defined as in the description and in the claims. The compound of formula (I) can be used as a medicament.

19 Claims, No Drawings

PYRROLIDINE DERIVATIVES

PRIORITY TO RELATED APPLICATION(S)

This application claims the benefit of European Patent Application No. 11190756.4, filed Nov. 25, 2011, which is hereby incorporated by reference in its entirety.

FIELD OF THE INVENTION

The present invention relates to organic compounds useful for therapy and/or prophylaxis in a mammal, and in particular to compounds that are preferential inhibitors of the cysteine protease cathepsin, in particular of the cysteine protease cathepsin S or L.

The compounds of the invention are preferential inhibitors of the cysteine protease Cathepsin (Cat), in particular Cathepsin S or Cathepsin L and are therefore useful to treat metabolic diseases like diabetes, atherosclerosis, abdominal aortic aneurysm, peripheral arterial disease, cancer, reduction of cardiovascular events in chronic kidney disease, glomerulonephritis, age related macular degeneration, diabetic nephropathy and diabetic retinopathy. In addition, immune mediated diseases like rheumatoid arthritis, Crohn's disease, multiple sclerosis, sjorgen syndrome, lupus erythematosus, neuropathic pain, diabetes type I, asthma and allergy and skin related immune disease are suitable diseases to be treated with a cathepsin S inhibitor.

BACKGROUND OF THE INVENTION

Mammalian cathepsins are cysteine-type proteases involved in key steps of biological and pathological events. Cathepsins are considered tractable drug targets as it is feasible to inhibit enzymatic activity with small molecules and are therefore of interest to the pharmaceutical industry (Bromme, D. (2001), 'Papain-like cysteine proteases', Curr Protoc Protein Sci, Chapter 21, Unit 21 2; Roberts, R. (2005), 'Lysosomal cysteine proteases: structure, function and inhibition of cathepsins', Drug News Perspect, 18 (10), 605-14).

Cathepsin S is prominently expressed in antigen presenting cells like macrophages and dendritic cells and smooth muscle cells. (Hsing, L. C. and Rudensky, A. Y. (2005), 'The lysosomal cysteine proteases in MHC class II antigen presentation', Immunol Rev, 207, 229-41; Rudensky, A. and Beers, C. (2006), 'Lysosomal cysteine proteases and antigen presentation', Ernst Schering Res Found Workshop, (56), 81-95). While Cathepsin S is only weakly expressed in normal arterial tissue, strong upregulation is seen in atherosclerotic arteries (Liu, J., et al. (2006), 'Increased serum cathepsin S in patients with atherosclerosis and diabetes', Atherosclerosis, 186 (2), 411-9; Sukhova, G. K., et al. (1998), 'Expression of the elastolytic cathepsins S and K in human atheroma and regulation of their production in smooth muscle cells', J Clin Invest, 102 (3), 576-83).

Preclinical data suggest that the function of Cathepsin S is critical for atherosclerosis as Cathepsin S deficient mice have a reduced atherosclerosis-phenotype when tested in appropriate mouse models. In LDL-Rec deficient mice reduced lipid accumulation, elastin-fiber breakdown and chronic arterial inflammation is reported. In APO E deficient mice a significant reduction of acute plaque rupture events was reported. When chronic renal disease is introduced into CatS/In APO-E deficient mice a strong reduction of accelerated calcification is seen on top of the anti atherosclerotic activity in arteries and heart valves Aikawa, E., et al. (2009), 'Arterial and aortic valve calcification abolished by elastolytic cathepsin S deficiency in chronic renal disease', Circulation, 119 (13), 1785-94; de Nooijer, R., et al. (2009), 'Leukocyte cathepsin S is a potent regulator of both cell and matrix turnover in advanced atherosclerosis', Arterioscler Thromb Vasc Biol, 29 (2), 188-94; Rodgers, K. J., et al. (2006), 'Destabilizing role of cathepsin S in murine atherosclerotic plaques', Arterioscler Thromb Vasc Biol, 26 (4), 851-6; Sukhova et al. (2003), 'Deficiency of cathepsin S reduces atherosclerosis in LDL receptor-deficient mice', J Clin Invest, 111 (6), 897-906). This suggests a potential inhibitor of Cathepsin S would stabilize atherosclerotic plaque by reducing extracellular matrix breakdown, by reducing the proinflammatory state and by reducing accelerated calcification and subsequently its clinical manifestations.

These phenotypes described in atherosclerosis models are in agreement with known cellular functions of Cathepsin S. Firstly, Cathepsin S is involved in the degradation of extracellular matrix that stabilizes the plaque. In particular, Cathepsin S has potent elastinolytic activity and can exert this at neutral pH, a feature that distinguishes Cathepsin S from all other Cathepsins. Secondly, Cathepsin S is the major protease involved in antigen processing, in particular cleavage of the invariant chain in antigen presenting cells, resulting in reduced contribution of Tcells to the chronic inflammation of the atherosclerotic tissue. Elevated inflammation results in further oxidative and proteolytic tissue damage and subsequently plaque destabilization (Cheng, X. W., et al. (2004), 'Increased expression of elastolytic cysteine proteases, cathepsins S and K, in the neointima of balloon-injured rat carotid arteries', Am J Pathol, 164 (1), 243-51; Driessen, C., et al. (1999), 'Cathepsin S controls the trafficking and maturation of MHC class II molecules in dendritic cells', J Cell Biol, 147 (4), 775-90; Rudensky, A. and Beers, C. (2006), 'Lysosomal cysteine proteases and antigen presentation', Ernst Schering Res Found Workshop, (56), 81-95).

The anti-inflammatory and anti-elastinolytic properties of a Cat S inhibitor make it also a prominent target for chronic obstructive pulmonary disease (Williams, A. S., et al. (2009), 'Role of cathepsin S in ozone-induced airway hyper responsiveness and inflammation', Pulm Pharmacol Ther, 22 (1), 27-32). Furthermore due to its extracellular functions in matrix degradation, inhibition of cathepsin S will impact neointima formation and angiogenesis (Burns-Kurtis, C. L., et al. (2004), 'Cathepsin S expression is up-regulated following balloon angioplasty in the hypercholesterolemic rabbit', Cardiovasc Res, 62 (3), 610-20; Cheng, X. W., et al. (2004), 'Increased expression of elastolytic cysteine proteases, cathepsins S and K, in the neointima of balloon-injured rat carotid arteries', Am J Pathol, 164 (1), 243-51; Shi, G. P., et al. (2003), 'Deficiency of the cysteine protease cathepsin S impairs microvessel growth', Circ Res, 92 (5), 493-500; Wang, B., et al. (2006), 'Cathepsin S controls angiogenesis and tumor growth via matrix-derived angiogenic factors', J Biol Chem, 281 (9), 6020-9). An inhibitor of Cathepsin S might therefore be useful in several different disease settings.

Cathepsin S plays also a role in the reduction of tumor growth and tumor cell invasion as described by Roberta E. Burden in Clin Cancer Res 2009; 15(19). In addition, nephrectomized Cathepsin S knock out mice showed a significant reduction of arterial calcification when compared to nephrectomized wild type mice. This indicates that inhibition of Cathepsin S may have a beneficial effect on the reduction of cardiovascular events in chronic kidney disease patients (Elena Aikawa, Circulation, 2009, 1785-1794).

Cathepsin L shows a broader expression profile than cathepsin S and there are also data which suggest a role of cathepsin L in atherosclerosis, e.g. LDLrec & Cat L deficient mice show a reduced atherosclerotic phenotype (Kitamoto, S., et al. (2007), 'Cathepsin L deficiency reduces diet-induced atherosclerosis in low-density lipoprotein receptor-knockout mice', Circulation, 115 (15), 2065-75). In addition, Cat L was suggested to be involved in metabolic syndrome as it controls adipogenesis and peripheral glucose tolerance. In renal disease Cathepsin L is described to regulate podocyte function by proteolytically processing dynamin and thereby proteinuria (Sever, S., et al. (2007), 'Proteolytic processing of dynamin by cytoplasmic cathepsin L is a mechanism for proteinuric kidney disease', J Clin Invest, 117 (8), 2095-104).

Tissue remodeling, extracellular matrix degradation, the generation of active neuropeptides and roles in antigen presentation in thymic epithelial cells are cellular activities described for Cathepsin L (Funkelstein et al. 2008; Rudensky and Beers 2006).

SUMMARY OF THE INVENTION

The present invention relates to compounds according to formula (I),

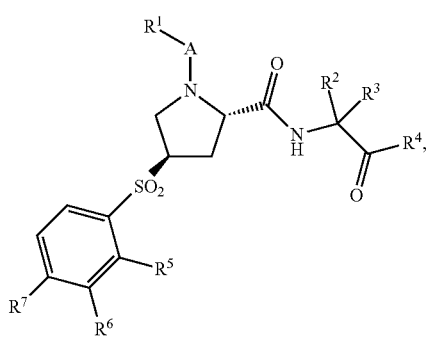

wherein
A is carbonyl or absent;
$R^1$ is selected from the group consisting of alkoxy, nitrophenyl, 1H-pyrazolyl substituted with alkyl and cycloalkyl, alkylcycloalkyl, haloalkylcycloalkyl, phenylcycloalkyl, halophenylcycloalkyl, pyridinylcycloalkyl and halopyridinylcycloalkyl;
$R^2$ and $R^3$ are independently selected from the group consisting of hydrogen, alkyl and cycloalkylalkyl;
or $R^2$ and $R^3$ together with the carbon atom to which they are attached form cycloalkyl;
$R^4$ is —C(O)$NR^8R^9$ or benzooxazolyl;
$R^5$, $R^6$ and $R^7$ are independently selected from the group consisting of hydrogen, alkyl, halogen, haloalkyl, alkoxy, haloalkoxy and morpholinyl; and
one of $R^8$ and $R^9$ is hydrogen or alkyl and the other one is selected from the group consisting of alkyl, alkoxyalkyl, cycloalkyl, haloalkyl, phenylalkyl, naphthylalkyl and tetrahydropyranyl.

The present invention relates also to pharmaceutically acceptable salts and esters of the aforementioned compounds.

DETAILED DESCRIPTION OF THE INVENTION

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls. Particular alkyls are methyl, ethyl, propyl, isopropyl and butyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, cyclobutyl, cyclopentyl, cyclohexyl, cycloheptyl and cyclooctyl. Particular cycloalkyl are cyclopropyl and cyclobutyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert. butoxy. Particular alkoxy are ethoxy, isopropoxy and tert. butoxy.

The term "oxy", alone or in combination, signifies the —O— group.

The term "halogen" or "halo", alone or in combination, signifies fluorine, chlorine, bromine or iodine.

The terms "haloalkyl", "halocycloalkyl", "haloalkoxy", "halophenyl", "halpyridinyl", alone or in combination, denote an alkyl group, a cycloalkyl group, an alkoxy group, a phenyl group and a pyridinyl group substituted with at least one halogen, preferably substituted with one to five halogens, preferably one to three halogens. A particular haloalkyl is trifluoromethyl. Particular haloalkoxy are trifluoroethyl and trifluoroisopropoxy.

The terms "hydroxyl" and "hydroxy", alone or in combination, signify the —OH group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivative at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wutts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The present invention relates in particular to a compound according to formula (I),

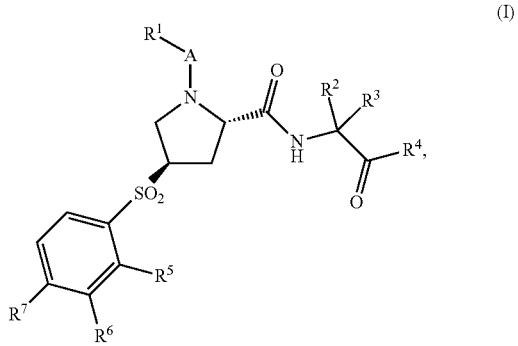

(I)

wherein
A is carbonyl or absent;
$R^1$ is selected from the group consisting of alkoxy, nitrophenyl, 1H-pyrazolyl substituted with alkyl and cycloalkyl, alkylcycloalkyl, haloalkylcycloalkyl, phenylcycloalkyl, halophenylcycloalkyl, pyridinylcycloalkyl and halopyridinylcycloalkyl;
$R^2$ and $R^3$ are independently selected from the group consisting of hydrogen, alkyl and cycloalkylalkyl;
or $R^2$ and $R^3$ together with the carbon atom to which they are attached form cycloalkyl;
$R^4$ is —C(O)NR$^8$R$^9$ or benzooxazolyl;
$R^5$, $R^6$ and $R^7$ are independently selected from the group consisting of hydrogen, alkyl, halogen, haloalkyl, alkoxy, haloalkoxy and morpholinyl; and
one of $R^8$ and $R^9$ is hydrogen or alkyl and the other one is selected from the group consisting of alkyl, alkoxyalkyl, cycloalkyl, haloalkyl, phenylalkyl, naphthylalkyl and tetrahydropyranyl;
or a pharmaceutically acceptable salt or ester thereof.

In an embodiment, the present invention relates to the compound of formula (I), wherein $R^1$ is halophenylcycloalkyl or halopyridinylcycloalkyl.

In an embodiment, the present invention relates to the compound of formula (I), wherein $R^1$ is selected from the group consisting of tert-butoxy, nitrophenyl, 1H-pyrazolyl substituted with methyl and cyclobutyl, trifluoromethycyclopropyl, phenylcycloalkyl, chlorophenylcyclopropyl, bromophenylcyclopropyl, iodophenylcyclopropyl, chlorofluorophenylcyclopropyl, bromofluorophenylcyclopropyl, pyridinylcycloalkyl or chlorofluoropyridinylcyclopropyl and bromofluoropyridinylcyclopropyl.

In an embodiment, the present invention relates to the compound of formula (I), wherein $R^1$ is selected from the group consisting of chlorophenylcyclopropyl, chlorofluorophenylcyclopropyl, bromophenylcyclopropyl, bromofluorophenylcyclopropyl and chlorofluoropyridinylcyclopropyl.

In an embodiment, the present invention relates to the compound of formula (I), wherein $R^2$ and $R^3$ are independently selected from hydrogen and alkyl.

In an embodiment, the present invention relates to the compound of formula (I), wherein $R^2$ and $R^3$ are independently selected from the group consisting of hydrogen, methyl, ethyl, propyl and butyl.

In an embodiment, the present invention relates to the compound of formula (I), wherein $R^5$, $R^6$ and $R^7$ are independently selected from the group consisting of halogen, haloalkyl and haloalkoxy.

In an embodiment, the present invention relates to the compound of formula (I), wherein $R^5$, $R^6$ and $R^7$ are independently selected from hydrogen, chloro, trifluoromethyl and trifluoroethoxy.

In an embodiment, the present invention relates to the compound of formula (I), wherein $R^5$ is selected from the group consisting of methyl, trifluoromethyl and chloro.

In an embodiment, the present invention relates to the compound of formula (I), wherein $R^5$ is chloro or trifluoromethyl.

In an embodiment, the present invention relates to the compound of formula (I), wherein $R^6$ is hydrogen.

In an embodiment, the present invention relates to the compound of formula (I), wherein $R^7$ is selected from the group consisting of hydrogen, methyl, chloro, fluoro, bromo, fluoro, trifluoroethoxy or trifluoropropoxy.

In an embodiment, the present invention relates to the compound of formula (I), wherein $R^7$ is selected from the group consisting of hydrogen, chloro and trifluoroethoxy.

In an embodiment, the present invention relates to the compound of formula (I), wherein one of $R^8$ and $R^9$ is hydrogen and the other one is alkyl or cycloalkyl.

In an embodiment, the present invention relates to the compound of formula (I), wherein one of $R^8$ and $R^9$ is hydrogen and the other one is selected from the group consisting of ethyl, propyl, butyl and cyclopropyl.

In an embodiment, the present invention relates to the compound of formula (I) selected from the group consisting of (2S,4R)-tert-butyl 2-((S)-1-(cyclopropylamino)-1,2-dioxopentan-3-ylcarbamoyl)-4-(2,4-dimethylphenylsulfonyl) pyrrolidine-1-carboxylate;

(2S,4R)-tert-butyl 4-(4-chloro-2-methylphenylsulfonyl)-2-((S)-1-(cyclopropylamino)-1,2-dioxopentan-3-ylcarbamoyl)pyrrolidine-1-carboxylate;

(2S,4R)—N—((S)-1-(cyclopropylamino)-1,2-dioxopentan-3-yl)-1-(2-nitrophenyl)-4-(2-(trifluoromethyl)phenylsulfonyl)pyrrolidine-2-carboxamide;

(2S,4R)-1-(1-cyclobutyl-3-methyl-1H-pyrazol-5-yl)-N—((S)-1-(cyclopropylamino)-1,2-dioxopentan-3-yl)-4-(4-fluoro-2-(trifluoromethyl)phenylsulfonyl)pyrrolidine-2-carboxamide;

(2S,4R)-1-(2-Nitro-phenyl)-4-(2-trifluoromethyl-benzenesulfonyl)-pyrrolidine-2-carboxylic acid [(S)-1-(benzooxazole-2-carbonyl)-propyl]-amide;

(2S,4R)-4-(4-bromo-2-(trifluoromethyl)phenylsulfonyl)-1-(1-cyclobutyl-3-methyl-1H-pyrazol-5-yl)-N—((S)-1-(cyclopropylamino)-1,2-dioxopentan-3-yl)pyrrolidine-2-carboxamide;

(2S,4R)—N—((S)-1-(cyclopropylamino)-1,2-dioxopentan-3-yl)-1-(1-(trifluoromethyl)cyclopropanecarbonyl)-4-(2-(trifluoromethyl)phenylsulfonyl)pyrrolidine-2-carboxamide;

(2S,4R)-1-(1-(4-chlorophenyl)cyclopropanecarbonyl)-4-(2-chlorophenylsulfonyl)-N—((S)-1-(cyclopropylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(cyclopropylamino)-1,2-dioxohexan-3-yl)pyrrolidine-2-carboxamide;

(2S,4R)-1-(1-(5-chloro-3-fluoropyridin-2-yl)cyclopropanecarbonyl)-4-(2-chloro-4-(2,2,2-trifluoroethoxy)phenylsulfonyl)-N—((S)-1-(cyclopropylamino)-1,2-dioxopentan-3-yl)pyrrolidine-2-carboxamide;

(2S,4R)-1-(1-(4-chlorophenyl)cyclopropanecarbonyl)-N—((S)-1-(cyclopropylamino)-1,2-dioxopentan-3-yl)-4-(4-(2,2,2-trifluoroethoxy)-2-(trifluoromethyl)phenylsulfonyl)pyrrolidine-2-carboxamide;

(2S,4R)—N—((S)-1-(benzo[d]oxazol-2-yl)-1-oxobutan-2-yl)-1-(1-(4-chlorophenyl)cyclopropanecarbonyl)-4-(2-chlorophenylsulfonyl)pyrrolidine-2-carboxamide;

(2S,4R)-1-(1-(4-chloro-2-fluorophenyl)cyclopropanecarbonyl)-4-(2-chlorophenylsulfonyl)-N—((S)-1-(cyclopropylamino)-1,2-dioxopentan-3-yl)pyrrolidine-2-carboxamide;

(2S,4R)-1-(1-(4-bromo-2-fluorophenyl)cyclopropanecarbonyl)-4-(2-chlorophenylsulfonyl)-N—((S)-1-(cyclopropylamino)-1,2-dioxopentan-3-yl)pyrrolidine-2-carboxamide;

(2S,4R)-1-(1-(4-bromophenyl)cyclopropanecarbonyl)-4-(2-chlorophenylsulfonyl)-N—((S)-1-(cyclopropylamino)-1,2-dioxopentan-3-yl)pyrrolidine-2-carboxamide;

(2S,4R)-1-(1-(4-bromophenyl)cyclopropanecarbonyl)-4-(2-chlorophenylsulfonyl)-N—((S)-1-(cyclopropylamino)-1,2-dioxohexan-3-yl)pyrrolidine-2-carboxamide;

(2S,4R)-4-(2-chlorophenylsulfonyl)-N—((S)-1-(cyclopropylamino)-1,2-dioxopentan-3-yl)-1-(1-(4-iodophenyl)cyclopropanecarbonyl)pyrrolidine-2-carboxamide;

(2S,4R)-4-(2-chlorophenylsulfonyl)-N—((S)-1-(cyclopropylamino)-1,2-dioxohexan-3-yl)-1-(1-(4-iodophenyl)cyclopropanecarbonyl)pyrrolidine-2-carboxamide;

(2S,4R)-1-(1-(5-chloro-3-fluoropyridin-2-yl)cyclopropanecarbonyl)-N—((S)-1-(cyclopropylamino)-1,2-dioxopentan-3-yl)-4-(2-(trifluoromethyl)phenylsulfonyl)pyrrolidine-2-carboxamide;

(2S,4R)-1-(1-(5-chloro-3-fluoropyridin-2-yl)cyclopropanecarbonyl)-N—((S)-1-(cyclopropylamino)-1,2-dioxohexan-3-yl)-4-(2-(trifluoromethyl)phenylsulfonyl)pyrrolidine-2-carboxamide;

(2S,4R)-1-(1-(4-chlorophenyl)cyclopropanecarbonyl)-N—((S)-1-(cyclopropylamino)-1,2-dioxopentan-3-yl)-4-(2-(trifluoromethyl)phenylsulfonyl)pyrrolidine-2-carboxamide;

(2S,4R)-1-(1-(4-chlorophenyl)cyclopropanecarbonyl)-N—((S)-1-(cyclopropylamino)-1,2-dioxohexan-3-yl)-4-(2-(trifluoromethyl)phenylsulfonyl)pyrrolidine-2-carboxamide;

(2S,4R)-1-(1-(5-bromo-3-fluoropyridin-2-yl)cyclopropanecarbonyl)-4-(2-chlorophenylsulfonyl)-N—((S)-1-(cyclopropylamino)-1,2-dioxopentan-3-yl)pyrrolidine-2-carboxamide;

(2S,4R)-1-(1-(5-chloro-3-fluoropyridin-2-yl)cyclopropanecarbonyl)-4-(2-chlorophenylsulfonyl)-N—((S)-1-(cyclopropylamino)-1,2-dioxohexan-3-yl)pyrrolidine-2-carboxamide;

(2S,4R)-1-(1-(5-chloro-3-fluoropyridin-2-yl)cyclopropanecarbonyl)-4-(2-chlorophenylsulfonyl)-N—((S)-1-(cyclopropylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N-(4-(cyclopropylamino)-2-methyl-3,4-dioxobutan-2-yl)pyrrolidine-2-carboxamide;

(2S,4R)-1-(1-(4-chlorophenyl)cyclopropanecarbonyl)-4-(2-chlorophenylsulfonyl)-N-(1-(2-(cyclopropylamino)-2-oxoacetyl)cyclopropyl)pyrrolidine-2-carboxamide;

(2S,4R)-1-(1-(4-chlorophenyl)cyclopropanecarbonyl)-4-(2-chlorophenylsulfonyl)-N—((S)-1-(cyclopropylamino)-4-methyl-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(cyclopropylamino)-5-methyl-1,2-dioxohexan-3-yl)pyrrolidine-2-carboxamide;

(2S,4R)-1-(1-(4-chlorophenyl)cyclopropanecarbonyl)-4-(2-chlorophenylsulfonyl)-N—((S)-1-cyclohexyl-4-(cyclopropylamino)-3,4-dioxobutan-2-yl)pyrrolidine-2-carboxamide;

(2S,4R)—N—((S)-1-(butylamino)-1,2-dioxopentan-3-yl)-1-(1-(4-chlorophenyl)cyclopropanecarbonyl)-4-(2-chlorophenylsulfonyl)pyrrolidine-2-carboxamide;

(2S,4R)—N—((S)-1-(butylamino)-1,2-dioxohexan-3-yl)-1-(1-(4-chlorophenyl)cyclopropanecarbonyl)-4-(2-chlorophenylsulfonyl)pyrrolidine-2-carboxamide;

(2S,4R)—N—((S)-1-(benzylamino)-1,2-dioxopentan-3-yl)-1-(1-(4-chlorophenyl)cyclopropanecarbonyl)-4-(2-chlorophenylsulfonyl)pyrrolidine-2-carboxamide;

(2S,4R)-1-(1-(4-chlorophenyl)cyclopropanecarbonyl)-4-(2-chlorophenylsulfonyl)-N—((S)-4-(cyclopropylamino)-3,4-dioxobutan-2-yl)pyrrolidine-2-carboxamide;

(2S,4R)—N—((S)-1-(benzylamino)-1,2-dioxohexan-3-yl)-1-(1-(4-chlorophenyl)cyclopropanecarbonyl)-4-(2-chlorophenylsulfonyl)pyrrolidine-2-carboxamide;

(2S,4R)-1-(1-(4-chlorophenyl)cyclopropanecarbonyl)-4-(2-chlorophenylsulfonyl)-N-((3S)-1,2-dioxo-1-(pentan-2-ylamino)pentan-3-yl)pyrrolidine-2-carboxamide;

(2S,4R)-1-(1-(4-chlorophenyl)cyclopropanecarbonyl)-4-(2-chlorophenylsulfonyl)-N-((3S)-1,2-dioxo-1-(pentan-2-ylamino)hexan-3-yl)pyrrolidine-2-carboxamide;

(2S,4R)-1-(1-(4-chlorophenyl)cyclopropanecarbonyl)-N—((S)-1-(cyclopropylamino)-1,2-dioxopentan-3-yl)-4-(2,4-dichlorophenylsulfonyl)pyrrolidine-2-carboxamide;

(2S,4R)-4-(2-chloro-4-fluorophenylsulfonyl)-1-(1-(4-chlorophenyl)cyclopropanecarbonyl)-N—((S)-1-(cyclopropylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1,2-dioxo-1-(2,2,2-trifluoroethylamino)hexan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(isopropylamino)-1,2-dioxohexan-3-yl)pyrrolidine-2-carboxamide;

(2S,4R)-1-(1-(4-chlorophenyl)cyclopropanecarbonyl)-N—((S)-1-(cyclopropylamino)-1,2-dioxohexan-3-yl)-4-(2,4-dichlorophenylsulfonyl)pyrrolidine-2-carboxamide;

(2S,4R)-1-(1-(4-chlorophenyl)cyclopropanecarbonyl)-4-(2-chlorophenylsulfonyl)-N—((S)-1-(ethylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(ethylamino)-1,2-dioxohexan-3-yl)pyrrolidine-2-carboxamide;

(2S,4R)-4-(2-chloro-4-((S)-1,1,1-trifluoropropan-2-yloxy)phenylsulfonyl)-1-(1-(4-chlorophenyl)cyclopropanecarbonyl)-N—((S)-1-(cyclopropylamino)-1,2-dioxopentan-3-yl)pyrrolidine-2-carboxamide;

(2S,4R)-4-(2-chloro-4-((S)-1,1,1-trifluoropropan-2-yloxy)phenylsulfonyl)-1-(1-(4-chlorophenyl)cyclopropanecarbonyl)-N—((S)-1-(cyclopropylamino)-1,2-dioxohexan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(cyclopropyl(methyl)amino)-1,2-dioxohexan-3-yl)pyrrolidine-2-carboxamide;

(2S,4R)-4-(2-chloro-4-fluorophenylsulfonyl)-1-(1-(4-chlorophenyl)cyclopropanecarbonyl)-N—((S)-1-(cyclopropylamino)-1,2-dioxohexan-3-yl)pyrrolidine-2-carboxamide;

(2S,4R)-1-(1-(4-chlorophenyl)cyclopropanecarbonyl)-4-(2-chlorophenylsulfonyl)-N—((S)-1,2-dioxo-1-(phenethylamino)pentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(2-(naphthalen-1-yl)ethylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(2-(naphthalen-2-yl)ethylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(naphthalen-1-ylmethylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1,2-dioxo-1-(tetrahydro-2H-pyran-4-ylamino)pentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(2-methoxyethylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(isobutylamino)-1,2-dioxopentan-3-yl)pyrrolidine-2-carboxamide;

(2S,4R)-4-(2-chloro-4-morpholinophenylsulfonyl)-1-(1-(4-chlorophenyl)cyclopropanecarbonyl)-N—((S)-1-(cyclopropylamino)-1,2-dioxopentan-3-yl)pyrrolidine-2-carboxamide;

(2S,4R)-4-(2-chloro-4-morpholinophenylsulfonyl)-1-(1-(4-chlorophenyl)cyclopropanecarbonyl)-N—((S)-1-(cyclopropylamino)-1,2-dioxohexan-3-yl)pyrrolidine-2-carboxamide;

(2S,4R)-1-(1-(5-chloro-3-fluoropyridin-2-yl)cyclopropanecarbonyl)-4-(2-chlorophenylsulfonyl)-N—((S)-1-(cyclopropylamino)-4-methyl-1,2-dioxopentan-3-yl)pyrrolidine-2-carboxamide;

(2S,4R)-1-(1-(5-chloro-3-fluoropyridin-2-yl)cyclopropanecarbonyl)-4-(2-chlorophenylsulfonyl)-N—((S)-1-(cyclopropylamino)-5-methyl-1,2-dioxohexan-3-yl)pyrrolidine-2-carboxamide;

(2S,4R)—N—((S)-1-(butylamino)-1,2-dioxopentan-3-yl)-1-(1-(5-chloro-3-fluoropyridin-2-yl)cyclopropanecarbonyl)-4-(2-chlorophenylsulfonyl)pyrrolidine-2-carboxamide;

(2S,4R)—N—((S)-1-(butylamino)-1,2-dioxohexan-3-yl)-1-(1-(5-chloro-3-fluoropyridin-2-yl)cyclopropanecarbonyl)-4-(2-chlorophenylsulfonyl)pyrrolidine-2-carboxamide; and (2S,4R)—N—((S)-1-(benzylamino)-1,2-dioxohexan-3-yl)-1-(1-(5-chloro-3-fluoropyridin-2-yl)cyclopropanecarbonyl)-4-(2-chlorophenylsulfonyl)pyrrolidine-2-carboxamide.

In an embodiment, the present invention relates to the compound of formula (I) selected from the group consisting of (2S,4R)-1-(1-(4-chlorophenyl)cyclopropanecarbonyl)-4-(2-chlorophenylsulfonyl)-N—((S)-1-(cyclopropylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(cyclopropylamino)-1,2-dioxohexan-3-yl)pyrrolidine-2-carboxamide;

(2S,4R)-1-(1-(5-chloro-3-fluoropyridin-2-yl)cyclopropanecarbonyl)-4-(2-chloro-4-(2,2,2-trifluoroethoxy)phenylsulfonyl)-N—((S)-1-(cyclopropylamino)-1,2-dioxopentan-3-yl)pyrrolidine-2-carboxamide;

(2S,4R)-1-(1-(4-chlorophenyl)cyclopropanecarbonyl)-N—((S)-1-(cyclopropylamino)-1,2-dioxopentan-3-yl)-4-(4-(2,2,2-trifluoroethoxy)-2-(trifluoromethyl)phenylsulfonyl)pyrrolidine-2-carboxamide;

(2S,4R)—N—((S)-1-(benzo[d]oxazol-2-yl)-1-oxobutan-2-yl)-1-(1-(4-chlorophenyl)cyclopropanecarbonyl)-4-(2-chlorophenylsulfonyl)pyrrolidine-2-carboxamide;

(2S,4R)-1-(1-(4-chloro-2-fluorophenyl)cyclopropanecarbonyl)-4-(2-chlorophenylsulfonyl)-N—((S)-1-(cyclopropylamino)-1,2-dioxopentan-3-yl)pyrrolidine-2-carboxamide;

(2S,4R)-1-(1-(5-chloro-3-fluoropyridin-2-yl)cyclopropanecarbonyl)-N—((S)-1-(cyclopropylamino)-1,2-dioxopentan-3-yl)-4-(2-(trifluoromethyl)phenylsulfonyl)pyrrolidine-2-carboxamide;

(2S,4R)-1-(1-(5-chloro-3-fluoropyridin-2-yl)cyclopropanecarbonyl)-N—((S)-1-(cyclopropylamino)-1,2-dioxohexan-3-yl)-4-(2-(trifluoromethyl)phenylsulfonyl)pyrrolidine-2-carboxamide;

(2S,4R)-1-(1-(4-chlorophenyl)cyclopropanecarbonyl)-N—((S)-1-(cyclopropylamino)-1,2-dioxopentan-3-yl)-4-(2-(trifluoromethyl)phenylsulfonyl)pyrrolidine-2-carboxamide;

(2S,4R)-1-(1-(4-chlorophenyl)cyclopropanecarbonyl)-N—((S)-1-(cyclopropylamino)-1,2-dioxohexan-3-yl)-4-(2-(trifluoromethyl)phenylsulfonyl)pyrrolidine-2-carboxamide;

(2S,4R)-1-(1-(5-chloro-3-fluoropyridin-2-yl)cyclopropanecarbonyl)-4-(2-chlorophenylsulfonyl)-N—((S)-1-(cyclopropylamino)-1,2-dioxohexan-3-yl)pyrrolidine-2-carboxamide;

(2S,4R)-1-(1-(5-chloro-3-fluoropyridin-2-yl)cyclopropanecarbonyl)-4-(2-chlorophenylsulfonyl)-N—((S)-1-(cyclopropylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(cyclopropylamino)-4-methyl-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(cyclopropylamino)-5-methyl-1,2-dioxohexan-3-yl)pyrrolidine-2-carboxamide;

(2S,4R)—N—((S)-1-(butylamino)-1,2-dioxopentan-3-yl)-1-(1-(4-chlorophenyl)cyclopropanecarbonyl)-4-(2-chlorophenylsulfonyl)pyrrolidine-2-carboxamide;

(2S,4R)-1-(1-(4-chlorophenyl)cyclopropanecarbonyl)-4-(2-chlorophenylsulfonyl)-N—((S)-4-(cyclopropylamino)-3,4-dioxobutan-2-yl)pyrrolidine-2-carboxamide;

(2S,4R)-1-(1-(4-chlorophenyl)cyclopropanecarbonyl)-N—((S)-1-(cyclopropylamino)-1,2-dioxopentan-3-yl)-4-(2,4-dichlorophenylsulfonyl)pyrrolidine-2-carboxamide;

(2S,4R)-1-(1-(4-chlorophenyl)cyclopropanecarbonyl)-4-(2-chlorophenylsulfonyl)-N—((S)-1-(isopropylamino)-1,2-dioxohexan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(ethylamino)-1,2-dioxopentan-3-yl)pyrrolidine-2-carboxamide; and (2S,4R)-1-(1-(4-chlorophenyl)cyclopropanecarbonyl)-4-(2-chlorophenylsulfonyl)-N—((S)-1-(ethylamino)-1,2-dioxohexan-3-yl)pyrrolidine-2-carboxamide.

The compounds of the present invention can be prepared, for example, by the general synthetic procedures described below.

In the following schemes and description, $R^1$ to $R^7$ and A have, unless otherwise indicated, the meaning of $R^1$ to $R^7$ and A as defined above.

ABBREVIATIONS

BOP: Benzotriazolyl-N-oxy-tris(dimethylamino)-phosphonium hexafluorophosphate;
BOP-Cl: Bis-(2-oxo-3-oxazolidinyl)-phosphinic acid chloride;
CDI: 1,1'-Carbonyldiimidazole;
DCC: N,N'-Dicyclohexylcarbodiimide;
DIPEA: Diisopropyl ethyl amine;
DMA: N,N-Dimethylacetamide;
DMF: N,N-Dimethylformamide;
EDCI: N-(3-Dimethylaminopropyl)-N'-ethyl-carbodiimide hydrochloride;
HATU: O-(7-azabenzotriazol-1-yl)-1,1,3,3-tetramethyluronium hexafluorophosphate;
HOBT: 1-Hydroxybenzotriazole;
LiHMDS: Lithium bis(trimethylsilyl)amide;
MCPBA: 3-Chloroperbenzoic acid;
NMP=N-Methylpyrrolidinone;
PyBOP: Benzotriazol-1-yl-oxytripyrrolidinephosphonium hexafluorophosphate;
TEA: Triethylamine;
TBTU: 0-(Benzotriazol-1-yl)-N,N,N',N'-tetramethyluronium terafluoroborate;
THF: Tetrahydrofurane;

The hydroxy function of an orthogonally protected cis-4-hydroxy-proline derivative A, such as (2S,4S)-4-hydroxy-pyrrolidine-1,2-dicarboxylic acid 1-tert-butyl ester 2-methyl ester, is transformed into an appropriate leaving group, e.g., by reaction with a sulfonyl chloride in the presence of a base such as triethylamine, to yield compound B (scheme 1). Reaction of B with thiophenols in the presence of an appropriate base such as NaH, LiHMDS, DIPEA, TEA, etc. yields compounds of type C. Oxidation of the obtained thioether is accomplished by an appropriate oxidizing agent such as $H_2O_2$, Oxone, MCPBA, etc. to yield sulfones D. Deprotection under appropriate conditions, depending on the nature of the protection group PG, gives E. E can be transformed into F by a large variety of conditions, which depend on the nature of the substituent $R^1$-A-, and which will be known to a person skilled in the art. For instance, if $R^1$-A- is an arylalkylcarbonyl substituent, the transformation can be accomplished by a reaction of E with the appropriate carboxylic acid, activated by one of the various coupling reagents such as BOP-Cl, TBTU, BOP, PyBop, HATU, EDCI/HOBT, DIC/HOBT; DCC/HOBT, etc. Saponification with a base such as LiOH, NaOH, KOH or $K_2CO_3$, $Na_2CO_3$, $Cs_2CO_3$, yields compounds G. Amide coupling of G with "warhead predecessors" O or Y is accomplished by one of the various coupling reagents such as BOP-Cl, TBTU, BOP, PyBop, HATU, EDCI/HOBT, DIC/HOBT; DCC/HOBT, etc. to give H. Oxidation of H by an oxidizing agent such as Dess-Martin Periodinane gives the final product I. It will be appreciated by the person skilled in the art that, at different stages of the reaction sequence, groups $R^5$, $R^6$, and $R^7$ can be transformed. For instance, a halogen can be transformed into an alkoxy substituent by the reaction with the appropriate alcohol in the presence of a base, such as $Cs_2CO_3$.

Scheme 1

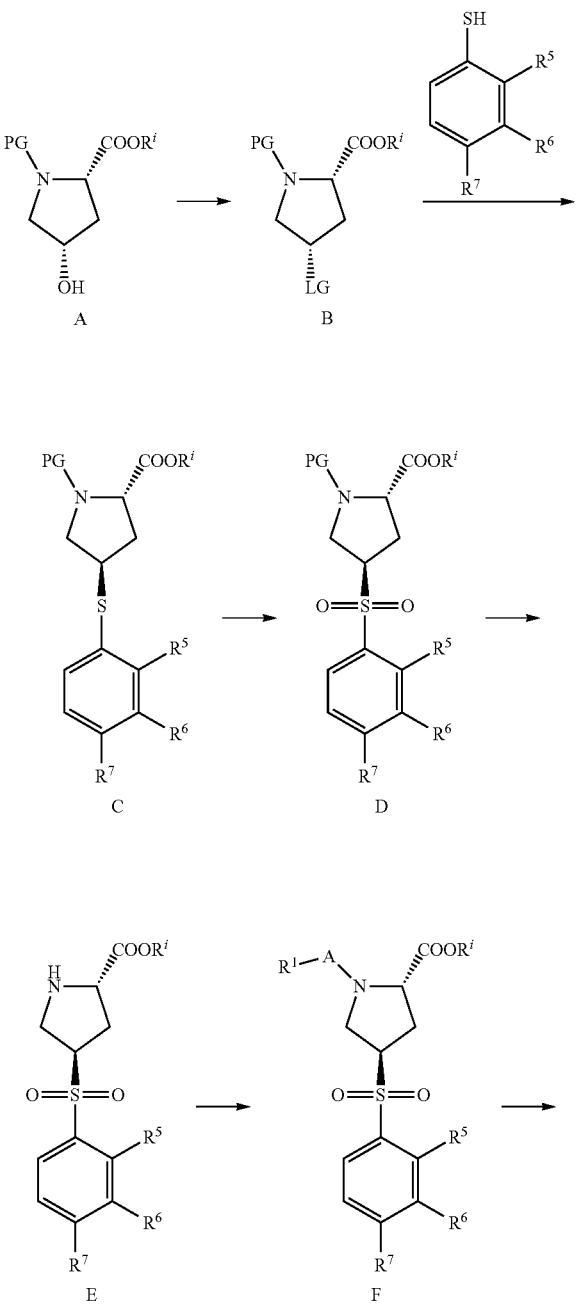

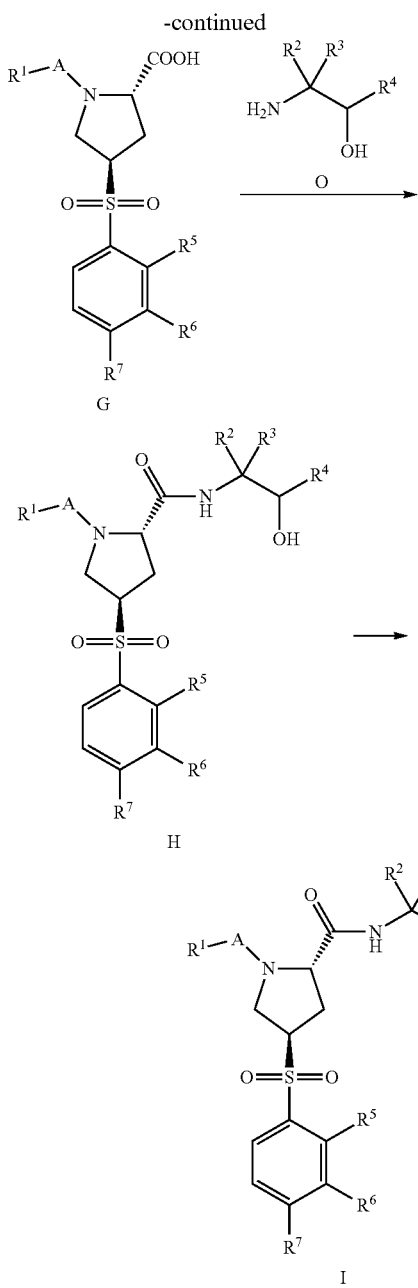

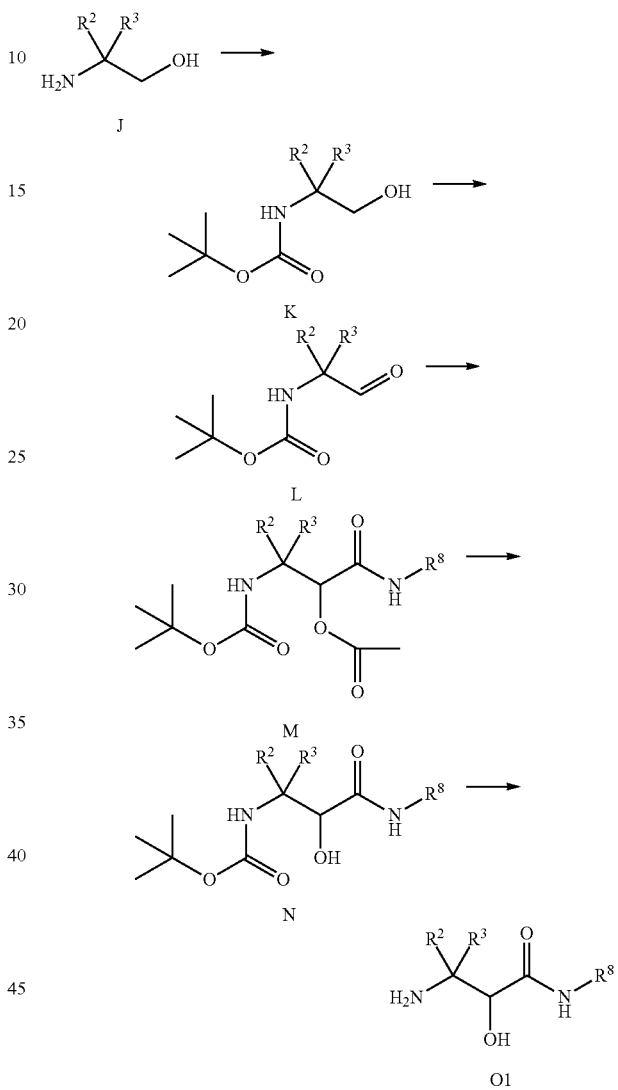

PG = protecting group, e.g., Boc, Cbz, Fmoc
LG = leaving group, e.g. —OSO₂R

The "warhead predecessors" O can be prepared by a variety of conditions, which may be exemplified by the general synthetic procedures below, named here the "Boc-Passerini-Route" (scheme 2), and the "Bn-amide-coupling route" (scheme 3). The person skilled in the art will appreciate that compounds O can also be prepared by variations of these procedures, in particular by procedures involving alternative protection groups.

A 2-aminoalkanol J is transformed into the corresponding tert-butyl carbamate, e.g. by reaction with di-tert-butyl dicarbonate in the presence of a base. Oxidation under suitable conditions, such as Swern's conditions, gives aldehyde L. Reaction with an isocyanide and acetic acid gives, in a transformation known as Passerini reaction, compound M. Saponification by a base such as NaOH gives compound N, which is finally transformed by Boc-deprotection under acidic conditions (e.g., trifluoroacetic acid), into the "warhead predecessor" O1.

Alternatively, "warhead predecessor" O may be prepared as outlined in scheme 3 ("Bn-amide-coupling route").

The reaction of an amino acid P with an excess of benzyl halide in the presence of a base gives compound Q, which can be saponified by a base, such as LiOH, NaOH, KOH or $K_2CO_3$, $Na_2CO_3$, $Cs_2CO_3$, to compound R. The carboxylic acid function of R is then reduced to an aldehyde, as in compound T. This can be accomplished by several ways, for instance, by transformation of R into a "Weinreb Amide" S and subsequent reaction with a suitable reducing agent, such as $LiAlH_4$ to give T. Reaction with a bisulfite salt, such as sodium bisulfite, and a cyanide salt, such as potassium cyanide, gives rise to a 2-hydroxynitrile U. Compound U can be saponified under acidic conditions to carboxylic acid V. Acid V is then coupled with a primary or secondary amine to give amide W, using one of the various coupling reagents such as BOP-Cl, TBTU, BOP, PyBop, HATU, EDCI/HOBT, DIC/

HOBT; DCC/HOBT, etc. In a final step, the compound is deprotected by hydrogenolysis under appropriate conditions to give "warhead predecessor" O2, e.g. by reaction with hydrogen under elevated pressure in the presence of a catalyst such as Pearlman's catalyst.

The preparation of benzoxazole-containing "warhead predecessors" can be accomplished as outlined in scheme 4. A suitably N-protected amino-aldehyde M is reacted with a carbanion equivalent of benzoxazole, which may in turn be prepared by reaction of benzoxazole with a metallating agent, such as isopropylmagnesium chloride. The resulting N-protected aminoalcohol X is then deprotected under the appropriate conditions to give "warhead predecessor" O3.

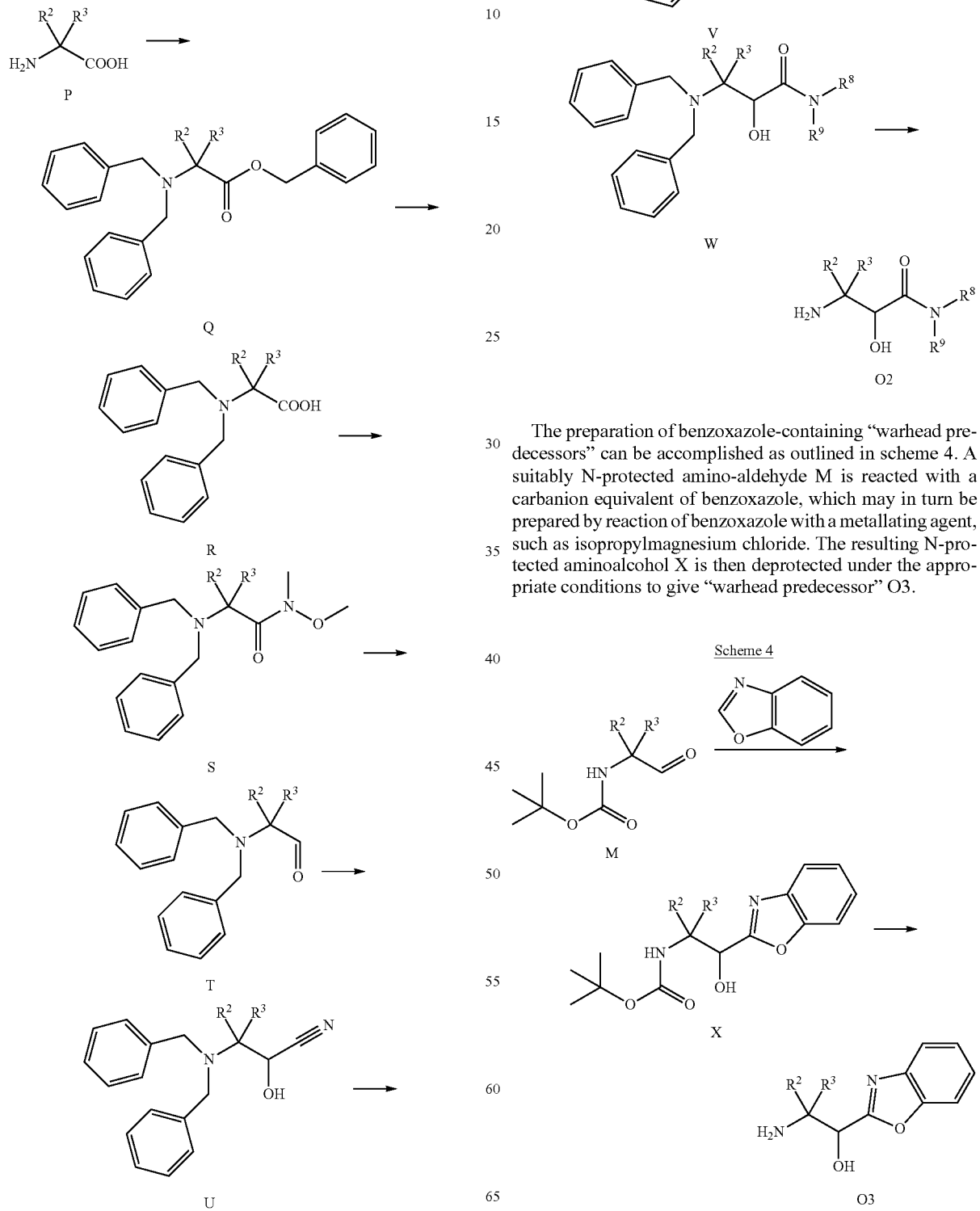

The invention also relates to a process for the preparation of a compound of formula (I) as define above, comprising the reaction of a compound of formula (II)

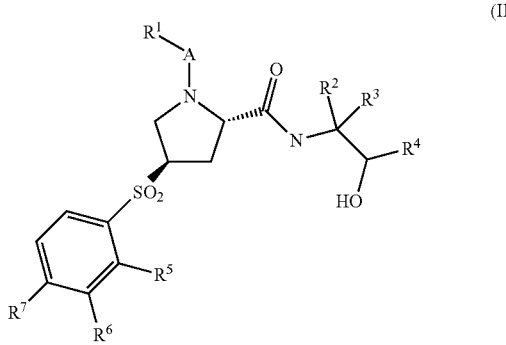

in the presence of an oxidant, wherein A and $R^1$ to $R^7$ are as defined above.

Suitable oxidants are known to those skilled in the art. In particular, the process of the invention can be carried out in the presence of Dess-Martin Periodinane, $CrO_3$, PDC (pyridinium dichromate), $O_2/V_2O_5$, $NaIO_4$, NaOCl/2,2,6,6-tetramethylpiperidine-1-oxyl or IBX (2-iodoxybenzoic acid).

The above process can be performed at a temperature of −20° C. to 150° C.

Suitable solvents for the process of the invention are dichloromethane, pyridine, toluene, DMSO, acetone, water or acetic acid.

A compound of formula (I), when manufactured according to the above process is also an object of the invention.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The invention thus also relates in particular to the following:

A compound of formula (I) for use as therapeutically active substance;

A pharmaceutical composition comprising a compound of formula (I) and a therapeutically inert carrier;

The use of a compound of formula (I) for the preparation of medicaments for the treatment or prophylaxis of diabetes, atherosclerosis, abdominal aortic aneurysm, peripheral arterial disease, cancer, reduction of cardiovascular events in chronic kidney disease, diabetic nephropathy, diabetic retinopathy or age related macular degeneration;

A compound of formula (I) for the treatment or prophylaxis of diabetes, atherosclerosis, abdominal aortic aneurysm, peripheral arterial disease, cancer, reduction of cardiovascular events in chronic kidney disease, diabetic nephropathy, diabetic retinopathy or age related macular degeneration; and A method for the treatment or prophylaxis of diabetes, atherosclerosis, abdominal aortic aneurysm, peripheral arterial disease, cancer, reduction of cardiovascular events in chronic kidney disease, diabetic nephropathy, diabetic retinopathy or age related macular degeneration, which method comprises administering an effective amount of a compound of formula (I).

The invention will now be illustrated by the following examples which have no limiting character.

EXAMPLES

Abbreviations

DIPEA: Diisopropyl ethyl amine;
DMF: N,N-Dimethylformamide;
EDC: N-(3-Dimethylaminopropyl)-N'-ethyl-carbodiimide hydrochloride;
Eq: equivalent(s)
HATU: O-(7-azabenzotriazol-1-yl)-1,1,3,3-tetramethyluronium hexafluorophosphate;
HOBt: 1-Hydroxybenzotriazole;
LiHMDS: Lithium bis(trimethylsilyl)amide;
MCPBA: 3-Chloroperbenzoic acid;
Satd.: saturated
RT: room temperature;
TBTU: O-(Benzotriazol-1-yl)-N,N,N',N'-tetramethyluronium terafluoroborate;
THF: Tetrahydrofurane;
TFA: Trifluoroacetic acid Synthesis of Intermediates Representative Procedure A ("Boc-Passerini-Route"): Synthesis of intermediate (2S,3S)-3-amino-N-cyclopropyl-2-hydroxypentanamide dihydrochloride Step A1:
(S)-tert-butyl-1-hydroxybutan-2-ylcarbamate Under an atmosphere of argon, (S)-2-aminobutan-1-ol (5.12 g, 56.3 mmol, Eq: 1.00) was combined with water (20 ml) and dioxane (20 ml) to give a colorless solution. At 0° C., NaOH (2.7 g, 67.5 mmol, Eq: 1.2) and di-tert-butyl dicarbonate (14.7 g, 67.5 mmol, Eq: 1.2) were added, and the reaction was stirred for 2 h at RT. The reaction mixture was poured into 50 ml $H_2O$ and extracted with EtOAc (2×75 ml). The organic layers were dried over Na₂SO₄ and concentrated in vacuo. The title compound was obtained as a colorless liquid (11.62 g, quant., MS (m/e)=190.3 [M+H⁺]).

Step A2: (S)-tert-butyl 1-oxobutan-2-ylcarbamate

Under an atmosphere of argon, oxalyl chloride (7.01 g, 4.75 ml, 55.3 mmol, Eq: 1.00) was combined with CH₂Cl₂ (100 ml) to give a colorless solution. The reaction was cooled to −60° C. Then dimethyl sulfoxide (10.8 g, 9.8 ml, 138 mmol, Eq: 2.5) diluted in CH₂Cl₂ (20 ml) was added dropwise at −60° C. The reaction was stirred for 10 min at −60° C. Then (S)-tert-butyl-1-hydroxybutan-2-ylcarbamate (11.62 g, 55.3 mmol, Eq: 1.00) dissolved in 20 ml CH₂Cl₂ was added dropwise at −70° C. The reaction was allowed to warm to −40° C. for 10 min and then cooled to −70° C. again. A solution of triethylamine (15.7 g, 21.6 ml, 155 mmol, Eq: 2.8) in 20 ml CH₂Cl₂ was added dropwise. The reaction mixture was allowed to warm to room temperature over 2 hours. The reaction mixture was poured into 100 ml satd. sodium dihydrogenphosphate solution and extracted with ethyl acetate (2×150 mL). The organic layer was back-extracted with brine (1×50 mL). The organic layers were dried over Na₂SO₄ and concentrated in vacuo. The title compound was obtained as a light yellow oil (11.12 g, quant., MS (m/e)=188.2 [M+H⁺]).

Step A3: (2S,3S)-3-(tert-butoxycarbonylamino)-1-(cyclopropylamino)-1-oxopentan-2-yl acetate Under an atmosphere of argon, (S)-tert-butyl-1-oxobutan-2-ylcarbamate (650 mg, 3.47 mmol, Eq: 1.00), isocyanocyclopropane (256 mg, 3.82 mmol, Eq: 1.1) and acetic acid (417 mg, 397 μl, 6.94 mmol, Eq: 2) were combined with CH₂Cl₂ (24.0 ml) to give a light yellow solution. The reaction was stirred overnight at RT. The solvents were removed under reduced pressure. The residue was purified by flash chromatography (silica gel, 20 g, 20% to 60% EtOAc in heptane). The title compound was obtained as a brown oil (1.09 g, quant., MS (m/e)=315.4 [M+H⁺]).

Step A4: tert-butyl (2S,3S)-1-(cyclopropylamino)-2-hydroxy-1-oxopentan-3-ylcarbamate Under an atmosphere of argon, (2S,3S)-3-(tert-butoxycarbonylamino)-1-(cyclopropylamino)-1-oxopentan-2-yl acetate (1.09 g, 3.47 mmol, Eq: 1.00) and NaOH 1N in H₂O (5.2 ml, 5.2 mmol, Eq: 1.5) were combined with methanol (10 ml) to give a colorless solution. The reaction was stirred for 2 h at RT. The reaction mixture was poured into 25 mL H₂O and extracted with ethyl acetate (2×50 mL). The organic layers were dried over Na₂SO₄ and concentrated in vacuo. The title compound was obtained as a light brown solid (540 mg, 57.2%, MS (m/e)=273.4 [M+H⁺]).

Step A5: (2S,3S)-3-amino-N-cyclopropyl-2-hydroxypentanamide dihydrochloride

Under an atmosphere of argon, tert-butyl (2S,3S)-1-(cyclopropylamino)-2-hydroxy-1-oxopentan-3-ylcarbamate (540 mg, 1.98 mmol) and HCl 4N in dioxane (10.4 ml) were combined to give a light brown solution. The reaction was stirred for 4 h at RT. The solvent was evaporated. The residual solvent was removed under vacuum. The title compound was obtained as a brown solid (480 mg, quant., MS (m/e)=173.2 [M+H⁺].

Representative procedure B ("Bn-amide-coupling route"): Synthesis of intermediate (2S,3S)-3-amino-N-cyclopropyl-2-hydroxypentanamide

Step B1: (S)-benzyl 2-(dibenzylamino)butanoate

Under an atmosphere of argon, sodium hydroxide (15.5 g, 388 mmol, Eq: 2) and potassium carbonate (53.6 g, 388 mmol, Eq: 2) were combined with water (300 ml) at 0° C. to give a colorless solution. (S)-2-Aminobutanoic acid (20 g, 194 mmol, Eq: 1.00) was added slowly between 0-5° C. The suspension was then heated to 90° C. Then benzyl bromide (133 g, 92.1 ml, 776 mmol, Eq: 4) was added dropwise. The reaction was stirred overnight at 90° C. The reaction mixture was poured into water (300 ml) and extracted with ethyl acetate. The organic layers were dried over Na₂SO₄ and concentrated in vacuo. The title compound was obtained as a light yellow liquid (84 g, 98.6%, MS (m/e)=374.3 [M+H⁺]).

Step B2: (S)-2-(dibenzylamino)butanoic acid

Under an atmosphere of argon, (S)-benzyl 2-(dibenzylamino)butanoate (84 g, 191 mmol, Eq: 1.00) was combined with methanol (136 ml) to give a light yellow solution. Then cold (0° C.) NaOH solution (15.3 g in 150 ml water, 382 mmol, Eq: 2) was added at once to the reaction mixture. The reaction was stirred at 90° C. for 4 h. Upon cooling to RT, the reaction mixture was poured into water (75 ml) and extracted with tert-butyl methyl ether: heptane=1:1 (2×150 ml), to remove the benzylalcohol formed in the hydrolysis. The basic aqueous layer was acidified to pH 2 with HCl (conc.). The aqueous layer was then extracted with ethyl acetate (2×250 ml). The organic layers were dried over Na₂SO₄, filtered and concentrated under reduced pressure. The residual solvent was removed under vacuum. The title compound was obtained as a white solid (68.13 g, quant., MS (m/e)=284.1 [M+H⁺], MS (m/e)=282.3 [M−H⁺]).

Step B3: (S)-2-(dibenzylamino)-N-methoxy-N-methylbutanamide

Under an atmosphere of argon, (S)-2-(dibenzylamino)butanoic acid (27 g, 80.0 mmol, Eq: 1.00) was combined with dichloromethane (250 ml) to give a white suspension. At 0° C., TBTU (36.0 g, 112 mmol, Eq: 1.4) was added. The reaction was stirred for 2 h at 0° C. Then N-methylmorpholine (24.3 g, 26.4 ml, 240 mmol, Eq: 3) and N,O-dimethylhydroxylamine hydrochloride (19.5 g, 200 mmol, Eq: 2.5) were added. The reaction was stirred overnight at RT. The reaction mixture was extracted with water (2×75 ml) and brine (50 ml). The organic layers were dried over Na₂SO₄ and concentrated in vacuo. The residual solvent was removed under vacuum. The title compound was obtained as a light yellow oil (35.5 g, 95.1%, MS (m/e)=327.3 [M+H⁺]).

Step B4: (S)-2-(dibenzylamino)butanal

Under an atmosphere of argon, at −20 to −30° C., LiAlH₄ (2.34 g, 61.8 mmol, Eq: 1.2) was combined with THF (150 ml) to give a light grey suspension. Then (S)-2-(dibenzylamino)-N-methoxy-N-methylbutanamide (24 g, 51.5 mmol, Eq: 1.00), diluted in THF (50 ml) was added at −30° C. The reaction was stirred for 2.5 h at −30° C. The excess reagent was quenched by the dropwise addition of ethyl acetate and water (1/1, ~30 ml). The reaction was vigorously stirred for 15 min at RT. After filtration through dicalite, the mixture was diluted with water (100 ml) and extracted with ethyl acetate.

The organic layers were dried over Na$_2$SO$_4$ and concentrated in vacuo. The title compound was obtained as a light brown liquid (13.41 g, 97.5%, MS (m/e)=268.3 [M+H$^+$]).

Step B5:
(2S,3S)-3-(dibenzylamino)-2-hydroxypentanenitrile

Under an atmosphere of argon, (S)-2-(dibenzylamino)butanal (8.55 g, 32.0 mmol, Eq: 1.00) was combined with dioxane (70 ml) to give a light yellow solution. The reaction was stirred for 10 min at 0° C. Then sodium bisulfite in water (40%, 26.5 ml) was added. The reaction was stirred for another 10 min at 0° C. Then potassium cyanide (8.33 g, 128 mmol, Eq: 4), diluted in water (35 ml) was added. The reaction was stirred overnight at RT. The reaction mixture was poured into water (75 ml) and extracted with ethyl acetate (2×75 ml). The organic layers were dried over Na$_2$SO$_4$ and concentrated in vacuo. The crude material was purified by flash chromatography (silica gel, 50 g, 0% to 40% ethyl acetate in heptane). The title compound was obtained as a light yellow oil (6.49 g, 68.9%, MS (m/e)=295.3 [M+H$^+$]).

Step B6:
(2S,3S)-3-(dibenzylamino)-2-hydroxypentanoic acid

Under an atmosphere of argon, (2S,3S)-3-(dibenzylamino)-2-hydroxypentanenitrile (7.05 g, 23.9 mmol, Eq: 1.00) and HCl (37%, 47.2 g, 39.3 ml, 479 mmol, Eq: 20) were combined to give a light brown solution. The reaction was stirred for 2.5 h at 100° C. The reaction was cooled with an ice bath and adjusted to pH 6 by addition of NaOH solution. The reaction was then extracted with dichloromethane and back-extracted with brine. The organic layers were dried over Na$_2$SO$_4$ and concentrated in vacuo. The residual solvent was removed under vacuum. The title compound was obtained as a brown foam (6.85 g, 91.3%, MS (m/e)=312.3 [M−H$^+$], MS (m/e)=314.0 [M+H$^+$]).

Step B7: (2S,3S)—N-cyclopropyl-3-(dibenzylamino)-2-hydroxypentanamide

Under an atmosphere of argon, (2S,3S)-3-(dibenzylamino)-2-hydroxypentanoic acid (5.85 g, 18.7 mmol, Eq: 1.00), cyclopropanamine (2.13 g, 2.62 ml, 37.3 mmol, Eq: 2) were combined with dichloromethane (100 ml) to give a light yellow solution. At 0° C. HOBt (4.29 g, 28.0 mmol, Eq: 1.5), EDC (5.37 g, 28.0 mmol, Eq: 1.5) and N-methylmorpholine (3.78 g, 4.1 ml, 37.3 mmol, Eq: 2) were added to the reaction. The reaction was stirred overnight at RT. The reaction mixture was poured into water (150 ml) and extracted with dichloromethane. The organic layer was back-extracted with water. The organic layers were dried over Na$_2$SO$_4$ and concentrated in vacuo. The crude material was purified by flash chromatography (silica gel, 70 g, 0% to 60% ethyl acetate in heptane). The title compound was obtained as a light brown crystalline (4.42 g, 67.2%, MS (m/e)=353.3 [M+H$^+$]).

Step B8:
(2S,3S)-3-amino-N-cyclopropyl-2-hydroxypentanamide (2S,3S)—N-Cyclopropyl-3-(dibenzylamino)-2-hydroxypentanamide (4.42 g, 12.5 mmol, Eq: 1.00) was hydrogenated with Pd(OH)$_2$ (20% on carbon, 890 mg, 1.27 mmol, Eq: 0.101) in methanol (50 ml) under a hydrogen pressure of 3.5 bar for 4 h. The catalyst was removed by filtration, and residual solvent was removed under vacuum. The title compound was obtained as a light yellow solid (2.09 g, 96.8%, MS (m/e)=173.2 [M+H$^+$]).

(2S,3S)-3-Amino-N-cyclopropyl-2-hydroxyhexanamide

The title compound was prepared in analogy to (2S,3S)-3-amino-N-cyclopropyl-2-hydroxypentanamide, Representative Procedure B, using (S)-2-aminopentanoic acid in the first step (step B1).

3-Amino-N-cyclopropyl-2-hydroxy-3-methylbutanamide

The title compound was prepared in analogy to (2S,3S)-3-amino-N-cyclopropyl-2-hydroxypentanamide dihydrochloride, Representative Procedure A, starting with tert-butyl 1-hydroxy-2-methylpropan-2-ylcarbamate in the second step (A2).

2-(1-Aminocyclopropyl)-N-cyclopropyl-2-hydroxyacetamide

The title compound was prepared in analogy to (2S,3S)-3-amino-N-cyclopropyl-2-hydroxypentanamide dihydrochloride, Representative Procedure A, starting with tert-butyl 1-formylcyclopropylcarbamate in the third step (A3).

(2S,3S)-3-Amino-N-cyclopropyl-2-hydroxy-4-methylpentanamide dihydrochloride

The title compound was prepared in analogy to (2S,3S)-3-amino-N-cyclopropyl-2-hydroxypentanamide dihydrochloride, Representative Procedure A, starting with (S)-2-amino-3-methylbutan-1-ol in the first step (A1).

(2S,3S)-3-Amino-N-cyclopropyl-2-hydroxy-5-methylhexanamide dihydrochloride

The title compound was prepared in analogy to (2S,3S)-3-amino-N-cyclopropyl-2-hydroxypentanamide dihydrochloride, Representative Procedure A, starting with (S)-2-amino-4-methylpentan-1-ol in the first step (A1).

(2S,3S)-3-Amino-4-cyclohexyl-N-cyclopropyl-2-hydroxybutanamide dihydrochloride

The title compound was prepared in analogy to (2S,3S)-3-amino-N-cyclopropyl-2-hydroxypentanamide dihydrochloride, Representative Procedure A, starting with (S)-tert-butyl 1-cyclohexyl-3-hydroxypropan-2-ylcarbamate in the second step (A2).

(2S,3S)-3-Amino-N-butyl-2-hydroxypentanamide dihydrochloride

The title compound was prepared in analogy to (2S,3S)-3-amino-N-cyclopropyl-2-hydroxypentanamide dihydrochloride, Representative Procedure A, using 1-isocyanobutane in the third step (A3).

(2S,3S)-3-Amino-N-butyl-2-hydroxyhexanamide dihydrochloride

The title compound was prepared in analogy to (2S,3S)-3-amino-N-cyclopropyl-2-hydroxypentanamide dihydrochloride, Representative Procedure A, using (S)-2-aminopentan-1-ol in the first step (A1), and 1-isocyanobutane in the third step (A3).

(2S,3S)-3-Amino-N-benzyl-2-hydroxypentanamide dihydrochloride

The title compound was prepared in analogy to (2S,3S)-3-amino-N-cyclopropyl-2-hydroxypentanamide dihydrochloride, Representative Procedure A, using (isocyanomethyl)benzene in the third step (A3).

(2S,3S)-3-Amino-N-cyclopropyl-2-hydroxybutanamide dihydrochloride

The title compound was prepared in analogy to (2S,3S)-3-amino-N-cyclopropyl-2-hydroxypentanamide dihydrochloride, Representative Procedure A, starting with (S)-tert-butyl 1-hydroxypropan-2-ylcarbamate in the second step (A2).

(2S,3S)-3-Amino-N-benzyl-2-hydroxyhexanamide dihydrochloride

The title compound was prepared in analogy to (2S,3S)-3-amino-N-cyclopropyl-2-hydroxypentanamide dihydrochloride, Representative Procedure A, starting with (S)-2-aminopentan-1-ol in the first step (A1), and using (isocyanomethyl)benzene in the third step (A3).

(2S,3S)-3-Amino-2-hydroxy-N-(pentan-2-yl)pentanamide dihydrochloride

The title compound was prepared in analogy to (2S,3S)-3-amino-N-cyclopropyl-2-hydroxypentanamide dihydrochloride, Representative Procedure A, using 2-isocyanopentane in the third step (A3).

(2S,3S)-3-Amino-2-hydroxy-N-(pentan-2-yl)hexanamide dihydrochloride

The title compound was prepared in analogy to (2S,3S)-3-amino-N-cyclopropyl-2-hydroxypentanamide dihydrochloride, Representative Procedure A, starting with (S)-2-aminopentan-1-ol in the first step (A1), and using 2-isocyanopentane in the third step (A3).

(2S,3S)-3-Amino-2-hydroxy-N-(2,2,2-trifluoroethyl)hexanamide

The title compound was prepared in analogy to (2S,3S)-3-amino-N-cyclopropyl-2-hydroxypentanamide, Representative Procedure B, using (S)-2-aminopentanoic acid in the first step (step B1), and 2,2,2-trifluoro-ethylamine in the seventh step (step B7).

(2S,3S)-3-Amino-2-hydroxy-N-isopropylhexanamide

The title compound was prepared in analogy to (2S,3S)-3-amino-N-cyclopropyl-2-hydroxypentanamide, Representative Procedure B, using (S)-2-aminopentanoic acid in the first step (step B1), and isopropylamine in the seventh step (step B7).

(2S,3S)-3-Amino-N-ethyl-2-hydroxypentanamide dihydrochloride

The title compound was prepared in analogy to (2S,3S)-3-amino-N-cyclopropyl-2-hydroxypentanamide dihydrochloride, Representative Procedure A, using isocyanoethane in the third step (A3).

(2S,3S)-3-Amino-N-ethyl-2-hydroxyhexanamide dihydrochloride

The title compound was prepared in analogy to (2S,3S)-3-amino-N-cyclopropyl-2-hydroxypentanamide dihydrochloride, Representative Procedure A, starting with (S)-2-aminopentan-1-ol in the first step (A1), and using isocyanoethane in the third step (A3).

(2S,3S)-3-Amino-N-cyclopropyl-2-hydroxy-N-methylhexanamide

The title compound was prepared in analogy to (2S,3S)-3-amino-N-cyclopropyl-2-hydroxypentanamide, Representative Procedure B, using (S)-2-aminopentanoic acid in the first step (step B1), and N-methylcyclopropanamine in the seventh step (step B7).

(2S,3S)-3-Amino-2-hydroxy-N-phenethylpentanamide

The title compound was prepared in analogy to (2S,3S)-3-amino-N-cyclopropyl-2-hydroxypentanamide, Representative Procedure B, using 2-phenylethanamine in the seventh step (step B7).

(2S,3S)-3-Amino-2-hydroxy-N-(2-(naphthalen-1-yl)ethyl)pentanamide

The title compound was prepared in analogy to (2S,3S)-3-amino-N-cyclopropyl-2-hydroxypentanamide, Representative Procedure B, using 2-(naphthalen-1-yl)ethanamine in the seventh step (step B7).

(2S,3S)-3-Amino-2-hydroxy-N-(2-(naphthalen-2-yl)ethyl)pentanamide

The title compound was prepared in analogy to (2S,3S)-3-amino-N-cyclopropyl-2-hydroxypentanamide, Representative Procedure B, using 2-(naphthalen-2-yl)ethanamine hydrochloride in the seventh step (step B7).

(2S,3S)-3-Amino-2-hydroxy-N-(naphthalen-1-ylmethyl)pentanamide

The title compound was prepared in analogy to (2S,3S)-3-amino-N-cyclopropyl-2-hydroxypentanamide, Representative Procedure B, using naphthalen-1-ylmethanamine in the seventh step (step B7).

Preparation of (2S)-2-amino-1-(benzo[d]oxazol-2-yl)butan-1-ol dihydrochloride, the "alpha-ketobenzoxazole predecessor" building block Step 1: tert-butyl (2S)-1-(benzo[d]oxazol-2-yl)-1-hydroxybutan-2-ylcarbamate Under an atmosphere of argon, benzo[d]oxazole (5 g, 42.0 mmol, Eq: 1.00) was combined with THF (100 ml) to give a light yellow solution. At −5° C. isopropylmagnesium chloride 2M in THF (21.0 ml, 42.0 mmol, Eq: 1.00) was added dropwise. The reaction was stirred for 1.5 h at −5° C. Then (S)-tert-butyl 1-oxobutan-2-ylcarbamate (4.72 g, 25.2 mmol, Eq: 0.6) diluted in 20 ml THF was added. The reaction was stirred overnight at RT. Satd. ammoniumchloride solution (6 ml) was added to the reaction. The THF was evaporated under vacuum. The reaction mixture was poured into 50 ml $H_2O$ and extracted with ethyl acetate (2×100 ml). The crude material was purified by flash chromatography (silica gel, 20 g, 0% to 40% ethyl acetate in heptane). The title compound was obtained as a brown gum (5.08 g, 39.5%, MS (m/e)=307.2 [M+H$^+$]).

Step 2: (2S)-2-amino-1-(benzo[d]oxazol-2-yl)butan-1-ol dihydrochloride

Under an atmosphere of argon, tert-butyl (2S)-1-(benzo[d]oxazol-2-yl)-1-hydroxybutan-2-ylcarbamate (800 mg, 2.61 mmol, Eq: 1.00) and HCl 4M in dioxane (17.3 ml) were combined to give a dark brown solution. The reaction was stirred for 2 h at RT. The crude reaction mixture was concentrated in vacuo, and the residual solvent was removed under vacuum. The title compound was obtained as a dark brown gum (910 mg, quant., MS (m/e)=207.1 [M+H$^+$]).

1-(5-Chloro-3-fluoropyridin-2-yl)cyclopropanecarboxylic acid

Step 1: 1-(5-chloro-3-fluoropyridin-2-yl)cyclopropanecarbonitrile

Under an atmosphere of argon, 5-chloro-2,3-difluoropyridine (6 g, 4.17 ml, 40.1 mmol, Eq: 1.00) was combined with toluene (60.0 ml). Then cyclopropanecarbonitrile (2.69 g, 3.02 ml, 40.1 mmol, Eq: 1.00) was added to the solution. At −5° C., potassium bis(trimethylsilyl)amide (80.3 ml, 40.1 mmol, Eq: 1.00) was added dropwise over 30 min. The dark brown reaction was stirred for 1 hour at −5° C., and then for 2 h at room temperature. The reaction mixture was poured into satd. NH$_4$Cl solution (50 ml) and extracted with 2×100 ml ethyl acetate. The organic layer was dried over Na$_2$SO$_4$, filtered and concentrated in vacuo. The crude material was purified by flash chromatography (70 g column, from 100% to 50% heptane in ethyl acetate). The title compound was obtained as a orange oil (1.55 g, 13.8%, MS (m/e)=197.2 [M+H$^+$].

Step 2: 1-(5-chloro-3-fluoropyridin-2-yl)cyclopropanecarboxylic acid

Under an atmosphere of argon, 1-(5-chloro-3-fluoropyridin-2-yl)cyclopropanecarbonitrile (1.55 g, 7.88 mmol, Eq: 1.00) was dissolved in KOH aq. (0.2 M, 43.4 ml, 8.67 mmol, Eq: 1.10). The reaction was stirred overnight at 100° C. The pH of the reaction mixture was adjusted to pH 6 by addition of HCl (1M). Then the reaction mixture was extracted with dichloromethane. The organic layer was dried over Na$_2$SO$_4$, filtered and concentrated in vacuo. The crude product was purified by flash chromatography (50 g column, from 50% to 100% ethyl acetate in heptane). The title compound was obtained as a orange solid (800 mg, 47.1%, MS (m/e)=216.3 [M+H$^+$]).

1-(5-Bromo-3-fluoropyridin-2-yl)cyclopropanecarboxylic acid

Step 1: 1-(5-bromo-3-fluoropyridin-2-yl)cyclopropanecarbonitrile

Under an atmosphere of argon, 5-bromo-2,3-difluoropyridine (5 g, 25.8 mmol, Eq: 1.00) and cyclopropanecarbonitrile (1.78 g, 2.00 ml, 25.8 mmol, Eq: 1.00) were combined with toluene (50.0 ml) to give a colorless solution. The reaction mixture was cooled to −5° C. Potassium bis(trimethylsilyl)amide (0.5 M, 51.6 ml, 25.8 mmol, Eq: 1.00) was added dropwise at −5° C. The reaction mixture was stirred 1 hr at −5° C., and over the weekend at RT. The reaction mixture was then poured into NH$_4$Cl solution (satd., 50 ml). The aqueous layer was extracted with ethyl acetate (3×60 ml). The organic layers were combined and dried over Na$_2$SO$_4$ and concentrated in vacuo. The crude material was purified by flash chromatography (silica gel, 70 g, 0% to 50% ethyl acetate in heptane as eluent) to yield the title compound as a light brown waxy solid (0.49 g, 7.89%, MS (m/e)=248.1 [M+H$^+$]).

Step 2: 1-(5-bromo-3-fluoropyridin-2-yl)cyclopropanecarboxylic acid

Under an atmosphere of argon, 1-(5-bromo-3-fluoropyridin-2-yl)cyclopropanecarbonitrile (0.49 g, 2.03 mmol, Eq: 1.00) was combined with KOH solution (1%, 12.5 ml) to give a light brown suspension. The reaction mixture was heated to 100° C. and stirred over night. Upon cooling to RT, HCl (1N, 3 ml) was added. The mixture was extracted with dichloromethane (3×15 ml). The organic layers were dried over Na$_2$SO$_4$ and concentrated in vacuo to yield the title compound as a light brown solid (0.420 g, 61.4%, MS (m/e)=260.1 [M+H$^+$]). The compound was used in the next steps with no further purification.

Representative Procedure C: (2S,4R)-1-(1-(4-chlorophenyl)cyclopropanecarbonyl)-4-(2-chlorophenylsulfonyl)pyrrolidine-2-carboxylic acid Step C1: (2S,4S)-1-tert-butyl 2-methyl 4-(3-nitrophenylsulfonyloxy)pyrrolidine-1,2-dicarboxylate Under an atmosphere of argon, (2S,4S)-1-tert-butyl 2-methyl 4-hydroxypyrrolidine-1,2-dicarboxylate (10 g, 39.5 mmol, Eq: 1.00) was combined with dichloromethane (75 ml) to give a colorless solution. Then at 0° C., 3-nitrobenzene-1-sulfonyl chloride (9.58 g, 41.9 mmol, Eq: 1.06) was added. Also at 0° C., triethylamine (12.0 g, 16.5 ml, 119 mmol, Eq: 3.00) was added dropwise to the reaction mixture. The reaction was stirred for 1.5 h at 0° C. and then for 2 days at room temperature. The reaction mixture was diluted in dichloromethane (200 ml) and then extracted with 2×50 ml HCl 0.5N, 70 ml satd. NaHCO$_3$ solution and 50 ml satd. NaCl solution. The organic layer was stirred over Na$_2$SO$_4$, filtered and concentrated under reduced pressure. The title compound was obtained as a brown gum (17.25 g, quant., MS (m/e)=431.3 [M+H$^+$]. The product was used in the next step without further purification.

Step C2: (2S,4R)-1-tert-butyl 2-methyl 4-(2-chlorophenylthio)pyrrolidine-1,2-dicarboxylate Under an atmosphere of argon, (2S,4S)-1-tert-butyl 2-methyl 4-(3-nitrophenylsulfonyloxy)pyrrolidine-1,2-dicarboxylate (8.5 g, 19.7 mmol, Eq: 1.00) was combined with propionitrile (82.0 ml) to give a light brown solution. Then 2-chlorobenzenethiol (4.28 g, 3.38 ml, 29.6 mmol, Eq: 1.50) and triethylamine (4.00 g, 5.5 ml, 39.5 mmol, Eq: 2.00) were added dropwise. The reaction was stirred overnight at reflux (100° C.). The reaction was cooled to room temperature, and poured in 50 ml Na$_2$CO$_3$ solution (10%), and extracted with 2×100 ml ethyl acetate. The organic layers were washed with 50 ml HCl 0.1M and 50 ml satd. NaCl solution. The organic layer was stirred over Na₂SO₄, filtered and concentrated in vacuo. The crude material was purified by flash chromatography (70 g column, from 100% to 80% heptane in ethyl acetate). The title compound was obtained as a yellow oil (5.7 g, 77.6%, MS (m/e)=372.1 [M+H⁺]).

Step C3: (2S,4R)-1-tert-butyl 2-methyl 4-(2-chlorophenylsulfonyl)pyrrolidine-1,2-dicarboxylate Under an atmosphere of argon, (2S,4R)-1-tert-butyl 2-methyl 4-(2-chlorophenylthio)pyrrolidine-1,2-dicarboxylate (5.7 g, 15.3 mmol, Eq: 1.00) was combined with dichloromethane (80.0 ml) to give a light yellow solution. At 0° C., 3-chlorobenzoperoxoic acid (7.21 g, 32.2 mmol, Eq: 2.10) was added slowly. The reaction was stirred overnight at room temperature. The reaction mixture was extracted with dichloromethane and washed with 80 ml satd. Na₂CO₃ solution and 50 ml brine. The organic layers were dried over Na₂SO₄, filtered and concentrated in vacuo. The crude material was purified by flash chromatography (70 g column, from 100% to 60% heptane in ethyl acetate). The title compound was obtained as a light yellow gum (5.76 g, 93.0%, MS (m/e)=404.3 [M+H⁺]).

Step C4: (2S,4R)-methyl 4-(2-chlorophenylsulfonyl)pyrrolidine-2-carboxylate

Under an atmosphere of argon, (2S,4R)-1-tert-butyl 2-methyl 4-(2-chlorophenylsulfonyl)pyrrolidine-1,2-dicarboxylate (5.76 g, 14.3 mmol, Eq: 1.00) was combined with dichloromethane (35.0 ml) to give a light yellow solution. At 0° C., 2,2,2-trifluoroacetic acid (24.4 g, 16.5 ml, 214 mmol, Eq: 15.0) was added dropwise. The reaction was warmed up to room temperature and stirred for 3 h. The reaction mixture was evaporated to dryness. The crude material was dissolved in 100 ml dichloromethane, then extracted with 50 ml satd. Na₂CO₃ solution and 50 ml H₂O. The aqueous layers were washed with 40 ml dichloromethane. The organic layer was dried over Na₂SO₄, filtered, and concentrated in vacuo. The title compound was obtained as a orange viscous oil (4.02 g, 92.8%, MS (m/e)=304.2 [M+H⁺]).

Step C5: (2S,4R)-methyl 1-(1-(4-chlorophenyl)cyclopropanecarbonyl)-4-(2-chlorophenylsulfonyl)pyrrolidine-2-carboxylate Under an atmosphere of argon, 1-(4-chlorophenyl)cyclopropanecarboxylic acid (1.57 g, 7.9 mmol, Eq: 1.20) was combined with tetrahydrofuran (70.0 ml) to give a colorless solution. Then EDC (3.09 g, 15.8 mmol, Eq: 2.40), HOBt (2.47 g, 15.8 mmol, Eq: 2.40) and triethylamine (6.66 g, 9.18 ml, 65.8 mmol, Eq: 10.0) was added. (A white suspension was obtained.) The reaction mixture was stirred for 15 min at room temperature. A solution of (2S,4R)-methyl 4-(2-chlorophenylsulfonyl)pyrrolidine-2-carboxylate (2 g, 6.58 mmol, Eq: 1.00) in tetrahydrofuran (14.0 ml) was added dropwise. The reaction was stirred for 3 days at room temperature. The reaction mixture was poured into 75 ml HCl 1M and extracted with 2×100 ml ethyl acetate. The organic layers were washed with 75 ml satd. Na₂CO₃ solution and 75 ml brine. The organic layer was dried over Na₂SO₄, filtered and concentrated in vacuo. The crude material was purified by flash chromatography (50 g column, from 0% to 100% ethyl acetate in heptane). The title compound was obtained as a light yellow solid (1.5 g, 47.2%, MS (m/e)=482.3 [M+H⁺]).

Step C6: (2S,4R)-1-(1-(4-chlorophenyl)cyclopropanecarbonyl)-4-(2-chlorophenylsulfonyl)pyrrolidine-2-carboxylic acid Under an atmosphere of argon, (2S,4R)-methyl 1-(1-(4-chlorophenyl)cyclopropanecarbonyl)-4-(2-chlorophenylsulfonyl)pyrrolidine-2-carboxylate (1.5 g, 3.11 mmol, Eq: 1.00) was combined with THF (20 ml) to give a light yellow solution. Then lithium hydroxide monohydrate (196 mg, 4.66 mmol, Eq: 1.5) in 4 ml water and 4 ml methanol was added. The reaction was stirred for 2 h at RT. The solvents were evaporated. The reaction was extracted with ethyl acetate, H₂O and brine. The organic layers were dried over Na₂SO₄ and concentrated in vacuo. The title compound was obtained as a white foam (1.52 g, 97.1%, MS (m/e)=468.2 [M+H⁺]; MS (m/e)=466.1 [M–H⁺]).

Preparation of (2S,4R)-1-(1-(trifluoromethyl)cyclopropanecarbonyl)-4-(2-(trifluoromethyl)phenylsulfonyl)pyrrolidine-2-carboxylic acid The title compound was prepared in analogy to Representative Procedure C, using 2-trifluoromethyl-benzenethiol in step C2 and 1-trifluoromethyl-cyclopropanecarboxylic acid/HATU in step C5.

Preparation of (2S,4R)-1-(1-(5-chloro-3-fluoropyridin-2-yl)cyclopropanecarbonyl)-4-(2-chloro-4-(2,2,2-trifluoroethoxy)phenylsulfonyl)pyrrolidine-2-carboxylic acid

Step 1: (2S,4R)-1-tert-butyl 2-methyl 4-(2-chloro-4-(2,2,2-trifluoroethoxy)phenylsulfonyl)pyrrolidine-1,2-dicarboxylate Under an atmosphere of argon, (2S,4R)-1-tert-butyl 2-methyl 4-(2-chloro-4-fluorophenylsulfonyl)pyrrolidine-1,2-dicarboxylate ([prepared in analogy to General Procedure C, steps C₁-C₃, using 2-chloro-4-fluorothiophenol in step C2] 1.5 g, 1.0 eq.) was combined with N,N-dimethylacetamide (15 ml) to give a light yellow solution. 2,2,2-Trifluoroethanol (854 mg, 617 µl, 8.53 mmol, Eq: 2.4) and cesium carbonate (2.09 g, 6.4 mmol, Eq: 1.8) were added. The reaction mixture was stirred over night at RT. The crude reaction mixture was concentrated in vacuo. The crude material was purified by flash chromatography (silica gel, 50 g, 0% to 50% ethyl acetate in heptane) to yield the title compound as a white foam (0.95 g, 53.2%, MS (m/e)=502.09 [M+H⁺]).

Step 2: (2S,4R)-1-(1-(5-chloro-3-fluoropyridin-2-yl)cyclopropanecarbonyl)-4-(2-chloro-4-(2,2,2-trifluoroethoxy)phenylsulfonyl)pyrrolidine-2-carboxylic acid The title compound was prepared in analogy to General Procedure C, steps C4-C6, using (2S,4R)-1-tert-butyl 2-methyl 4-(2-chloro-4-(2,2,2-trifluoroethoxy)phenylsulfonyl)pyrrolidine-1,2-dicarboxylate in step C4, and 1-(5-chloro-3-fluoro-pyridin-2-yl)-cyclopropanecarboxylic acid in step C5. MS (m/e)=584.9 [M+H⁺].

Preparation of (2S,4R)-1-[1-(4-chloro-phenyl)-cyclopropanecarbonyl]-4-[4-(2,2,2-trifluoro-ethoxy)-2-trifluoromethyl-benzenesulfonyl]-pyrrolidine-2-carboxylic acid

Step 1: (2S,4R)-1-tert-Butyl 2-methyl 4-(4-(2,2,2-trifluoroethoxy)-2-(trifluoromethyl)phenylsulfonyl)pyrrolidine-1,2-dicarboxylate Under an atmosphere of argon, (2S,4R)-1-tert-butyl 2-methyl 4-(4-fluoro-2-(trifluoromethyl)phenylsulfonyl)pyrrolidine-1,2-dicarboxylate ([prepared in analogy to General Procedure C, steps C1-C3, using 2-trifluoromethyl-4-fluorothiophenol in step C2] 0.79 g, 1.73 mmol, Eq: 1.00) was combined with N,N-dimethylacetamide (10 ml) to give a light yellow solution. 2,2,2-Trifluoroethanol (416 mg, 301 μl, 4.16 mmol, Eq: 2.4) and cesium carbonate (1.02 g, 3.12 mmol, Eq: 1.8) were added. The reaction mixture was stirred over night at RT. The crude reaction mixture was concentrated in vacuo. The residue was poured into HCl (0.5 M, 20 ml) and extracted with ethyl acetate. The organic layers were dried over $Na_2SO_4$ and concentrated in vacuo. The crude material was purified by flash chromatography (silica gel, 50 g, 0% to 40% ethyl acetate in heptane) to yield the title compound as a white foam (610 mg, 65.7%, MS (m/e)=536.1 $[M+H^+]$).

Step 2: (2S,4R)-1-(1-(4-Chlorophenyl)cyclopropanecarbonyl)-4-(4-(2,2,2-trifluoroethoxy)-2-(trifluoromethyl)phenylsulfonyl)pyrrolidine-2-carboxylic acid The title compound was prepared in analogy to General Procedure C, steps C4-C6, using (2S,4R)-1-tert-butyl 2-methyl 4-(4-(2,2,2-trifluoroethoxy)-2-(trifluoromethyl)phenylsulfonyl)pyrrolidine-1,2-dicarboxylate in step C4. MS (m/e)= 600.0 $[M+H^+]$.

Preparation of (2S,4R)-4-(2-chloro-benzenesulfonyl)-1-[1-(4-chloro-2-fluoro-phenyl)-cyclopropanecarbonyl]-pyrrolidine-2-carboxylic acid The title compound was prepared in analogy to Representative Procedure C, using 1-(4-chloro-2-fluoro-phenyl)-cyclopropanecarboxylic acid in step C5.

Preparation of (2S,4R)-1-[1-(4-bromo-2-fluoro-phenyl)-cyclopropanecarbonyl]-4-(2-chloro-benzenesulfonyl)-pyrrolidine-2-carboxylic acid The title compound was prepared in analogy to Representative Procedure C, using 1-(4-bromo-2-fluoro-phenyl)-cyclopropanecarboxylic acid in step C5.

Preparation of (2S,4R)-1-[1-(4-Bromo-phenyl)-cyclopropanecarbonyl]-4-(2-chloro-benzenesulfonyl)-pyrrolidine-2-carboxylic acid The title compound was prepared in analogy to Representative Procedure C, using 1-(4-bromo-phenyl)-cyclopropanecarboxylic acid in step C5.

Preparation of (2S,4R)-4-(2-chloro-benzenesulfonyl)-1-[1-(4-iodo-phenyl)-cyclopropanecarbonyl]-pyrrolidine-2-carboxylic acid The title compound was prepared in analogy to Representative Procedure C, using 1-(4-iodo-phenyl)-cyclopropanecarboxylic acid in step C5.

Preparation of (2S,4R)-1-[1-(5-chloro-3-fluoro-pyridin-2-yl)-cyclopropanecarbonyl]-4-(2-trifluoromethyl-benzenesulfonyl)-pyrrolidine-2-carboxylic acid The title compound was prepared in analogy to Representative Procedure C, using 1-(5-chloro-3-fluoropyridin-2-yl) cyclopropanecarboxylic acid in step C5 and 2-(trifluoromethyl)thiophenol in step C2.

Preparation of (2S,4R)-1-[1-(4-chloro-phenyl)-cyclopropanecarbonyl]-4-(2-trifluoromethyl-benzenesulfonyl)-pyrrolidine-2-carboxylic acid The title compound was prepared in analogy to Representative Procedure C, using 2-(trifluoromethyl)thiophenol in step C2.

Preparation of (2S,4R)-4-(2-chloro-benzenesulfonyl)-1-[1-(5-chloro-3-fluoro-pyridin-2-yl)-cyclopropanecarbonyl]-pyrrolidine-2-carboxylic acid The title compound was prepared in analogy to Representative Procedure C, using 1-(5-chloro-3-fluoropyridin-2-yl) cyclopropanecarboxylic acid in step C5.

Preparation of (2S,4R)-1-[1-(4-chloro-phenyl)-cyclopropanecarbonyl]-4-(2,4-dichloro-benzenesulfonyl)-pyrrolidine-2-carboxylic acid The title compound was prepared in analogy to Representative Procedure C, using 2,4-dichlorothiophenol in step C2.

Preparation of (2S,4R)-4-(2-chloro-4-fluoro-benzenesulfonyl)-1-[1-(4-chloro-phenyl)-cyclopropanecarbonyl]-pyrrolidine-2-carboxylic acid The title compound was prepared in analogy to Representative Procedure C, using 2-chloro-4-fluorothiophenol in step C2.

Preparation of (2S,4R)-1-[1-(4-chloro-phenyl)-cyclopropanecarbonyl]-4-[2-chloro-4-((S)-2,2,2-trifluoro-1-methyl-ethoxy)-benzenesulfonyl]-pyrrolidine-2-carboxylic acid Step 1: (2S,4R)-Methyl 4-(2-chloro-4-((S)-1,1,1-trifluoropropan-2-yloxy)phenylsulfonyl)-1-(1-(4-chlorophenyl)cyclopropanecarbonyl)pyrrolidine-2-carboxylate Under an atmosphere of argon, (2S,4R)-methyl 4-(2-chloro-4-fluorophenylsulfonyl)-1-(1-(4-chlorophenyl)cyclopropanecarbonyl)pyrrolidine-2-carboxylate (200 mg, 331 μmol, Eq: 1.00, [prepared in analogy to General Procedure C, steps C1-C5, using 2-chloro-4-fluorothiophenol in step C2]) and cesium carbonate (194 mg, 595 μmol, Eq: 1.8) were combined with N,N-dimethylacetamide (2 ml) to give a colorless solution. (R)-1,1,1-trifluoropropan-2-ol (90.5 mg, 793 μmol, Eq: 2.4) was added. The reaction mixture was stirred over night at rt. The crude reaction mixture was concentrated in vacuo. The residue was poured into HCl (0.5 M, 5 ml) and extracted with ethyl acetate (5×20 ml). The organic layers were dried over $Na_2SO_4$ and concentrated in vacuo. The crude material was purified by flash chromatography (silica gel, 50 g, 0% to 40% EtOAc in heptane) to yield the title compound as a white foam (178 mg, 67.1%, MS (m/e)=594.07 $[M+H^+]$)

Step 2: (2S,4R)-1-[1-(4-Chloro-phenyl)-cyclopropanecarbonyl]-4-[2-chloro-4-((S)-2,2,2-trifluoro-1-methyl-ethoxy)-benzenesulfonyl]-pyrrolidine-2-carboxylic acid The title compound was prepared in analogy to General Procedure C, step C6, using (2S,4R)-methyl 4-(2-chloro-4-

((S)-1,1,1-trifluoropropan-2-yloxy)phenylsulfonyl)-1-(1-(4-chlorophenyl)cyclopropanecarbonyl)pyrrolidine-2-carboxylate.

Example 1

(2S,4R)-tert-butyl 2-((S)-1-(cyclopropylamino)-1,2-dioxopentan-3-ylcarbamoyl)-4-(2,4-dimethylphenylsulfonyl)pyrrolidine-1-carboxylate

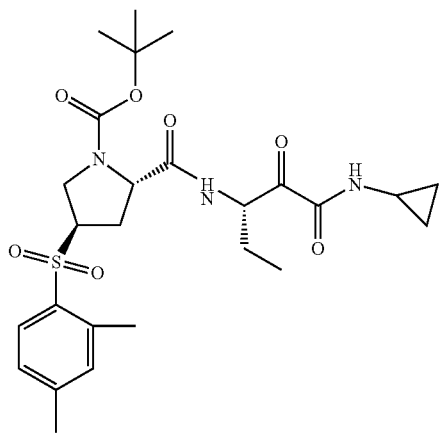 [SMILES: CC[C@H](NC(=O)[C@@H]1C[C@@H](S(=O)(=O)c2ccc(C)cc2C)CN1C(=O)OC(C)(C)C)C(=O)C(=O)NC1CC1]

Step 1 ("coupling"): (2S,4R)-tert-butyl 2-((2S,3S)-1-(cyclopropylamino)-2-hydroxy-1-oxopentan-3-ylcarbamoyl)-4-(2,4-dimethylphenylsulfonyl)pyrrolidine-1-carboxylate (2S,4R)-1-(tert-butoxycarbonyl)-4-(2,4-dimethylphenylsulfonyl)pyrrolidine-2-carboxylic acid (120 mg, 313 μmol, Eq: 1.00, prepared as described in U.S. Pat. Appl. US20100267722), (2S,3S)-3-amino-N-cyclopropyl-2-hydroxypentanamide dihydrochloride (99.7 mg, 407 μmol, Eq: 1.3), N,N-diisopropylethylamine (121 mg, 164 μA, 939 μmol, Eq: 3) and HATU (202 mg, 532 μmol, Eq: 1.7) were combined with DMF (2 ml) to give a light brown solution. The reaction was stirred overnight at RT. The crude material was purified by preparative HPLC (column: ymc C18 (120 A), 75×30 mm, acetonitrile/water (+0.1% formic acid)=95%-5% to 5%-95% in 8 min, flow: 25 ml/min). After evaporation of solvents, the title compound was obtained as a light brown foam (64.3 mg, 38.2%, MS (m/e)=538.3 [M+H$^+$]).

Step 2 ("oxidation"): (2S,4R)-tert-butyl 2-((S)-1-(cyclopropylamino)-1,2-dioxopentan-3-ylcarbamoyl)-4-(2,4-dimethylphenylsulfonyl)pyrrolidine-1-carboxylate (2S,4R)-tert-butyl 2-((2S,3S)-1-(cyclopropylamino)-2-hydroxy-1-oxopentan-3-ylcarbamoyl)-4-(2,4-dimethylphenylsulfonyl)pyrrolidine-1-carboxylate (64 mg, 119 μmol, Eq: 1.00) and Dess-Martin periodinane (572 mg, 202 μmol, Eq: 1.7) were combined with CH$_2$Cl$_2$ (1 ml). The reaction was stirred overnight at RT. Dess-Martin periodinane (280 mg) was added again and stirred for 5 h, until near complete conversion. The reaction was extracted with 15 ml CH$_2$Cl$_2$ and 2×5 ml satd. Na$_2$S$_2$O$_3$. The organic layers were dried over Na$_2$SO$_4$ and concentrated in vacuo. The crude material was purified by preparative HPLC. The title compound was obtained as a light yellow gum (52.5 mg, 82.3%, MS (m/e)=536.24 [M+H$^+$]).

Example 2

(2S,4R)-tert-butyl 4-(4-chloro-2-methylphenylsulfonyl)-2-((S)-1-(cyclopropylamino)-1,2-dioxopentan-3-ylcarbamoyl)pyrrolidine-1-carboxylate

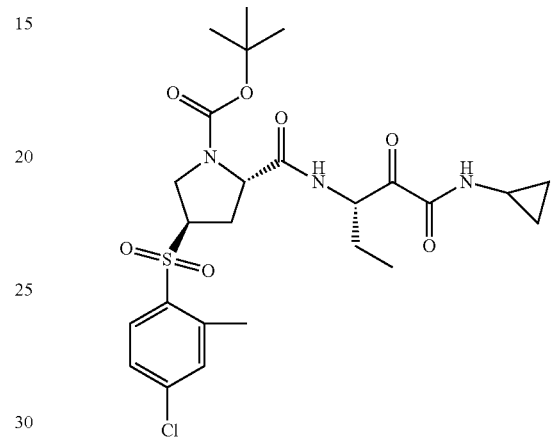

The title compound was prepared in analogy to Example 1, using (2S,4R)-1-(tert-butoxycarbonyl)-4-(4-chloro-2-methylphenylsulfonyl)pyrrolidine-2-carboxylic acid (prepared as described in U.S. Pat. Appl. US20100267722) in step 1. MS (m/e)=556.19 [M+H$^+$].

Example 3

(2S,4R)—N—((S)-1-(cyclopropylamino)-1,2-dioxopentan-3-yl)-1-(2-nitrophenyl)-4-(2-(trifluoromethyl)phenylsulfonyl)pyrrolidine-2-carboxamide

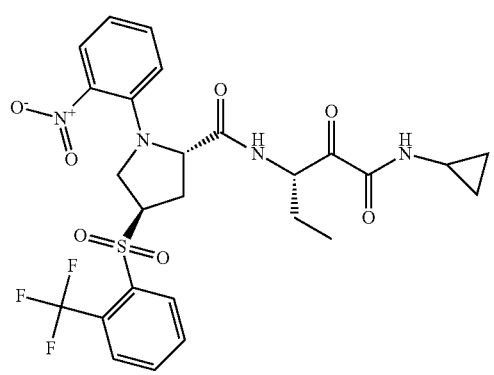 [SMILES: CC[C@H](NC(=O)[C@@H]1C[C@@H](S(=O)(=O)c2ccccc2C(F)(F)F)CN1c1ccccc1[N+](=O)[O-])C(=O)C(=O)NC1CC1]

The title compound was prepared in analogy to Example 1, using (2S,4R)-1-(2-nitrophenyl)-4-(2-(trifluoromethyl)phenylsulfonyl)pyrrolidine-2-carboxylic acid (prepared as described in U.S. Pat. Appl. US20100267722) in step 1. MS (m/e)=597.16 [M+H⁺].

Example 4

(2S,4R)-1-(1-cyclobutyl-3-methyl-1H-pyrazol-5-yl)-N—((S)-1-(cyclopropylamino)-1,2-dioxopentan-3-yl)-4-(4-fluoro-2-(trifluoromethyl)phenylsulfonyl)pyrrolidine-2-carboxamide

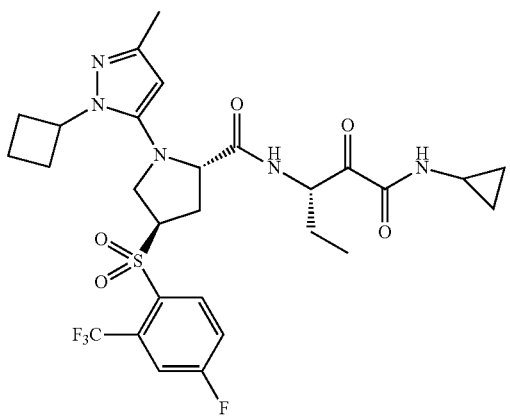 [SMILES: CC[C@H](NC(=O)[C@@H]1C[C@@H](S(=O)(=O)c2ccc(F)cc2C(F)(F)F)CN1c1cc(C)nn1C1CCC1)C(=O)C(=O)NC1CC1]

The title compound was prepared in analogy to Example 1, using (2S,4R)-1-(1-cyclobutyl-3-methyl-1H-pyrazol-5-yl)-N-((2S,3S)-1-(cyclopropylamino)-2-hydroxy-1-oxopentan-3-yl)-4-(4-fluoro-2-(trifluoromethyl)phenylsulfonyl)pyrrolidine-2-carboxamide (prepared as described in U.S. Pat. Appl. US20100267722) in step 1. MS (m/e)=628.22 [M+H⁺].

Example 5

(2S,4R)-1-(2-Nitro-phenyl)-4-(2-trifluoromethyl-benzenesulfonyl)-pyrrolidine-2-carboxylic acid [(S)-1-(benzooxazole-2-carbonyl)-propyl]-amide

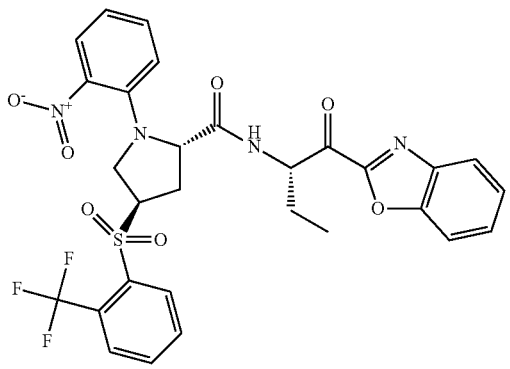 [SMILES: CC[C@H](NC(=O)[C@@H]1C[C@@H](S(=O)(=O)c2ccccc2C(F)(F)F)CN1c1ccccc1[N+](=O)[O-])C(=O)c1nc2ccccc2o1]

The title compound was prepared in analogy to Example 1, using (2S,4R)-1-(2-nitrophenyl)-4-(2-(trifluoromethyl)phenylsulfonyl)pyrrolidine-2-carboxylic acid (prepared as described in U.S. Pat. Appl. US20100267722) and (2S)-2-amino-1-(benzo[d]oxazol-2-yl)butan-1-ol dihydrochloride in step 1. MS (m/e)=631.15 [M+H⁺].

Example 6

(2S,4R)-4-(4-bromo-2-(trifluoromethyl)phenylsulfonyl)-1-(1-cyclobutyl-3-methyl-1H-pyrazol-5-yl)-N—((S)-1-(cyclopropylamino)-1,2-dioxopentan-3-yl)pyrrolidine-2-carboxamide

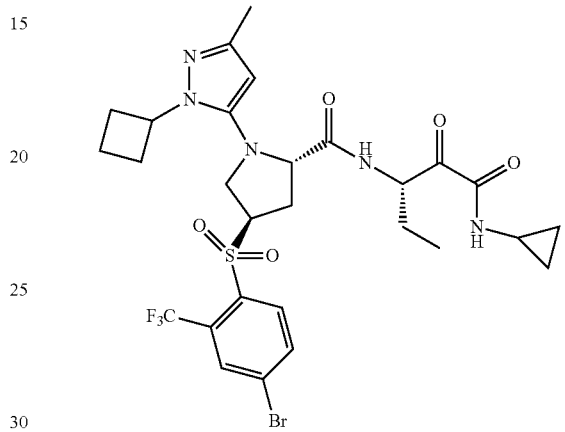

The title compound was prepared in analogy to Example 1, using (2S,4R)-1-(2-nitrophenyl)-4-(2-(trifluoromethyl)phenylsulfonyl)pyrrolidine-2-carboxylic acid (prepared as described in U.S. Pat. Appl. US20100267722) in step 1. MS (m/e)=690.14 [M+H⁺].

Example 7

(2S,4R)—N—((S)-1-(cyclopropylamino)-1,2-dioxopentan-3-yl)-1-(1-(trifluoromethyl)cyclopropanecarbonyl)-4-(2-(trifluoromethyl)phenylsulfonyl)pyrrolidine-2-carboxamide

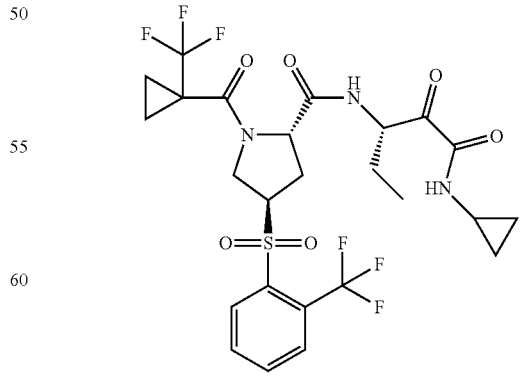

The title compound was prepared in analogy to Example 1, using (2S,4R)-1-(1-(trifluoromethyl)cyclopropanecarbonyl)-4-(2-(trifluoromethyl)phenylsulfonyl)pyrrolidine-2-carboxylic acid in step 1. MS (m/e)=612.16 [M+H⁺].

Example 8

(2S,4R)-1-(1-(4-chlorophenyl)cyclopropanecarbonyl)-4-(2-chlorophenylsulfonyl)-N—((S)-1-(cyclopropylamino)-1,2-dioxopentan-3-yl)pyrrolidine-2-carboxamide

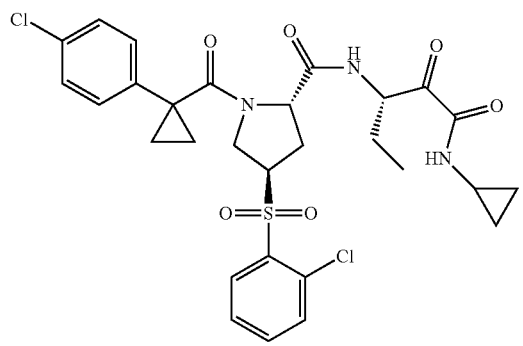 [SMILES: CC[C@H](NC(=O)[C@@H]1C[C@@H](S(=O)(=O)c2ccccc2Cl)CN1C(=O)C1(c2ccc(Cl)cc2)CC1)C(=O)C(=O)NC1CC1]

The title compound was prepared in analogy to Example 1, using (2S,4R)-1-(1-(4-chlorophenyl)cyclopropanecarbonyl)-4-(2-chlorophenylsulfonyl)pyrrolidine-2-carboxylic acid in step 1. MS (m/e)=620.13 [M+H⁺].

Example 9

(2S,4R)-1-(1-(4-chlorophenyl)cyclopropanecarbonyl)-4-(2-chlorophenylsulfonyl)-N—((S)-1-(cyclopropylamino)-1,2-dioxohexan-3-yl)pyrrolidine-2-carboxamide

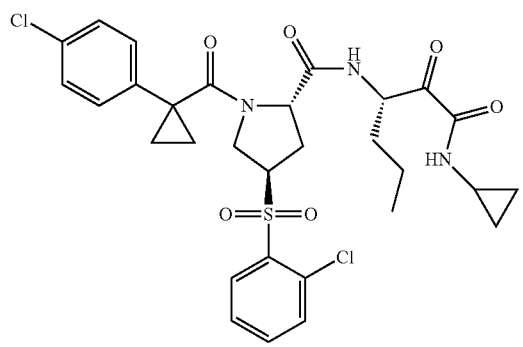 [SMILES: CCC[C@H](NC(=O)[C@@H]1C[C@@H](S(=O)(=O)c2ccccc2Cl)CN1C(=O)C1(c2ccc(Cl)cc2)CC1)C(=O)C(=O)NC1CC1]

The title compound was prepared in analogy to Example 1, using (2S,3S)-3-amino-N-cyclopropyl-2-hydroxyhexanamide and (2S,4R)-1-(1-(4-chlorophenyl)cyclopropanecarbonyl)-4-(2-chlorophenylsulfonyl)pyrrolidine-2-carboxylic acid in step 1. MS (m/e)=634.15 [M+H⁺].

Example 10

(2S,4R)-1-(1-(5-chloro-3-fluoropyridin-2-yl)cyclopropanecarbonyl)-4-(2-chloro-4-(2,2,2-trifluoroethoxy)phenylsulfonyl)-N—((S)-1-(cyclopropylamino)-1,2-dioxopentan-3-yl)pyrrolidine-2-carboxamide

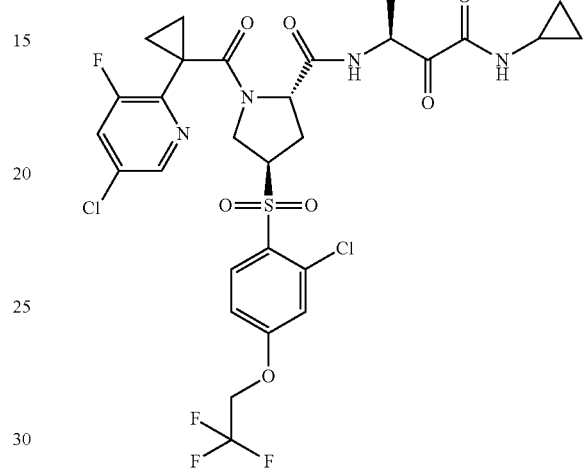

The title compound was prepared in analogy to Example 1, using (2S,4R)-1-(1-(5-chloro-3-fluoropyridin-2-yl)cyclopropanecarbonyl)-4-(2-chloro-4-(2,2,2-trifluoroethoxy)phenylsulfonyl)pyrrolidine-2-carboxylic acid step 1. MS (m/e)=737.12 [M+H⁺].

Example 11

(2S,4R)-1-(1-(4-chlorophenyl)cyclopropanecarbonyl)-N—((S)-1-(cyclopropylamino)-1,2-dioxopentan-3-yl)-4-(4-(2,2,2-trifluoroethoxy)-2-trifluoromethyl)phenylsulfonyl)pyrrolidine-2-carboxamide

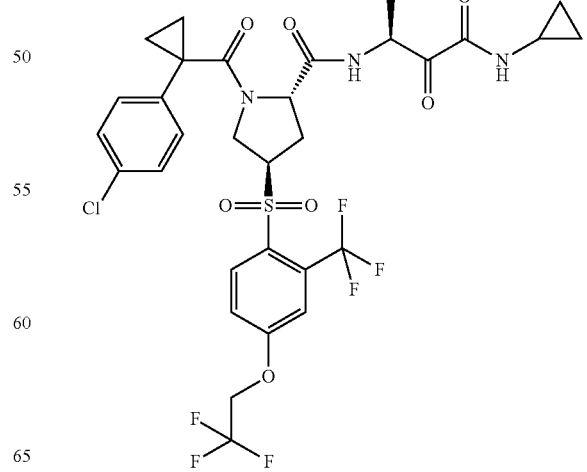

The title compound was prepared in analogy to Example 1, using (2S,4R)-1-[1-(4-chloro-phenyl)-cyclopropanecarbonyl]-4-[4-(2,2,2-trifluoro-ethoxy)-2-trifluoromethyl-benzenesulfonyl]-pyrrolidine-2-carboxylic acid in step 1. MS (m/e)=752.16 [M+H$^+$].

Example 12

(2S,4R)—N—((S)-1-(benzo[d]oxazol-2-yl)-1-oxobutan-2-yl)-1-(1-(4-chlorophenyl)cyclopropanecarbonyl)-4-(2-chlorophenylsulfonyl)pyrrolidine-2-carboxamide

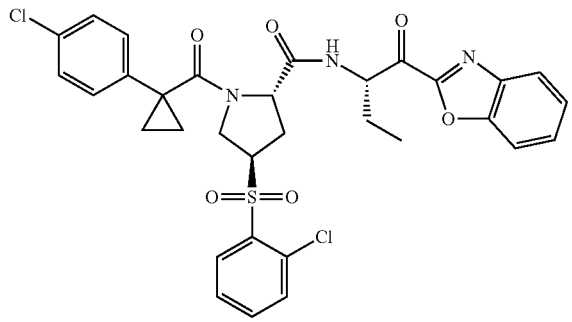 [SMILES: CC[C@H](NC(=O)[C@@H]1C[C@@H](S(=O)(=O)c2ccccc2Cl)CN1C(=O)C1(c2ccc(Cl)cc2)CC1)C(=O)c1nc2ccccc2o1]

The title compound was prepared in analogy to Example 1, using 2-amino-1-benzooxazol-2-yl-butan-1-ol in step 1. MS (m/e)=654.12 [M+H$^+$].

Example 13

(2S,4R)-1-(1-(4-chloro-2-fluorophenyl)cyclopropanecarbonyl)-4-(2-chlorophenylsulfonyl)-N—((S)-1-(cyclopropylamino)-1,2-dioxopentan-3-yl)pyrrolidine-2-carboxamide

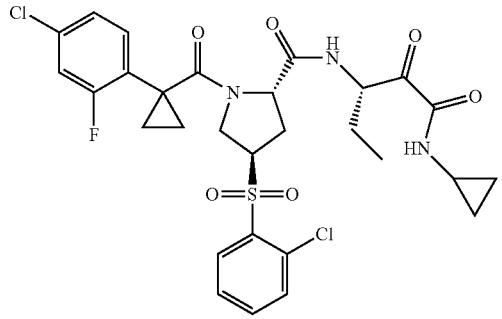

The title compound was prepared in analogy to Example 1, using (2S,4R)-4-(2-chloro-benzenesulfonyl)-1-[1-(4-chloro-2-fluoro-phenyl)-cyclopropanecarbonyl]-pyrrolidine-2-carboxylic acid in step 1. MS (m/e)=638.13 [M+H$^+$].

Example 14

(2S,4R)-1-(1-(4-bromo-2-fluorophenyl)cyclopropanecarbonyl)-4-(2-chlorophenylsulfonyl)-N—((S)-1-(cyclopropylamino)-1,2-dioxopentan-3-yl)pyrrolidine-2-carboxamide

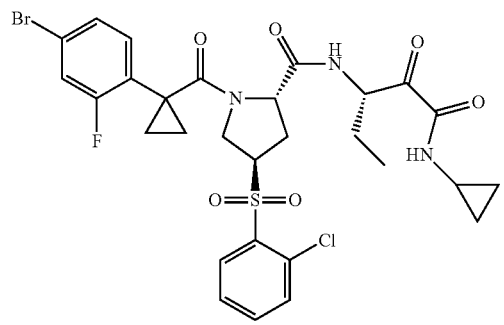 [SMILES: CC[C@H](NC(=O)[C@@H]1C[C@@H](S(=O)(=O)c2ccccc2Cl)CN1C(=O)C1(c2ccc(Cl)cc2F)CC1)C(=O)C(=O)NC1CC1]

The title compound was prepared in analogy to Example 1, using (2S,4R)-1-[1-(4-bromo-2-fluoro-phenyl)-cyclopropanecarbonyl]-4-(2-chloro-benzenesulfonyl)-pyrrolidine-2-carboxylic acid in step 1. MS (m/e)=684.08 [M+H$^+$].

Example 15

(2S,4R)-1-(1-(4-bromophenyl)cyclopropanecarbonyl)-4-(2-chlorophenylsulfonyl)-N—((S)-1-(cyclopropylamino)-1,2-dioxopentan-3-yl)pyrrolidine-2-carboxamide

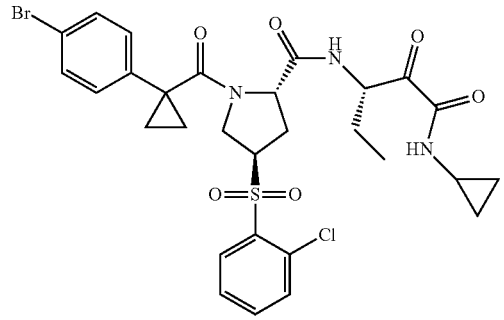 [SMILES: CC[C@H](NC(=O)[C@@H]1C[C@@H](S(=O)(=O)c2ccccc2Cl)CN1C(=O)C1(c2ccc(Br)cc2)CC1)C(=O)C(=O)NC1CC1]

The title compound was prepared in analogy to Example 1, using (2S,4R)-1-[1-(4-bromo-phenyl)-cyclopropanecarbonyl]-4-(2-chloro-benzenesulfonyl)-pyrrolidine-2-carboxylic acid in step 1. MS (m/e)=666.08 [M+H⁺].

Example 16

(2S,4R)-1-(1-(4-bromophenyl)cyclopropanecarbonyl)-4-(2-chlorophenylsulfonyl)-N—((S)-1-(cyclopropylamino)-1,2-dioxohexan-3-yl)pyrrolidine-2-carboxamide

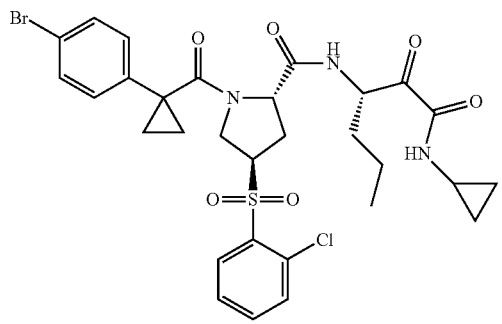

The title compound was prepared in analogy to Example 1, using (2S,4R)-1-[1-(4-bromo-phenyl)-cyclopropanecarbonyl]-4-(2-chloro-benzenesulfonyl)-pyrrolidine-2-carboxylic acid and (2S,3S)-3-amino-N-cyclopropyl-2-hydroxyhexanamide in step 1. MS (m/e)=680.1 [M+H⁺].

Example 17

(2S,4R)-4-(2-chlorophenylsulfonyl)-N—((S)-1-(cyclopropylamino)-1,2-dioxopentan-3-yl)-1-(1-(4-iodophenyl)cyclopropanecarbonyl)pyrrolidine-2-carboxamide

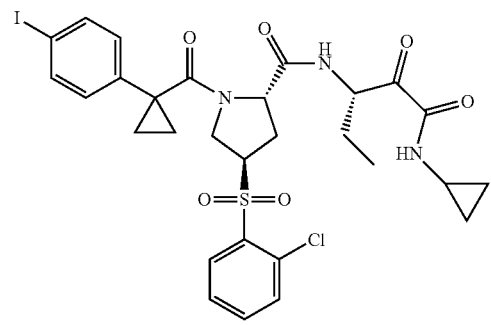 [SMILES: CC[C@H](NC(=O)[C@@H]1C[C@@H](S(=O)(=O)c2ccccc2Cl)CN1C(=O)C1(c2ccc(I)cc2)CC1)C(=O)C(=O)NC1CC1]

The title compound was prepared in analogy to Example 1, using (2S,4R)-4-(2-chloro-benzenesulfonyl)-1-[1-(4-iodophenyl)-cyclopropanecarbonyl]-pyrrolidine-2-carboxylic acid in step 1. MS (m/e)=712.07 [M+H⁺].

Example 18

(2S,4R)-4-(2-chlorophenylsulfonyl)-N—((S)-1-(cyclopropylamino)-1,2-dioxohexan-3-yl)-1-(1-(4-iodophenyl)cyclopropanecarbonyl)pyrrolidine-2-carboxamide

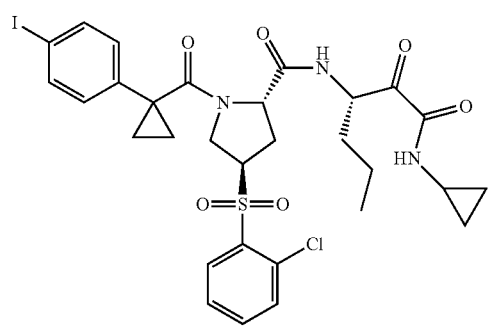 [SMILES: CCC[C@H](NC(=O)[C@@H]1C[C@@H](S(=O)(=O)c2ccccc2Cl)CN1C(=O)C1(c2ccc(I)cc2)CC1)C(=O)C(=O)NC1CC1]

The title compound was prepared in analogy to Example 1, using (2S,4R)-4-(2-chloro-benzenesulfonyl)-1-[1-(4-iodophenyl)-cyclopropanecarbonyl]-pyrrolidine-2-carboxylic acid and (2S,3S)-3-amino-N-cyclopropyl-2-hydroxyhexanamide in step 1. MS (m/e)=726.09 [M+H⁺].

Example 19

(2S,4R)-1-(1-(5-chloro-3-fluoropyridin-2-yl)cyclopropanecarbonyl)-N—((S)-1-(cyclopropylamino)-1,2-dioxopentan-3-yl)-4-(2-(trifluoromethyl)phenylsulfonyl)pyrrolidine-2-carboxamide

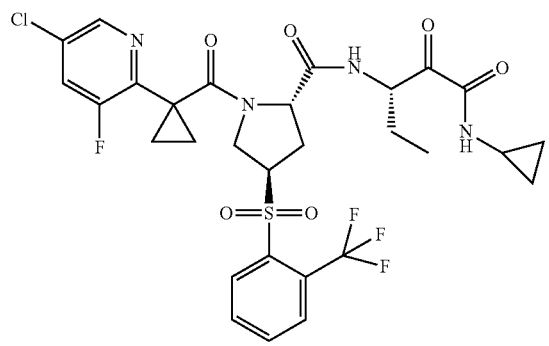 [SMILES: CC[C@H](NC(=O)[C@@H]1C[C@@H](S(=O)(=O)c2ccccc2C(F)(F)F)CN1C(=O)C1(c2ncc(Cl)cc2F)CC1)C(=O)C(=O)NC1CC1]

The title compound was prepared in analogy to Example 1, using (2S,4R)-1-[1-(5-chloro-3-fluoro-pyridin-2-yl)-cyclopropanecarbonyl]-4-(2-trifluoromethyl-benzenesulfonyl)-pyrrolidine-2-carboxylic acid in step 1. MS (m/e)=673.15 [M+H⁺].

Example 20

(2S,4R)-1-(1-(5-chloro-3-fluoropyridin-2-yl)cyclopropanecarbonyl)-N—((S)-1-(cyclopropylamino)-1,2-dioxohexan-3-yl)-4-(2-(trifluoromethyl)phenylsulfonyl)pyrrolidine-2-carboxamide

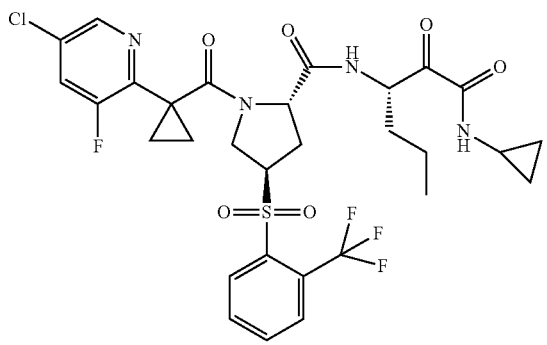 [SMILES: CCC[C@H](NC(=O)[C@@H]1C[C@@H](S(=O)(=O)c2ccccc2C(F)(F)F)CN1C(=O)C1(c2ncc(Cl)cc2F)CC1)C(=O)C(=O)NC1CC1]

The title compound was prepared in analogy to Example 1, using (2S,4R)-1-[1-(5-chloro-3-fluoro-pyridin-2-yl)-cyclopropanecarbonyl]-4-(2-trifluoromethyl-benzenesulfonyl)-pyrrolidine-2-carboxylic acid and (2S,3S)-3-amino-N-cyclopropyl-2-hydroxyhexanamide in step 1. MS (m/e)=687.17 [M+H⁺].

Example 21

(2S,4R)-1-(1-(4-chlorophenyl)cyclopropanecarbonyl)-N—((S)-1-(cyclopropylamino)-1,2-dioxopentan-3-yl)-4-(2-(trifluoromethyl)phenylsulfonyl)pyrrolidine-2-carboxamide

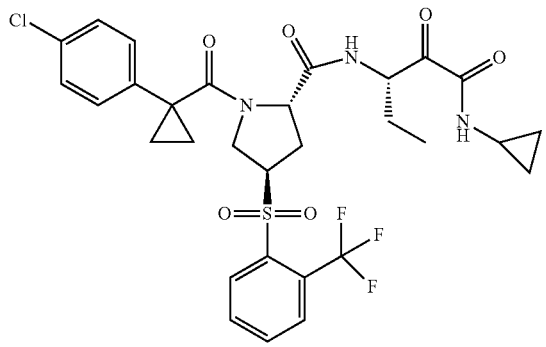 [SMILES: CC[C@H](NC(=O)[C@@H]1C[C@@H](S(=O)(=O)c2ccccc2C(F)(F)F)CN1C(=O)C1(c2ccc(Cl)cc2)CC1)C(=O)C(=O)NC1CC1]

The title compound was prepared in analogy to Example 1, using (2S,4R)-1-[1-(4-chloro-phenyl)-cyclopropanecarbonyl]-4-(2-trifluoromethyl-benzenesulfonyl)-pyrrolidine-2-carboxylic acid in step 1. MS (m/e)=654.16 [M+H⁺].

Example 22

(2S,4R)-1-(1-(4-chlorophenyl)cyclopropanecarbonyl)-N—((S)-1-(cyclopropylamino)-1,2-dioxohexan-3-yl)-4-(2-(trifluoromethyl)phenylsulfonyl)pyrrolidine-2-carboxamide

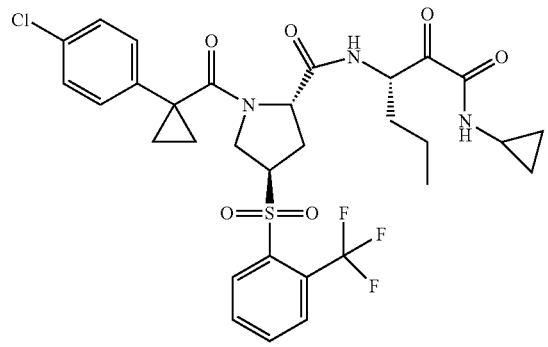

The title compound was prepared in analogy to Example 1, using (2S,4R)-1-[1-(4-chloro-phenyl)-cyclopropanecarbonyl]-4-(2-trifluoromethyl-benzenesulfonyl)-pyrrolidine-2-carboxylic acid and (2S,3S)-3-amino-N-cyclopropyl-2-hydroxyhexanamide in step 1. MS (m/e)=668.18 [M+H⁺].

Example 23

(2S,4R)-1-(1-(5-bromo-3-fluoropyridin-2-yl)cyclopropanecarbonyl)-4-(2-chlorophenylsulfonyl)-N—((S)-1-(cyclopropylamino)-1,2-dioxopentan-3-yl)pyrrolidine-2-carboxamide

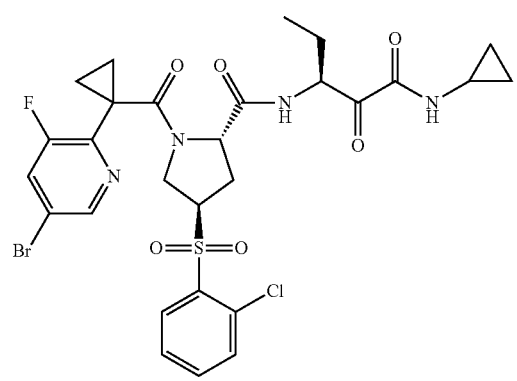 [SMILES: CC[C@H](NC(=O)[C@@H]1C[C@@H](S(=O)(=O)c2ccccc2Cl)CN1C(=O)C1(c2ncc(Br)cc2F)CC1)C(=O)C(=O)NC1CC1]

The title compound was prepared in analogy to Example 1, using 1-(5-bromo-3-fluoropyridin-2-yl)cyclopropanecarboxylic acid in step 1. MS (m/e)=685.07 [M+H$^+$].

Example 24

(2S,4R)-1-(1-(5-chloro-3-fluoropyridin-2-yl)cyclopropanecarbonyl)-4-(2-chlorophenylsulfonyl)-N—((S)-1-(cyclopropylamino)-1,2-dioxohexan-3-yl)pyrrolidine-2-carboxamide

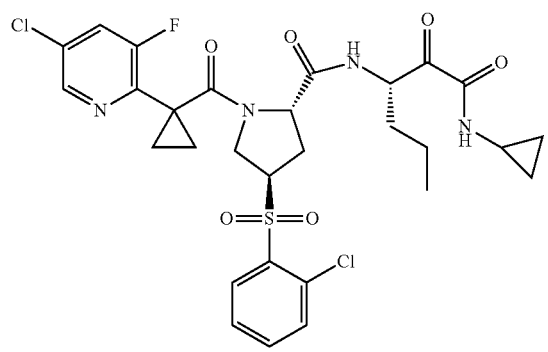 [SMILES: CCC[C@H](NC(=O)[C@@H]1C[C@@H](S(=O)(=O)c2ccccc2Cl)CN1C(=O)C1(c2ncc(Cl)cc2F)CC1)C(=O)C(=O)NC1CC1]

The title compound was prepared in analogy to Example 1, using (2S,4R)-4-(2-chloro-benzenesulfonyl)-1-[1-(5-chloro-3-fluoro-pyridin-2-yl)-cyclopropanecarbonyl]-pyrrolidine-2-carboxylic acid and (2S,3S)-3-amino-N-cyclopropyl-2-hydroxyhexanamide in step 1. MS (m/e)=653.14 [M+H$^+$].

Example 25

(2S,4R)-1-(1-(5-chloro-3-fluoropyridin-2-yl)cyclopropanecarbonyl)-4-(2-chlorophenylsulfonyl)-N—((S)-1-(cyclopropylamino)-1,2-dioxopentan-3-yl)pyrrolidine-2-carboxamide

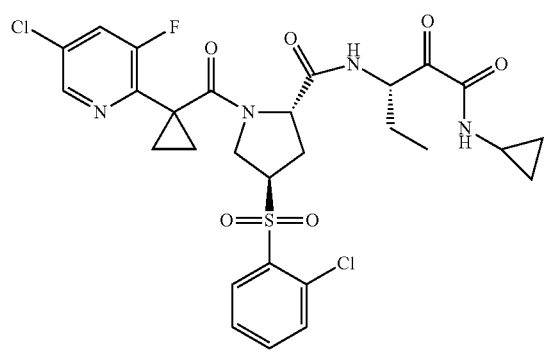 [SMILES: CC[C@H](NC(=O)[C@@H]1C[C@@H](S(=O)(=O)c2ccccc2Cl)CN1C(=O)C1(c2ncc(Cl)cc2F)CC1)C(=O)C(=O)NC1CC1]

The title compound was prepared in analogy to Example 1, using (2S,4R)-4-(2-chloro-benzenesulfonyl)-1-[1-(5-chloro-3-fluoro-pyridin-2-yl)-cyclopropanecarbonyl]-pyrrolidine-2-carboxylic acid in step 1. MS (m/e)=639.12 [M+H$^+$].

Example 26

(2S,4R)-1-(1-(4-chlorophenyl)cyclopropanecarbonyl)-4-(2-chlorophenylsulfonyl)-N-(4-(cyclopropylamino)-2-methyl-3,4-dioxobutan-2-yl)pyrrolidine-2-carboxamide

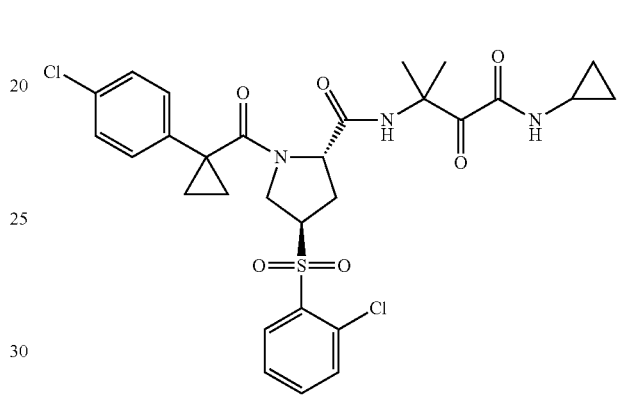

The title compound was prepared in analogy to Example 1, using 3-amino-N-cyclopropyl-2-hydroxy-3-methylbutanamide in step 1. MS (m/e)=620.13 [M+H$^+$].

Example 27

(2S,4R)-1-(1-(4-chlorophenyl)cyclopropanecarbonyl)-4-(2-chlorophenylsulfonyl)-N-(1-(2-(cyclopropylamino)-2-oxoacetyl)cyclopropyl)pyrrolidine-2-carboxamide

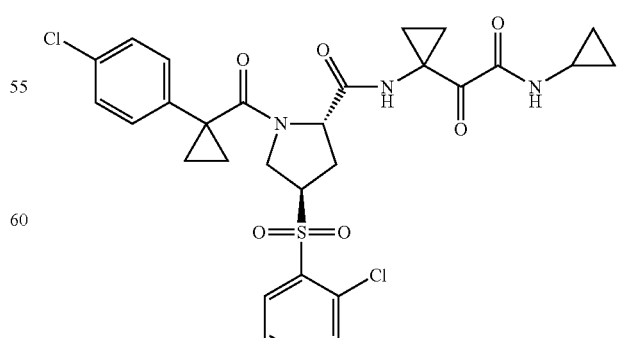

The title compound was prepared in analogy to Example 1, using 2 1-aminocyclopropyl)-N-cyclopropyl-2-hydroxyacetamide in step 1. MS (m/e)=618.12 [M+H$^+$].

Example 28

(2S,4R)-1-(1-(4-chlorophenyl)cyclopropanecarbonyl)-4-(2-chlorophenylsulfonyl)-N—((S)-1-(cyclopropylamino)-4-methyl-1,2-dioxopentan-3-yl)pyrrolidine-2-carboxamide

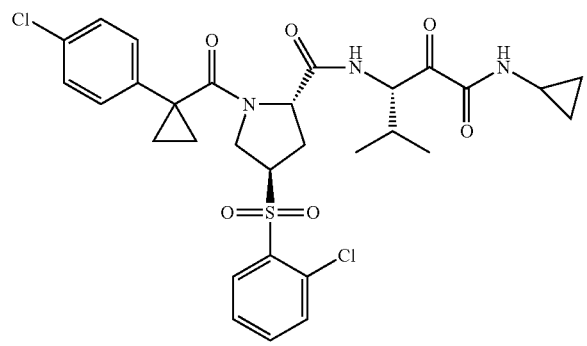 [SMILES: CC(C)[C@H](NC(=O)[C@@H]1C[C@@H](S(=O)(=O)c2ccccc2Cl)CN1C(=O)C1(c2ccc(Cl)cc2)CC1)C(=O)C(=O)NC1CC1]

The title compound was prepared in analogy to Example 1, using (2S,3S)-3-amino-N-cyclopropyl-2-hydroxy-4-methylpentanamide dihydrochloride in step 1. MS (m/e)=632.14 [M–H$^+$].

Example 29

(2S,4R)-1-(1-(4-chlorophenyl)cyclopropanecarbonyl)-4-(2-chlorophenylsulfonyl)-N—((S)-1-(cyclopropylamino)-5-methyl-1,2-dioxohexan-3-yl)pyrrolidine-2-carboxamide

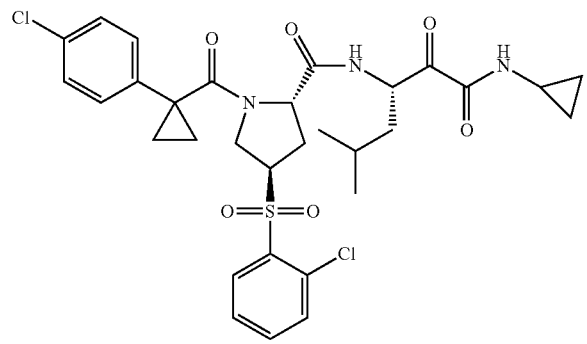 [SMILES: CC(C)C[C@H](NC(=O)[C@@H]1C[C@@H](S(=O)(=O)c2ccccc2Cl)CN1C(=O)C1(c2ccc(Cl)cc2)CC1)C(=O)C(=O)NC1CC1]

The title compound was prepared in analogy to Example 1, (2S,3S)-3-amino-N-cyclopropyl-2-hydroxy-5-methylhexanamide dihydrochloride in step 1. MS (m/e)=646.15 [M–H$^+$].

Example 30

(2S,4R)-1-(1-(4-chlorophenyl)cyclopropanecarbonyl)-4-(2-chlorophenylsulfonyl)-N—((S)-1-cyclohexyl-4-(cyclopropylamino)-3,4-dioxobutan-2-yl) pyrrolidine-2-carboxamide

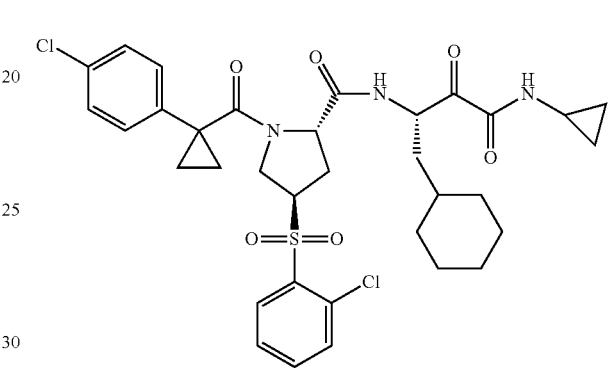

The title compound was prepared in analogy to Example 1, using (2S,3S)-3-amino-4-cyclohexyl-N-cyclopropyl-2-hydroxybutanamide dihydrochloride in step 1. MS (m/e)= 686.19 [M–H$^+$].

Example 31

(2S,4R)—N—((S)-1-(butylamino)-1,2-dioxopentan-3-yl)-1-(1-(4-chlorophenyl)cyclopropanecarbonyl)-4-(2-chlorophenylsulfonyl)pyrrolidine-2-carboxamide

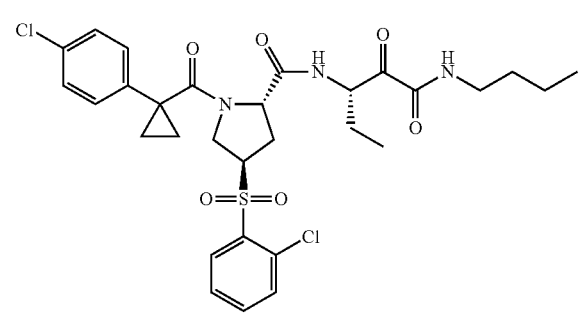 [SMILES: CCCCNC(=O)C(=O)[C@H](CC)NC(=O)[C@@H]1C[C@@H](S(=O)(=O)c2ccccc2Cl)CN1C(=O)C1(c2ccc(Cl)cc2)CC1]

The title compound was prepared in analogy to Example 1, using (2S,3S)-3-amino-N-butyl-2-hydroxypentanamide dihydrochloride in step 1. MS (m/e)=634.15 [M–H⁺].

Example 32

(2S,4R)—N—((S)-1-(butylamino)-1,2-dioxohexan-3-yl)-1-(1-(4-chlorophenyl)cyclopropanecarbonyl)-4-(2-chlorophenylsulfonyl)pyrrolidine-2-carboxamide

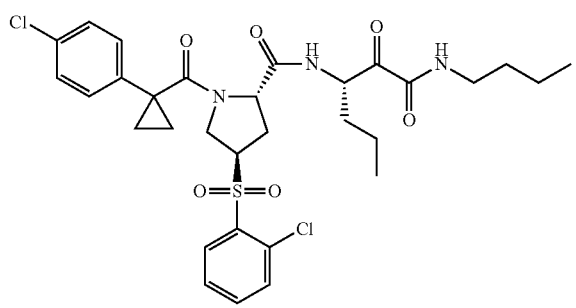 [SMILES: CCCCNC(=O)C(=O)[C@H](CCC)NC(=O)[C@@H]1C[C@@H](S(=O)(=O)c2ccccc2Cl)CN1C(=O)C1(c2ccc(Cl)cc2)CC1]

The title compound was prepared in analogy to Example 1, using (2S,3S)-3-amino-N-butyl-2-hydroxyhexanamide dihydrochloride in step 1. MS (m/e)=648.17 [M–H⁺].

Example 33

(2S,4R)—N—((S)-1-(benzylamino)-1,2-dioxopentan-3-yl)-1-(1-(4-chlorophenyl)cyclopropanecarbonyl)-4-(2-chlorophenylsulfonyl)pyrrolidine-2-carboxamide

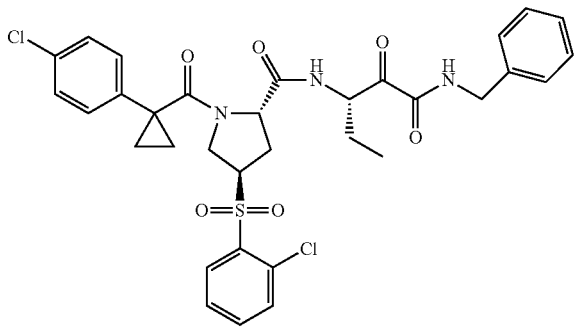 [SMILES: CC[C@H](NC(=O)[C@@H]1C[C@@H](S(=O)(=O)c2ccccc2Cl)CN1C(=O)C1(c2ccc(Cl)cc2)CC1)C(=O)C(=O)NCc1ccccc1]

The title compound was prepared in analogy to Example 1, using (2S,3S)-3-amino-N-benzyl-2-hydroxypentanamide dihydrochloride in step 1. MS (m/e)=668.14 [M–H⁺].

Example 34

(2S,4R)-1-(1-(4-chlorophenyl)cyclopropanecarbonyl)-4-(2-chlorophenylsulfonyl)-N—((S)-4-(cyclopropylamino)-3,4-dioxobutan-2-yl)pyrrolidine-2-carboxamide

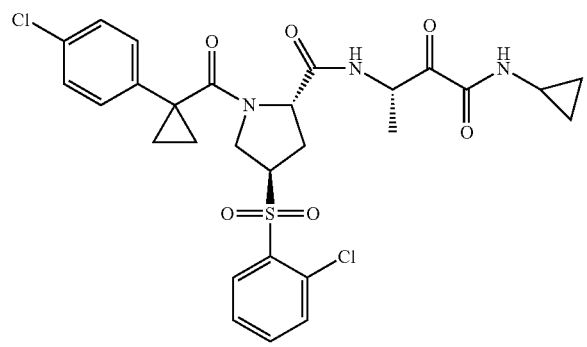 [SMILES: C[C@H](NC(=O)[C@@H]1C[C@@H](S(=O)(=O)c2ccccc2Cl)CN1C(=O)C1(c2ccc(Cl)cc2)CC1)C(=O)C(=O)NC1CC1]

The title compound was prepared in analogy to Example 1, using (2S,3S)-3-amino-N-cyclopropyl-2-hydroxybutanamide dihydrochloride in step 1. MS (m/e)=604.11 [M–H⁺].

Example 35

(2S,4R)—N—((S)-1-(benzylamino)-1,2-dioxohexan-3-yl)-1-(1-(4-chlorophenyl)cyclopropanecarbonyl)-4-(2-chlorophenylsulfonyl)pyrrolidine-2-carboxamide

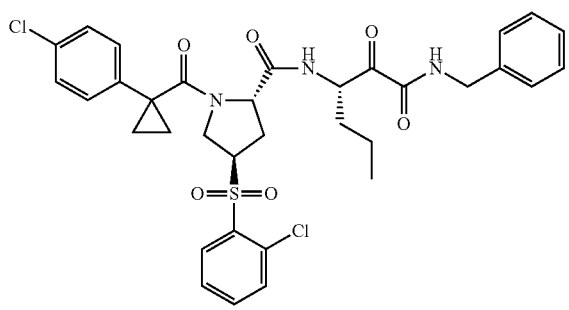 [SMILES: CCC[C@H](NC(=O)[C@@H]1C[C@@H](S(=O)(=O)c2ccccc2Cl)CN1C(=O)C1(c2ccc(Cl)cc2)CC1)C(=O)C(=O)NCc1ccccc1]

The title compound was prepared in analogy to Example 1, using (2S,3S)-3-amino-N-benzyl-2-hydroxyhexanamide dihydrochloride in step 1. MS (m/e)=682.15 [M–H⁺].

Example 36

(2S,4R)-1-(1-(4-chlorophenyl)cyclopropanecarbonyl)-4-(2-chlorophenylsulfonyl)-N-((3S)-1,2-dioxo-1-(pentan-2-ylamino)pentan-3-yl)pyrrolidine-2-carboxamide

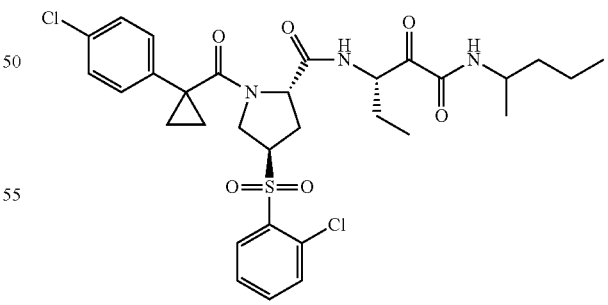

The title compound was prepared in analogy to Example 1, using (2S,3S)-3-amino-2-hydroxy-N-(pentan-2-yl)pentanamide dihydrochloride in step 1. MS (m/e)=648.17 [M–H⁺].

Example 37

(2S,4R)-1-(1-(4-chlorophenyl)cyclopropanecarbonyl)-4-(2-chlorophenylsulfonyl)-N-((3S)-1,2-dioxo-1-(pentan-2-ylamino)hexan-3-yl)pyrrolidine-2-carboxamide

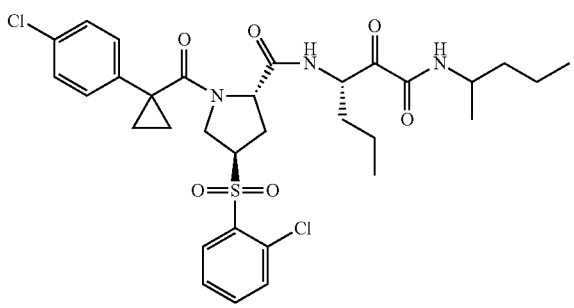 [SMILES: CCCC(C)NC(=O)C(=O)[C@H](CCC)NC(=O)[C@@H]1C[C@@H](S(=O)(=O)c2ccccc2Cl)CN1C(=O)C1(c2ccc(Cl)cc2)CC1]

The title compound was prepared in analogy to Example 1, using (2S,3S)-3-amino-2-hydroxy-N-(pentan-2-yl)hexanamide dihydrochloride in step 1. MS (m/e)=664.2 [M−H⁺].

Example 38

(2S,4R)-1-(1-(4-chlorophenyl)cyclopropanecarbonyl)-N—((S)-1-(cyclopropylamino)-1,2-dioxopentan-2-yl)-4-(2,4-dichlorophenylsulfonyl)pyrrolidine-2-carboxamide

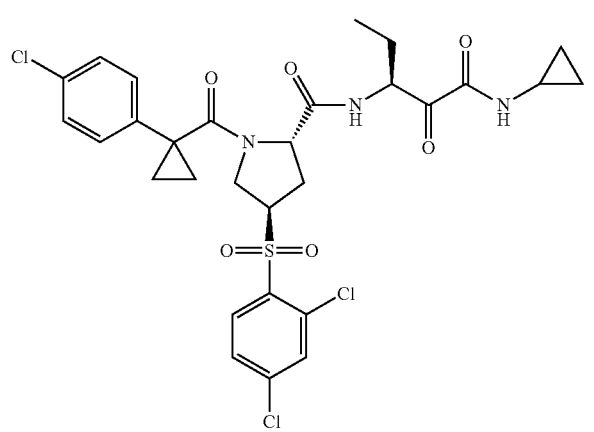 [SMILES: CC[C@H](NC(=O)[C@@H]1C[C@@H](S(=O)(=O)c2ccc(Cl)cc2Cl)CN1C(=O)C1(c2ccc(Cl)cc2)CC1)C(=O)C(=O)NC1CC1]

The title compound was prepared in analogy to Example 1, using (2S,4R)-1-[1-(4-chloro-phenyl)-cyclopropanecarbonyl]-4-(2,4-dichloro-benzenesulfonyl)-pyrrolidine-2-carboxylic acid in step 1. MS (m/e)=656.09 [M+H⁺].

Example 39

(2S,4R)-4-(2-chloro-4-fluorophenylsulfonyl)-1-(1-(4-chlorophenyl)cyclopropanecarbonyl)-N—((S)-1-(cyclopropylamino)-1,2-dioxopentan-3-yl)pyrrolidine-2-carboxamide

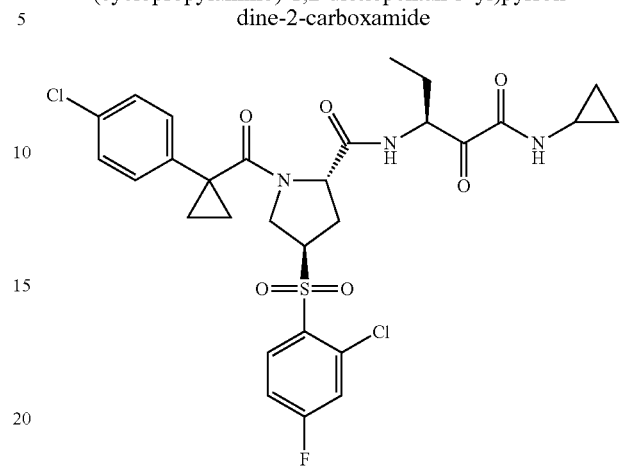

The title compound was prepared in analogy to Example 1, using (2S,4R)-4-(2-chloro-4-fluoro-benzenesulfonyl)-1-[1-(4-chloro-phenyl)-cyclopropanecarbonyl]-pyrrolidine-2-carboxylic acid in step 1. MS (m/e)=638.12 [M+H⁺].

Example 40

(2S,4R)-1-(1-(4-chlorophenyl)cyclopropanecarbonyl)-4-(2-chlorophenylsulfonyl)-N—((S)-1,2-dioxo-1-(2,2,2-trifluoroethylamino)hexan-3-yl)pyrrolidine-2-carboxamide

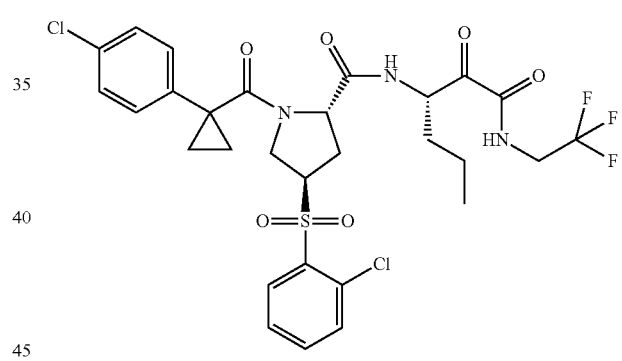

The title compound was prepared in analogy to Example 1, using (2S,3S)-3-amino-2-hydroxy-N-(2,2,2-trifluoroethyl)hexanamide in step 1. MS (m/e)=676.12 [M+H⁺].

Example 41

(2S,4R)-1-(1-(4-chlorophenyl)cyclopropanecarbonyl)-4-(2-chlorophenylsulfonyl)-N—((S)-1-(isopropylamino)-1,2-dioxohexan-3-yl)pyrrolidine-2-carboxamide

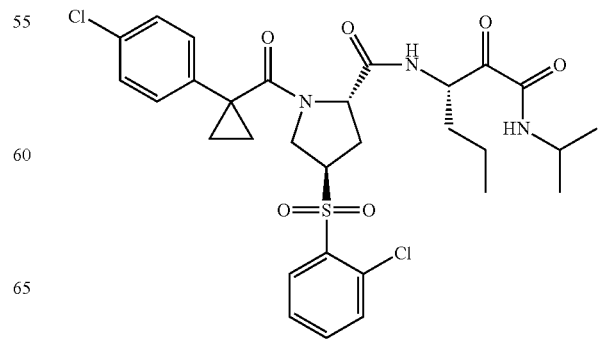

The title compound was prepared in analogy to Example 1, using (2S,3S)-3-amino-2-hydroxy-N-isopropylhexanamide in step 1. MS (m/e)=636.17 [M+H⁺].

Example 42

(2S,4R)-1-(1-(4-chlorophenyl)cyclopropanecarbonyl)-N—((S)-1-(cyclopropylamino)-1,2-dioxohexan-3-yl)-4-(2,4-dichlorophenylsulfonyl)pyrrolidine-2-carboxamide

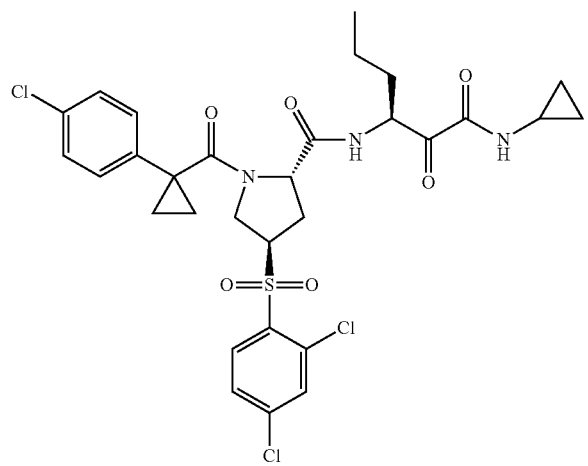

The title compound was prepared in analogy to Example 1, using (2S,4R)-1-(1-(4-chlorophenyl)cyclopropanecarbonyl)-4-(2,4-dichlorophenylsulfonyl)pyrrolidine-2-carboxylic acid and (2S,3S)-3-amino-N-cyclopropyl-2-hydroxyhexanamide in step 1. MS (m/e)=670.11 [M+H⁺].

Example 43

(2S,4R)-1-(1-(4-chlorophenyl)cyclopropanecarbonyl)-4-(2-chlorophenylsulfonyl)-N—((S)-1-(ethylamino)-1,2-dioxopentan-3-yl)pyrrolidine-2-carboxamide

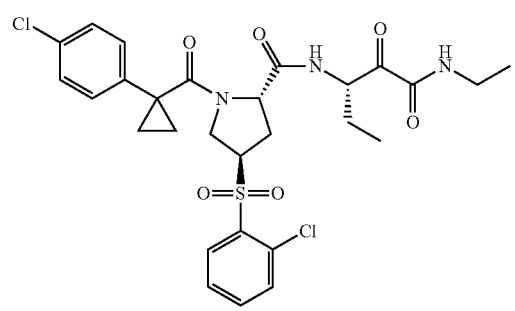 [SMILES: CCNC(=O)C(=O)[C@H](CC)NC(=O)[C@@H]1C[C@@H](S(=O)(=O)c2ccccc2Cl)CN1C(=O)C1(c2ccc(Cl)cc2)CC1]

The title compound was prepared in analogy to Example 1, using (2S,3S)-3-amino-N-ethyl-2-hydroxypentanamide dihydrochloride in step 1. MS (m/e)=606.12 [M−H⁺].

Example 44

(2S,4R)-1-(1-(4-chlorophenyl)cyclopropanecarbonyl)-4-(2-chlorophenylsulfonyl)-N—((S)-1-(ethylamino)-1,2-dioxohexan-3-yl)pyrrolidine-2-carboxamide

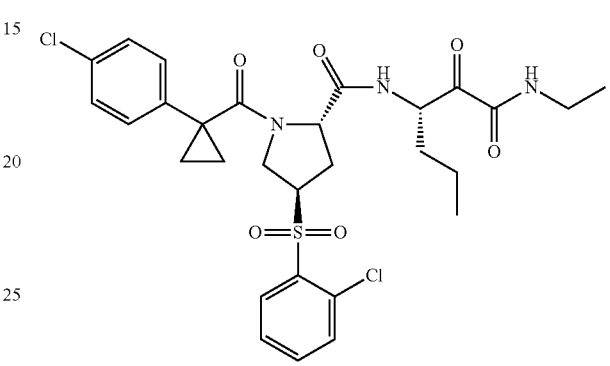

The title compound was prepared in analogy to Example 1, using (2S,3S)-3-amino-N-ethyl-2-hydroxyhexanamide dihydrochloride in step 1. MS (m/e)=622.15 [M+H⁺].

Example 45

(2S,4R)-4-(2-chloro-4-((S)-1,1,1-trifluoropropan-2-yloxy)phenylsulfonyl)-1-(1-(4-chlorophenyl)cyclopropanecarbonyl)-N—((S)-1-(cyclopropylamino)-1,2-dioxopentan-3-yl)pyrrolidine-2-carboxamide

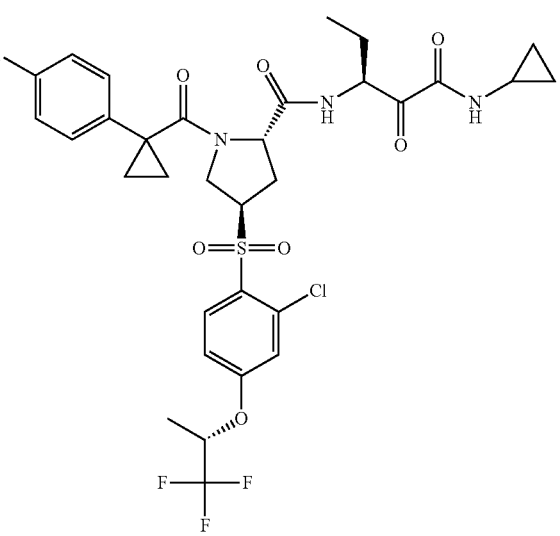

The title compound was prepared in analogy to Example 1, using (2S,4R)-1-[1-(4-chloro-phenyl)-cyclopropanecarbonyl]-4-[2-chloro-4-((S)-2,2,2-trifluoro-1-methyl-ethoxy)-benzenesulfonyl]-pyrrolidine-2-carboxylic acid in step 1. MS (m/e)=732.15 [M+H⁺].

Example 46

(2S,4R)-4-(2-chloro-4-((S)-1,1,1-trifluoropropan-2-yloxy)phenylsulfonyl)-1-(1-(4-chlorophenyl)cyclopropanecarbonyl)-N—((S)-1-(cyclopropylamino)-1,2-dioxohexan-3-yl)pyrrolidine-2-carboxamide

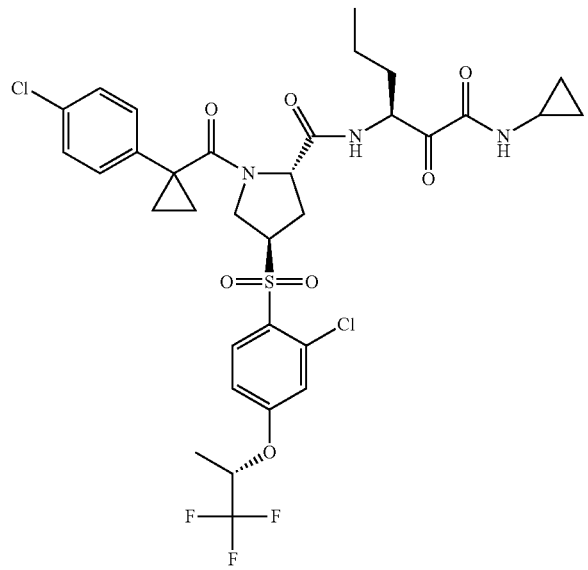 [SMILES: CCC[C@H](NC(=O)[C@@H]1C[C@@H](S(=O)(=O)c2ccc(O[C@@H](C)C(F)(F)F)cc2Cl)CN1C(=O)C1(c2ccc(Cl)cc2)CC1)C(=O)C(=O)NC1CC1]

The title compound was prepared in analogy to Example 1, using (2S,3S)-3-amino-N-cyclopropyl-2-hydroxyhexanamide and (2S,4R)-1-[1-(4-chloro-phenyl)-cyclopropanecarbonyl]-4-[2-chloro-4-((S)-2,2,2-trifluoro-1-methyl-ethoxy)-benzenesulfonyl]-pyrrolidine-2-carboxylic acid in step 1. MS (m/e)=746.17 [M+H⁺].

Example 47

(2S,4R)-1-(1-(4-chlorophenyl)cyclopropanecarbonyl)-4-(2-chlorophenylsulfonyl)-N—((S)-1-(cyclopropyl(methyl)amino)-1,2-dioxohexan-3-yl)pyrrolidine-2-carboxamide

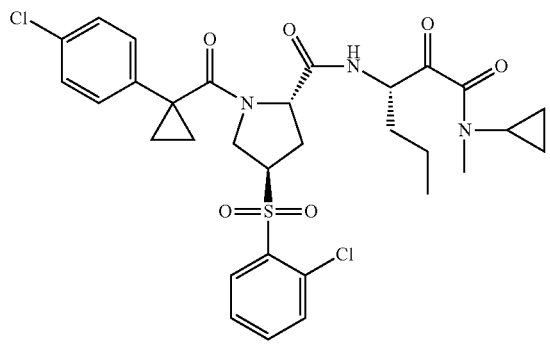 [SMILES: CCC[C@H](NC(=O)[C@@H]1C[C@@H](S(=O)(=O)c2ccccc2Cl)CN1C(=O)C1(c2ccc(Cl)cc2)CC1)C(=O)C(=O)N(C)C1CC1]

The title compound was prepared in analogy to Example 1, using (2S,3S)-3-amino-N-cyclopropyl-2-hydroxy-N-methylhexanamide in step 1. MS (m/e)=648.17 [M+H⁺].

Example 48

(2S,4R)-4-(2-chloro-4-fluorophenylsulfonyl)-1-(1-(4-chlorophenyl)cyclopropanecarbonyl)-N—((S)-1-(cyclopropylamino)-1,2-dioxohexan-3-yl)pyrrolidine-2-carboxamide

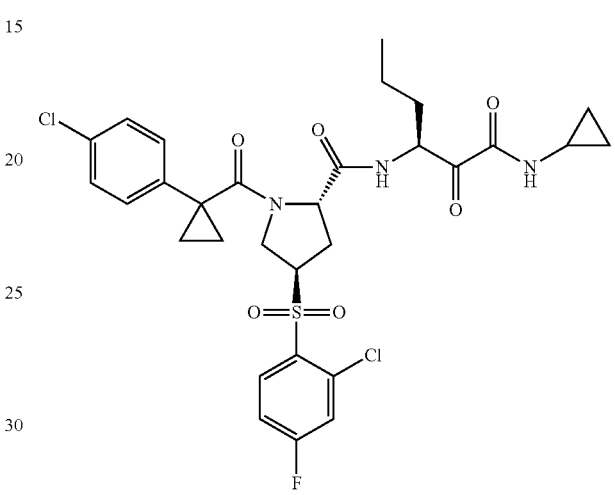

The title compound was prepared in analogy to Example 1, using (2S,3S)-3-amino-N-cyclopropyl-2-hydroxyhexanamide and (2S,4R)-4-(2-Chloro-4-fluoro-benzenesulfonyl)-1-[1-(4-chloro-phenyl)-cyclopropanecarbonyl]-pyrrolidine-2-carboxylic acid in step 1. MS (m/e)=652.14 [M+H⁺].

Example 49

(2S,4R)-1-(1-(4-chlorophenyl)cyclopropanecarbonyl)-4-(2-chlorophenylsulfonyl)-N—((S)-1,2-dioxo-1-(phenethylamino)pentan-3-yl)pyrrolidine-2-carboxamide

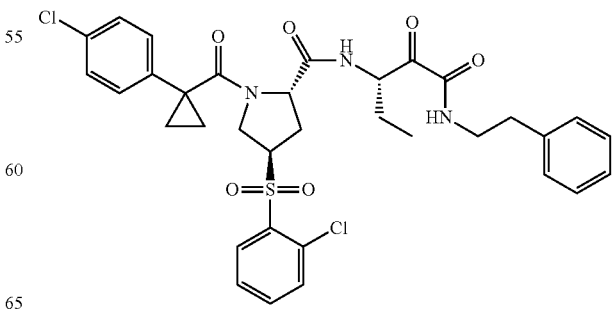

The title compound was prepared in analogy to Example 1, using (2S,3S)-3-amino-2-hydroxy-N-phenethylpentanamide in step 1. MS (m/e)=684.16 [M+H⁺].

Example 50

(2S,4R)-1-(1-(4-chlorophenyl)cyclopropanecarbonyl)-4-(2-chlorophenylsulfonyl)-N—((S)-1-(2-(naphthalen-1-yl)ethylamino)-1,2-dioxopentan-3-yl)pyrrolidine-2-carboxamide

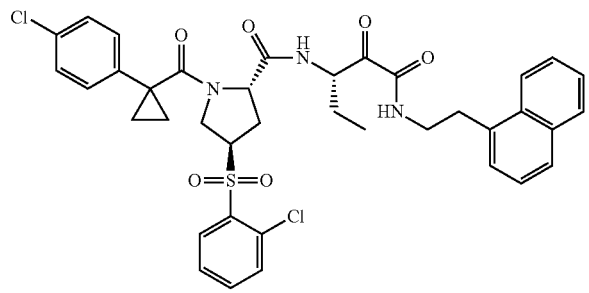 [SMILES: CC[C@H](NC(=O)[C@@H]1C[C@@H](S(=O)(=O)c2ccccc2Cl)CN1C(=O)C1(c2ccc(Cl)cc2)CC1)C(=O)C(=O)NCCc1cccc2ccccc12]

The title compound was prepared in analogy to Example 1, using (2S,3S)-3-amino-2-hydroxy-N-(2-(naphthalen-1-yl)ethyl)pentanamide in step 1. MS (m/e)=734.18 [M+H⁺].

Example 51

(2S,4R)-1-(1-(4-chlorophenyl)cyclopropanecarbonyl)-4-(2-chlorophenylsulfonyl)-N—((S)-1-(2-(naphthalen-2-yl)ethylamino)-1,2-dioxopentan-3-yl)pyrrolidine-2-carboxamide

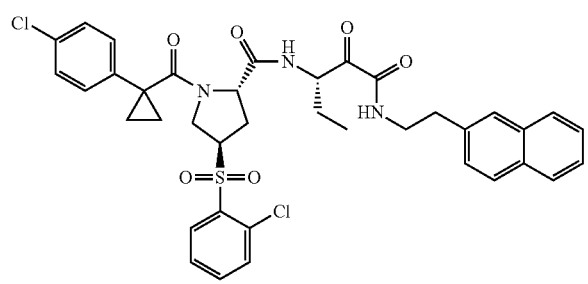 [SMILES: CC[C@H](NC(=O)[C@@H]1C[C@@H](S(=O)(=O)c2ccccc2Cl)CN1C(=O)C1(c2ccc(Cl)cc2)CC1)C(=O)C(=O)NCCc1ccc2ccccc2c1]

The title compound was prepared in analogy to Example 1, using (2S,3S)-3-amino-2-hydroxy-N-(2-(naphthalen-2-yl)ethyl)pentanamide in step 1. MS (m/e)=734.18 [M+H⁺].

Example 52

(2S,4R)-1-(1-(4-chlorophenyl)cyclopropanecarbonyl)-4-(2-chlorophenylsulfonyl)-N—((S)-1-(naphthalen-1-ylmethylamino)-1,2-dioxopentan-3-yl)pyrrolidine-2-carboxamide

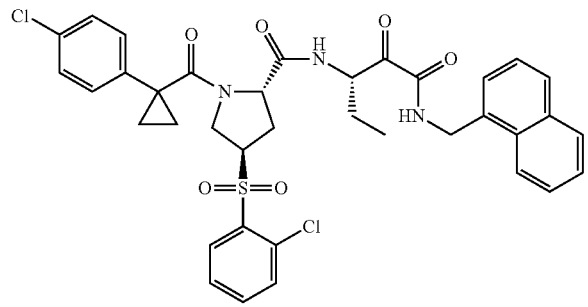 [SMILES: CC[C@H](NC(=O)[C@@H]1C[C@@H](S(=O)(=O)c2ccccc2Cl)CN1C(=O)C1(c2ccc(Cl)cc2)CC1)C(=O)C(=O)NCc1cccc2ccccc12]

The title compound was prepared in analogy to Example 1, using (2S,3S)-3-amino-2-hydroxy-N-(naphthalen-1-ylmethyl)pentanamide in step 1. MS (m/e)=720.17 [M+H⁺].

Example 53

(2S,4R)-1-(1-(4-chlorophenyl)cyclopropanecarbonyl)-4-(2-chlorophenylsulfonyl)-N—((S)-1,2-dioxo-1-(tetrahydro-2H-pyran-4-ylamino)pentan-3-yl)pyrrolidine-2-carboxamide

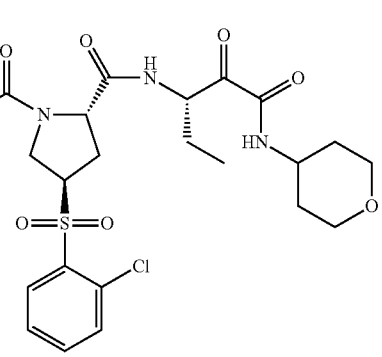

The title compound was prepared in analogy to Example 1, using (2S,4R)-4-(2-Chloro-benzenesulfonyl)-1-[1-(4-chloro-phenyl)-cyclopropanecarbonyl]-pyrrolidine-2-carboxylic acid and (S)-3-Amino-2-oxo-pentanoic acid (tetrahydro-pyran-4-yl)-am in step 1. MS (m/e)=664.16 [M+H⁺].

Example 54

(2S,4R)-1-(1-(4-chlorophenyl)cyclopropanecarbonyl)-4-(2-chlorophenylsulfonyl)-N—((S)-1-(2-methoxyethylamino)-1,2-dioxopentan-3-yl)pyrrolidine-2-carboxamide

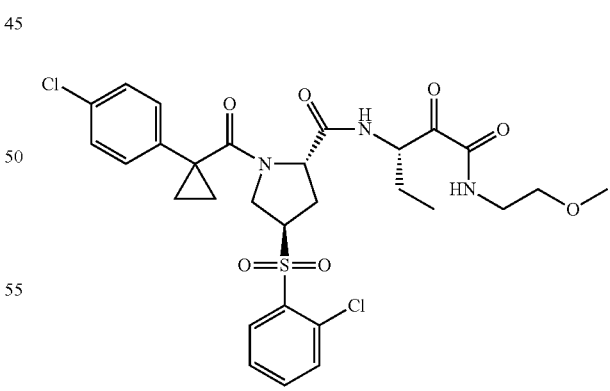

The title compound was prepared in analogy to Example 1, using (2S,4R)-4-(2-Chloro-benzenesulfonyl)-1-[1-(4-chloro-phenyl)-cyclopropanecarbonyl]-pyrrolidine-2-carboxylic acid and (S)-3-Amino-2-oxo-pentanoic acid (2-methoxy-ethyl)-a in step 1. MS (m/e)=638.15 [M+H⁺].

Example 55

(2S,4R)-1-(1-(4-chlorophenyl)cyclopropanecarbonyl)-4-(2-chlorophenylsulfonyl)-N—((S)-1-(isobutylamino)-1,2-dioxopentan-3-yl)pyrrolidine-2-carboxamide

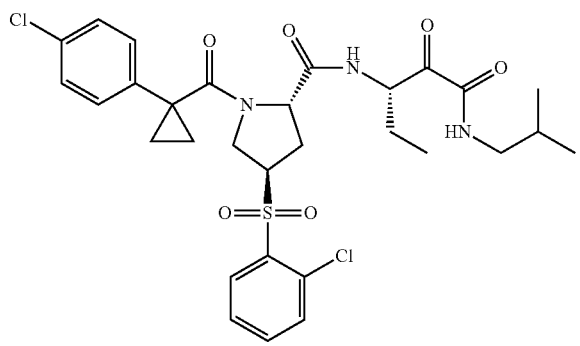 [SMILES: CC[C@H](NC(=O)[C@@H]1C[C@@H](S(=O)(=O)c2ccccc2Cl)CN1C(=O)C1(c2ccc(Cl)cc2)CC1)C(=O)C(=O)NCC(C)C]

The title compound was prepared in analogy to Example 1, using (2S,4R)-4-(2-Chloro-benzenesulfonyl)-1-[1-(4-chloro-phenyl)-cyclopropanecarbonyl]-pyrrolidine-2-carboxylic acid and (S)-3-Amino-2-oxo-pentanoic acid isobutyl-amide in step 1. MS (m/e)=636.17 [M+H$^+$].

Example 56

(2S,4R)-4-(2-chloro-4-morpholinophenylsulfonyl)-1-(1-(4-chlorophenyl)cyclopropanecarbonyl)-N—((S)-1-(cyclopropylamino)-1,2-dioxopentan-3-yl)pyrrolidine-2-carboxamide

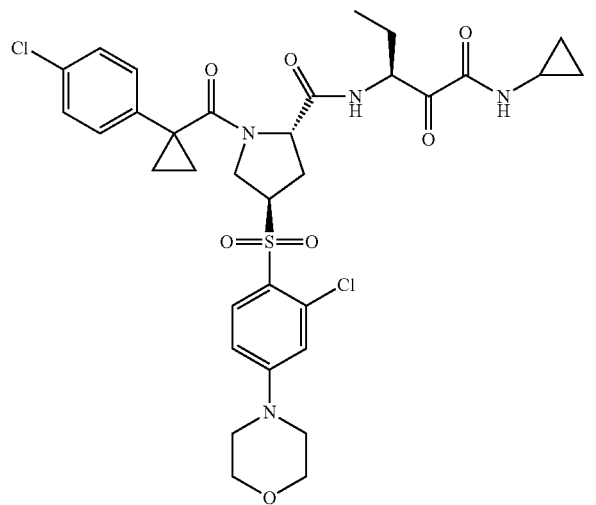 [SMILES: CC[C@H](NC(=O)[C@@H]1C[C@@H](S(=O)(=O)c2ccc(N3CCOCC3)cc2Cl)CN1C(=O)C1(c2ccc(Cl)cc2)CC1)C(=O)C(=O)NC1CC1]

The title compound was prepared in analogy to Example 1, using (2S,4R)-4-(2-Chloro-4-morpholin-4-yl-benzenesulfonyl)-1-[1-(4-chloro-phenyl)-cyclopropane carbonyl]-pyrrolidine-2-carboxylic acid and (S)-3-Amino-2-oxo-pentanoic acid cyclopropylamide in step 1. MS (m/e)=705.19 [M+H$^+$].

Example 57

(2S,4R)-4-(2-chloro-4-morpholinophenylsulfonyl)-1-(1-(4-chlorophenyl)cyclopropanecarbonyl)-N—((S)-1-(cyclopropylamino)-1,2-dioxohexan-3-yl)pyrrolidine-2-carboxamide

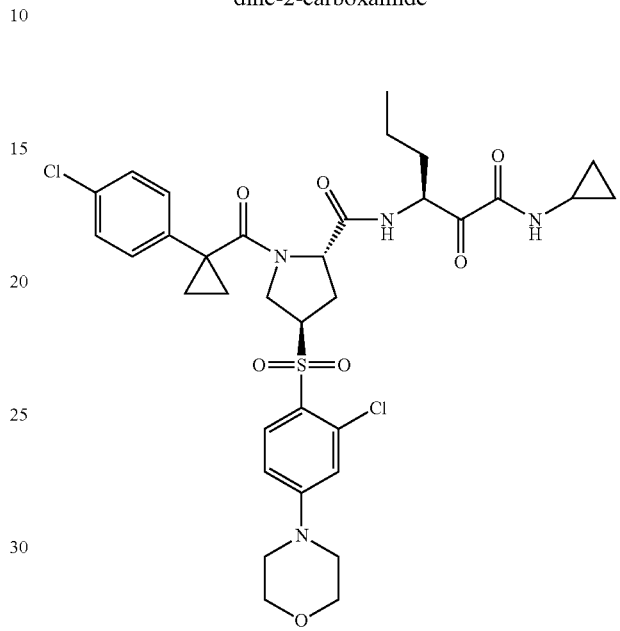

The title compound was prepared in analogy to Example 1, using (2S,4R)-4-(2-Chloro-4-morpholin-4-yl-benzenesulfonyl)-1-[1-(4-chloro-phenyl)-cyclopropanecarbonyl]-pyrrolidine-2-carboxylic acid and (S)-3-Amino-2-oxo-hexanoic acid cyclopropylamide in step 1. MS (m/e)=719.20 [M+H$^+$].

Example 58

(2S,4R)-1-(1-(5-chloro-3-fluoropyridin-2-yl)cyclopropanecarbonyl)-4-(2-chlorophenylsulfonyl)-N—((S)-1-(cyclopropylamino)-4-methyl-1,2-dioxopentan-3-yl)pyrrolidine-2-carboxamide

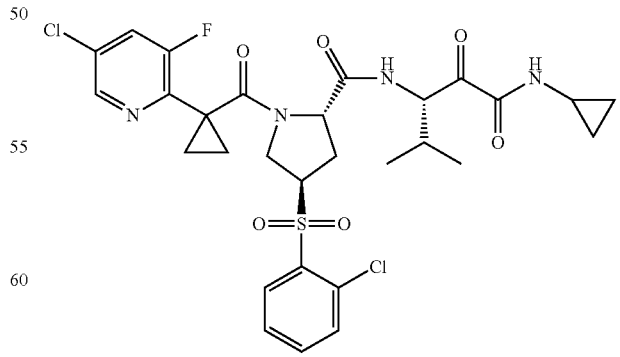

The title compound was prepared in analogy to Example 1, using (2S,4R)-4-(2-Chloro-benzenesulfonyl)-1-[1-(5-chloro-3-fluoro-pyridin-2-yl)-cyclopropanecarbonyl]-pyrrolidine-2-carboxylic acid and (S)-3-Amino-4-methyl-2-oxo-pentanoic acid cyclopropylamide in step 1. MS (m/e)=653.14 [M+H⁺].

Example 59

(2S,4R)-1-(1-(5-chloro-3-fluoropyridin-2-yl)cyclopropanecarbonyl)-4-(2-chlorophenylsulfonyl)-N—((S)-1-(cyclopropylamino)-5-methyl-1,2-dioxohexan-3-yl)pyrrolidine-2-carboxamide

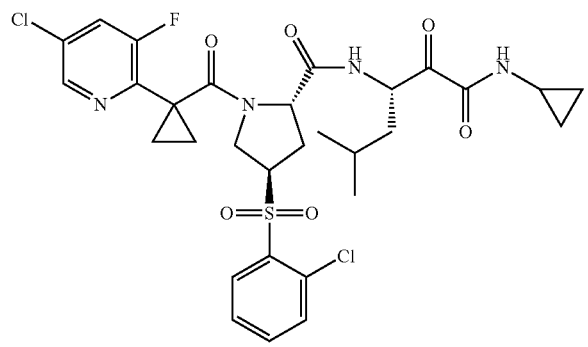 [SMILES: CC(C)C[C@H](NC(=O)[C@@H]1C[C@@H](S(=O)(=O)c2ccccc2Cl)CN1C(=O)C1(c2ncc(Cl)cc2F)CC1)C(=O)C(=O)NC1CC1]

The title compound was prepared in analogy to Example 1, using (2S,4R)-4-(2-Chloro-benzenesulfonyl)-1-[1-(5-chloro-3-fluoro-pyridin-2-yl)-cyclopropanecarbonyl]-pyrrolidine-2-carboxylic acid and (S)-3-Amino-5-methyl-2-oxohexanoic acid cyclopropylamide in step 1. MS (m/e)=667.15 [M+H⁺].

Example 60

(2S,4R)—N—((S)-1-(butylamino)-1,2-dioxopentan-3-yl)-1-(1-(5-chloro-3-fluoropyridin-2-yl)cyclopropanecarbonyl)-4-(2-chlorophenylsulfonyl)pyrrolidine-2-carboxamide

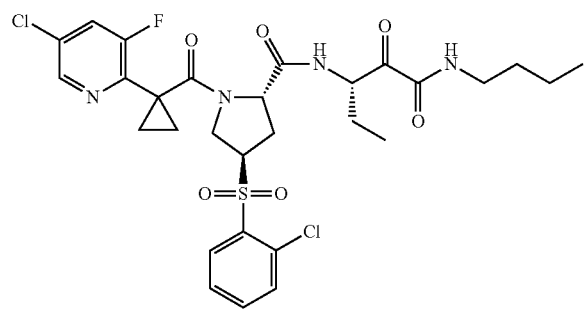 [SMILES: CCCCNC(=O)C(=O)[C@H](CC)NC(=O)[C@@H]1C[C@@H](S(=O)(=O)c2ccccc2Cl)CN1C(=O)C1(c2ncc(Cl)cc2F)CC1]

The title compound was prepared in analogy to Example 1, using (2S,4R)-4-(2-Chloro-benzenesulfonyl)-1-[1-(5-chloro-3-fluoro-pyridin-2-yl)-cyclopropanecarbonyl]-pyrrolidine-2-carboxylic acid and (S)-3-Amino-2-oxo-pentanoic acid butylamide in step 1. MS (m/e)=655.15 [M+H⁺].

Example 61

(2S,4R)—N—((S)-1-(butylamino)-1,2-dioxohexan-3-yl)-1-(1-(5-chloro-3-fluoropyridin-2-yl)cyclopropanecarbonyl)-4-(2-chlorophenylsulfonyl)pyrrolidine-2-carboxamide

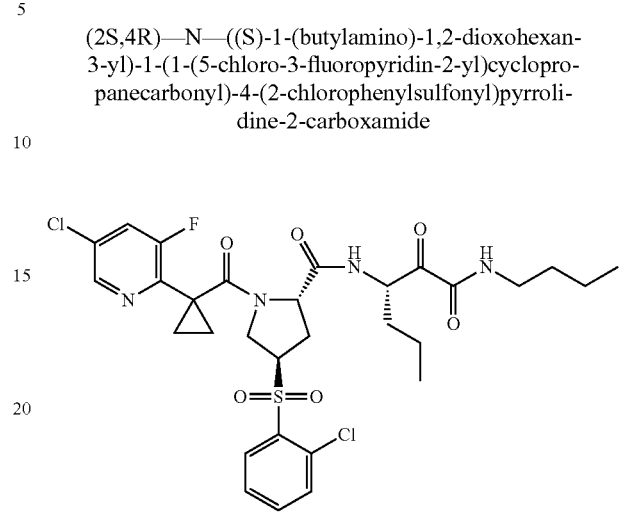

The title compound was prepared in analogy to Example 1, using (2S,4R)-4-(2-Chloro-benzenesulfonyl)-1-[1-(5-chloro-3-fluoro-pyridin-2-yl)-cyclopropanecarbonyl]-pyrrolidine-2-carboxylic acid and (S)-3-Amino-2-oxo-hexanoic acid butylamide in step 1. MS (m/e)=669.17 [M+H⁺].

Example 62

(2S,4R)—N—((S)-1-(benzylamino)-1,2-dioxohexan-3-yl)-1-(1-(5-chloro-3-fluoropyridin-2-yl)cyclopropanecarbonyl)-4-(2-chlorophenylsulfonyl)pyrrolidine-2-carboxamide

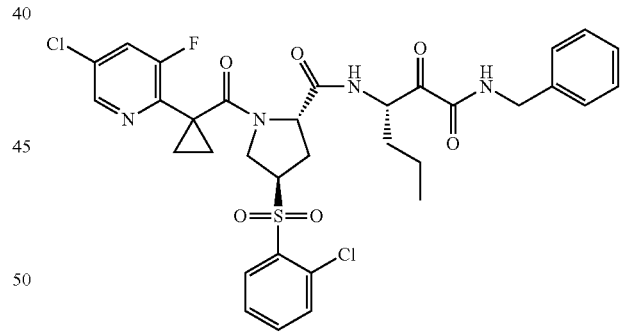

The title compound was prepared in analogy to Example 1, using (2S,4R)-4-(2-Chloro-benzenesulfonyl)-1-[1-(5-chloro-3-fluoro-pyridin-2-yl)-cyclopropanecarbonyl]-pyrrolidine-2-carboxylic acid and (S)-3-Amino-2-oxo-hexanoic acid benzylamide in step 1. MS (m/e)=703.15 [M+H⁺].

Example 63

Cathepsin Enzyme Inhibition Assay

Enzyme activity is measured by observing the increase in fluorescence intensity caused by cleavage of a peptide substrate containing a fluorophore whose emission is quenched in the intact peptide.

Assay buffer: 100 mM potassium phosphate pH 6.5, EDTA-Na 5 mM, Triton X-100 0.001%, DTT 5 mM.

Enzymes (all at 1 nM): human and mouse Cathepsin S, Cat K, Cat B, Cat L. Substrate (20 µM): Z-Val-Val-Arg-AMC, except for Cat K which uses Z-Leu-Arg-AMC (both from Bachem).
Z=Benzyloxycarbonyl.
AMC=7-Amino-4-Methyl-Coumarin.
DTT=dithiothreitol.
Final volume: 100 µL.
Excitation 360 nm, Emission 465 nm.

Enzyme is added to the substance dilutions in 96-well microtitre plates and the reaction is started with substrate. Fluorescence emission is measured over 20 minutes, during which time a linear increase is observed in the absence of inhibitor. $IC_{50}$ are calculated by standard methods. Inhibition of human Cat S, mouse Cat S, human Cat K, mouse Cat K, human Cat B, mouse Cat B, human Cat L and mouse Cat L have been measured separately. The results obtained for human Cat S, L, K and B for representative compounds of the invention are expressed in the following table in µM.

| Example | Ic50 cathepsin S | Ic50 cathepsin L | Ic50 cathepsin K | Ic50 cathepsin B |
|---|---|---|---|---|
| 1 | 0.000829 | 1.9145 | 7.9045 | 11.0695 |
| 2 | 0.001122 | 2.5925 | 9.4285 | 22.6235 |
| 3 | 0.001002 | 1.5505 | 7.4255 | 3.181 |
| 4 | 0.002979 | 0.5508 | 5.892 | 2.918 |
| 5 | 0.00183 | 25 | 25 | 105.5 |
| 6 | 0.000976 | 0.2022 | 0.1678 | 1.2985 |
| 7 | 0.003783 | 3.04 | 11.252 | 1.8525 |
| 8 | 0.000296 | 0.0043 | 0.0276 | 0.0627 |
| 9 | 0.000367 | 0.0047 | 0.0196 | 0.0433 |
| 10 | 0.002876 | 0.0554 | 0.1183 | 0.8288 |
| 11 | 0.001379 | 0.0632 | 0.3898 | 0.2911 |
| 12 | 0.000737 | 0.0212 | 0.3603 | 0.1826 |
| 13 | 0.000704 | 0.0113 | 0.0679 | 0.1422 |
| 14 | 0.000668 | 0.0104 | 0.0373 | 0.1503 |
| 15 | 0.00052 | 0.0082 | 0.0448 | 0.0985 |
| 16 | 0.000442 | 0.0059 | 0.0202 | 0.0454 |
| 17 | 0.000652 | 0.0101 | 0.0301 | 0.1068 |
| 18 | 0.0006 | 0.0084 | 0.021 | 0.0701 |
| 19 | 0.000593 | 0.0324 | 0.7583 | 0.4243 |
| 20 | 0.00056 | 0.0185 | 0.3474 | 0.2452 |
| 21 | 0.000668 | 0.0287 | 0.406 | 0.165 |
| 22 | 0.000983 | 0.0266 | 0.4054 | 0.1436 |
| 23 | 0.002978 | 0.0421 | 0.2988 | 1.229 |
| 24 | 0.00055 | 0.0108 | 0.0717 | 0.1896 |
| 25 | 0.000403 | 0.0098 | 0.0977 | 0.2514 |
| 26 | 0.010474 | 3.1045 | 25 | 25 |
| 27 | 0.017875 | 6.795 | 25 | 25 |
| 28 | 0.000328 | 0.0052 | 0.0382 | 0.0973 |
| 29 | 0.001265 | 0.0184 | 0.069 | 0.1782 |
| 30 | 0.001417 | 0.0234 | 0.1372 | 0.21 |
| 31 | 0.000827 | 0.0112 | 0.0356 | 0.0478 |
| 32 | 0.000734 | 0.0077 | 0.024 | 0.0294 |
| 33 | 0.001114 | 0.0136 | 0.0529 | 0.077 |
| 34 | 0.000787 | 0.028 | 0.4437 | 0.3994 |
| 35 | 0.001213 | 0.0098 | 0.0215 | 0.031 |
| 36 | 0.000776 | 0.0165 | 0.1554 | 0.3495 |
| 37 | 0.001024 | 0.0151 | 0.1074 | 0.2459 |
| 38 | 0.00034 | 0.0106 | 0.0533 | 0.1542 |
| 39 | 0.000558 | 0.0114 | 0.0636 | 0.1397 |
| 40 | 0.00106 | 0.0299 | 0.4062 | 0.3662 |
| 41 | 0.000568 | 0.0117 | 0.1522 | 0.1871 |
| 42 | 0.000634 | 0.0117 | 0.0287 | 0.1154 |
| 43 | 0.000508 | 0.0136 | 0.1614 | 0.1123 |
| 44 | 0.000779 | 0.0136 | 0.0918 | 0.1076 |
| 45 | 0.005426 | 0.0749 | 0.212 | 0.3352 |
| 46 | 0.005982 | 0.0671 | 0.251 | 0.2238 |
| 47 | 0.02226 | 0.2827 | 0.9976 | 1.537 |
| 48 | 0.000527 | 0.0094 | 0.035 | 0.0832 |
| 49 | 0.000901 | 0.002 | 0.0344 | 0.0302 |
| 50 | 0.002758 | 0.0086 | 0.1192 | 0.0688 |
| 51 | 0.003076 | 0.013 | 0.1594 | 0.1724 |
| 52 | 0.001959 | 0.0094 | 0.3166 | 0.3855 |
| 53 | 0.000676 | 0.0017 | 0.0393 | 0.1884 |
| 54 | 0.00063 | 0.0026 | 0.082 | 0.0854 |
| 55 | 0.000876 | 0.0026 | 0.0565 | 0.0616 |
| 56 | 0.002568 | 0.0206 | 0.0654 | 0.1011 |
| 57 | 0.003328 | 0.0249 | 0.075 | 0.0932 |
| 58 | 0.000478 | 0.0009 | 0.0491 | 0.3234 |
| 59 | 0.002608 | 0.0064 | 0.1414 | 0.5185 |
| 60 | 0.002866 | 0.0061 | 0.1436 | 0.3541 |
| 61 | 0.002934 | 0.0062 | 0.1062 | 0.1722 |
| 62 | 0.002348 | 0.006 | 0.0412 | 0.12 |

The compounds according to the invention have, an $IC_{50}$ at Cathepsin S or at Cathepsin L, or at both Cathepsin S and Cathepsin L, which is 0.00001 and 100 µM, preferably between 0.00001 and 50 µM, more preferably between 0.00001 and 20 µM. The particular compounds of the invention have an $IC_{50}$ at Cathepsin S or at Cathepsin L, or at both Cathepsin S and Cathepsin L below 0.03 µM.

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc 2 | 5 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound according to formula (I),

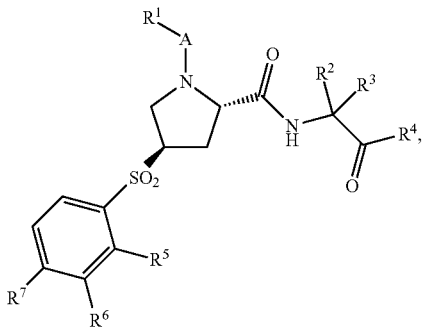

wherein
A is carbonyl or absent;
R¹ is selected from the group consisting of alkoxy, nitrophenyl, 1H-pyrazolyl substituted with alkyl and cycloalkyl, alkylcycloalkyl, haloalkylcycloalkyl, phenylcycloalkyl, halophenylcycloalkyl, pyridinylcycloalkyl and halopyridinylcycloalkyl;
R² and R³ are independently selected from the group consisting of hydrogen, alkyl and cycloalkylalkyl;
or R² and R³ together with the carbon atom to which they are attached form cycloalkyl;
R⁴ is —C(O)NR⁸R⁹ or benzooxazolyl;
R⁵, R⁶ and R⁷ are independently selected from the group consisting of hydrogen, alkyl, halogen, haloalkyl, alkoxy, haloalkoxy and morpholinyl; and
one of R⁸ and R⁹ is hydrogen or alkyl and the other one is selected from the group consisting of alkyl, alkoxyalkyl, cycloalkyl, haloalkyl, phenylalkyl, naphthylalkyl and tetrahydropyranyl;
or a pharmaceutically acceptable salt or ester thereof.

2. The compound according to claim 1, wherein R¹ is halophenylcycloalkyl or halopyridinylcycloalkyl.

3. The compound according to claim 1, wherein R¹ is selected from the group consisting of chlorophenylcyclopropyl, chlorofluorophenylcyclopropyl, bromophenylcyclopropyl, bromofluorophenylcyclopropyl and chlorofluoropyridinylcyclopropyl.

4. The compound according to claim 1, wherein R² and R³ are independently selected from hydrogen and alkyl.

5. The compound according to claim 1, wherein R² and R³ are independently selected from the group consisting of hydrogen, methyl, ethyl, propyl and butyl.

6. The compound according to claim 1, wherein R⁵, R⁶ and R⁷ are independently selected from the group consisting of halogen, haloalkyl and haloalkoxy.

7. The compound according to claim 1, wherein R⁵, R⁶ and R⁷ are independently selected from the group consisting of hydrogen, chloro, trifluoromethyl and trifluoroethoxy.

8. The compound according to claim 1, wherein R⁵ is chloro or trifluoromethyl.

9. The compound according to claim 1, wherein R⁶ is hydrogen.

10. The compound according to claim 1, wherein R⁷ is selected from the group consisting of hydrogen, chloro and trifluoroethoxy.

11. The compound according to claim 1, wherein one of R⁸ and R⁹ is hydrogen and the other one is alkyl or cycloalkyl.

12. The compound according to claim 1, wherein one of R⁸ and R⁹ is hydrogen and the other one is selected from the group consisting of ethyl, propyl, butyl and cyclopropyl.

13. The compound according to claim 1 selected from the group consisting of
(2S,4R)-tert-butyl 2-((S)-1-(cyclopropylamino)-1,2-dioxopentan-3-ylcarbamoyl)-4-(2,4-dimethylphenylsulfonyl)pyrrolidine-1-carboxylate;
(2S,4R)-tert-butyl 4-(4-chloro-2-methylphenylsulfonyl)-2-((S)-1-(cyclopropylamino)-1,2-dioxopentan-3-ylcarbamoyl)pyrrolidine-1-carboxylate;
(2S,4R)—N—((S)-1-(cyclopropylamino)-1,2-dioxopentan-3-yl)-1-(2-nitrophenyl)-4-(2-(trifluoromethyl)phenylsulfonyl)pyrrolidine-2-carboxamide;
(2S,4R)-1-(1-cyclobutyl-3-methyl-1H-pyrazol-5-yl)-N—((S)-1-(cyclopropylamino)-1,2-dioxopentan-3-yl)-4-(4-fluoro-2-(trifluoromethyl)phenylsulfonyl)pyrrolidine-2-carboxamide;
(2S,4R)-1-(2-Nitro-phenyl)-4-(2-trifluoromethyl-benzenesulfonyl)-pyrrolidine-2-carboxylic acid [(S)-1-(benzooxazole-2-carbonyl)-propyl]amide;
(2S,4R)-4-(4-bromo-2-(trifluoromethyl)phenylsulfonyl)-1-(1-cyclobutyl-3-methyl-1H-pyrazol-5-yl)-N—-((S)-1-(cyclopropylamino)-1,2-dioxopentan-3-yl)pyrrolidine-2-carboxamide;
(2S,4R)—N—((S)-1-(cyclopropylamino)-1,2-dioxopentan-3-yl)-1-(1-(trifluoromethyl)cyclopropanecarbonyl)-4-(2-(trifluoromethyl)phenylsulfonyl)pyrrolidine-2-carboxamide;
(2S,4R)-1-(1-(4-chlorophenyl)cyclopropanecarbonyl)-4-(2-chlorophenylsulfonyl)-N-((S)-1-(cyclopropylamino)-1,2-dioxopentan-3-yl)pyrrolidine-2-carboxamide;
(2S,4R)-1-(1-(4-chlorophenyl)cyclopropanecarbonyl)-4-(2-chlorophenylsulfonyl)-N—((S)-1-(cyclopropylamino)-1,2-dioxohexan-3-yl)pyrrolidine-2-carboxamide;
(2S,4R)-1-(1-(5-chloro-3-fluoropyridin-2-yl)cyclopropanecarbonyl)-4-(2-chloro-4-(2,2,2-trifluoroethoxy)phenylsulfonyl)-N—((S)-1-(cyclopropylamino)-1,2-dioxopentan-3-yl)pyrrolidine-2-carboxamide;
(2S,4R)-1-(1-(4-chlorophenyl)cyclopropanecarbonyl)-N-((S)-1-(cyclopropylamino)-1,2-dioxopentan-3-yl)-4-(4-(2,2,2-trifluoroethoxy)-2-(trifluoromethyl)phenylsulfonyl)pyrrolidine-2-carboxamide;
(2S,4R)—N—((S)-1-(benzo[d]oxazol-2-yl)-1-oxobutan-2-yl)-1-(1-(4-chlorophenyl)cyclopropanecarbonyl)-4-(2-chlorophenylsulfonyl)pyrrolidine-2-carboxamide;
(2S,4R)-1-(1-(4-chloro-2-fluorophenyl)cyclopropanecarbonyl)-4-(2-chlorophenylsulfonyl)-N—((S)-1-(cyclopropylamino)-1,2-dioxopentan-3-yl)pyrrolidine-2-carboxamide; and
(2S,4R)-1-(1-(4-bromo-2-fluorophenyl)cyclopropanecarbonyl)-4-(2-chlorophenylsulfonyl)-N—((S)-1-(cyclopropylamino)-1,2-dioxopentan-3-yl)pyrrolidine-2-carboxamide.

14. The compound according to claim 1 selected from the group consisting of
(2S,4R)-1-(1-(4-bromophenyl)cyclopropanecarbonyl)-4-(2-chlorophenylsulfonyl)-N—((S)-1-(cyclopropylamino)-1,2-dioxopentan-3-yl)pyrrolidine-2-carboxamide;
(2S,4R)-1-(1-(4-bromophenyl)cyclopropanecarbonyl)-4-(2-chlorophenylsulfonyl)-N—((S)-1-(cyclopropylamino)-1,2-dioxohexan-3-yl)pyrrolidine-2-carboxamide;

(2S,4R)-4-(2-chlorophenylsulfonyl)-N—((S)-1-(cyclopropylamino)-1,2-dioxopentan-3-yl)-1-(1-(4-iodophenyl)cyclopropanecarbonyl)pyrrolidine-2-carboxamide;

(2S,4R)-4-(2-chlorophenylsulfonyl)-N—((S)-1-(cyclopropylamino)-1,2-dioxohexan-3-yl)-1-(1-(4-iodophenyl)cyclopropanecarbonyl)pyrrolidine-2-carboxamide;

(2S,4R)-1-(1-(5-chloro-3-fluoropyridin-2-yl)cyclopropanecarbonyl)-N—((S)-1-(cyclopropylamino)-1,2-dioxopentan-3-yl)-4-(2-(trifluoromethyl)phenylsulfonyl)pyrrolidine-2-carboxamide;

(2S,4R)-1-(1-(5-chloro-3-fluoropyridin-2-yl)cyclopropanecarbonyl)-N—((S)-1-(cyclopropylamino)-1,2-dioxohexan-3-yl)-4-(2-(trifluoromethyl)phenylsulfonyl)pyrrolidine-2-carboxamide;

(2S,4R)-1-(1-(4-chlorophenyl)cyclopropanecarbonyl)-N—((S)-1-(cyclopropylamino)-1,2-dioxopentan-3-yl)-4-(2-(trifluoromethyl)phenylsulfonyl)pyrrolidine-2-carboxamide;

(2S,4R)-1-(1-(4-chlorophenyl)cyclopropanecarbonyl)-N—((S)-1-(cyclopropylamino)-1,2-dioxohexan-3-yl)-4-(2-(trifluoromethyl)phenylsulfonyl)pyrrolidine-2-carboxamide;

(2S,4R)-1-(1-(5-bromo-3-fluoropyridin-2-yl)cyclopropanecarbonyl)-4-(2-chlorophenylsulfonyl)-N—((S)-1-(cyclopropylamino)-1,2-dioxopentan-3-yl)pyrrolidine-2-carboxamide;

(2S,4R)-1-(1-(5-chloro-3-fluoropyridin-2-yl)cyclopropanecarbonyl)-4-(2-chlorophenylsulfonyl)-N—((S)-1-(cyclopropylamino)-1,2-dioxohexan-3-yl)pyrrolidine-2-carboxamide;

(2S,4R)-1-(1-(5-chloro-3-fluoropyridin-2-yl)cyclopropanecarbonyl)-4-(2-chlorophenylsulfonyl)-N—((S)-1-(cyclopropylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N-(4-(cyclopropylamino)-2-methyl-3,4-dioxobutan-2-yl)pyrrolidine-2-carboxamide;

(2S,4R)-1-(1-(4-chlorophenyl)cyclopropanecarbonyl)-4-(2-chlorophenylsulfonyl)-N-(1-(2-(cyclopropylamino)-2-oxoacetyl)cyclopropyl)pyrrolidine-2-carboxamide;

(2S,4R)-1-(1-(4-chlorophenyl)cyclopropanecarbonyl)-4-(2-chlorophenylsulfonyl)-N—((S)-1-(cyclopropylamino)-4-methyl-1,2-dioxopentan-3-yl)pyrrolidine-2-carboxamide; and (2S,4R)-1-(1-(4-chlorophenyl)cyclopropanecarbonyl)-4-(2-chlorophenylsulfonyl)-N—((S)-1-(cyclopropylamino)-5-methyl-1,2-dioxohexan-3-yl)pyrrolidine-2-carboxamide.

15. The compound according to claim 1 selected from the group consisting of (2S,4R)-4-(2-chloro-4-((S)-1,1,1-trifluoropropan-2-yloxy)phenylsulfonyl)-1-(1-(4-chlorophenyl)cyclopropanecarbonyl)-N—((S)-1-(cyclopropylamino)-1,2-dioxopentan-3-yl)pyrrolidine-2-carboxamide;

(2S,4R)-4-(2-chloro-4-((S)-1,1,1-trifluoropropan-2-yloxy)phenylsulfonyl)-1-(1-(4-chlorophenyl)cyclopropanecarbonyl)-N—((S)-1-(cyclopropylamino)-1,2-dioxohexan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(cyclopropyl(methyl)amino)-1,2-dioxohexan-3-yl)pyrrolidine-2-carboxamide;

(2S,4R)-4-(2-chloro-4-fluorophenylsulfonyl)-1-(1-(4-chlorophenyl)cyclopropanecarbonyl)-N—((S)-1-(cyclopropylamino)-1,2-dioxohexan-3-yl)pyrrolidine-2-carboxamide;

(2S,4R)-1-(1-(4-chlorophenyl)cyclopropanecarbonyl)-4-(2-chlorophenylsulfonyl)-N—((S)-1,2-dioxo-1-(phenethylamino)pentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(2-(naphthalen-1-yl)ethylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(2-(naphthalen-2-yl)ethylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(naphthalen-1-ylmethylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1,2-dioxo-1-(tetrahydro-2H-pyran-4-ylamino)pentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(2-methoxyethylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(isobutylamino)-1,2-dioxopentan-3-yl)pyrrolidine-2-carboxamide;

(2S,4R)-4-(2-chloro-4-morpholinophenylsulfonyl)-1-(1-(4-chlorophenyl)cyclopropanecarbonyl)-N—((S)-1-(cyclopropylamino)-1,2-dioxopentan-3-yl)pyrrolidine-2-carboxamide;

(2S,4R)-4-(2-chloro-4-morpholinophenylsulfonyl)-1-(1-(4-chlorophenyl)cyclopropanecarbonyl)-N—((S)-1-(cyclopropylamino)-1,2-dioxohexan-3-yl)pyrrolidine-2-carboxamide;

(2S,4R)-1-(1-(5-chloro-3-fluoropyridin-2-yl)cyclopropanecarbonyl)-4-(2-chlorophenylsulfonyl)-N—((S)-1-(cyclopropylamino)-4-methyl-1,2-dioxopentan-3-yl)pyrrolidine-2-carboxamide;

(2S,4R)-1-(1-(5-chloro-3-fluoropyridin-2-yl)cyclopropanecarbonyl)-4-(2-chlorophenylsulfonyl)-N—((S)-1-(cyclopropylamino)-5-methyl-1,2-dioxohexan-3-yl)pyrrolidine-2-carboxamide;

(2S,4R)—N—((S)-1-(butylamino)-1,2-dioxopentan-3-yl)-1-(1-(5-chloro-3-fluoropyridin-2-yl)cyclopropanecarbonyl)-4-(2-chlorophenylsulfonyl)pyrrolidine-2-carboxamide;

(2S,4R)—N—((S)-1-(butylamino)-1,2-dioxohexan-3-yl)-1-(1-(5-chloro-3-fluoropyridin-2-yl)cyclopropanecarbonyl)-4-(2-chlorophenylsulfonyl)pyrrolidine-2-carboxamide; and (2S,4R)—N—((S)-1-(benzylamino)-1,2-dioxohexan-3-yl)-1-(1-(5-chloro-3-fluoropyridin-2-yl)cyclopropanecarbonyl)-4-(2-chlorophenylsulfonyl)pyrrolidine-2-carboxamide.

16. The compound according to claim 1 selected from the group consisting of:

(2S,4R)—N—((S)-1-(butylamino)-1,2-dioxopentan-3-yl)-1-(1-(4-chlorophenyl)cyclopropanecarbonyl)-4-(2-chlorophenylsulfonyl)pyrrolidine-2-carboxamide;

(2S,4R)-1-(1-(4-(chlorophenyl)cyclopropanecarbonyl)-4-(2-chlorophenylsulfonyl)-N-((S))-4-(cyclopropylamino)-3,4-dioxobutan-2-yl)pyrrolidine-2-carboxamide;

(2S,4R)-1-(1-(4-chlorophenyl)cyclopropanecarbonyl)-N—((S)-1-(cyclopropylamino)-1-2-dioxopentan-3-yl)-4-(2,4-dichlorophenylsulfonyl)pyrrolidine-2-carboxamide;

(2S,4R)-1-(1-(4-chlorophenyl)cyclopropanecarbonyl)-4-(2-chlorophenylsulfonyl)-N—((S)-1-(isopropylamino)-1,2-dioxohexan-3-yl)pyrrolidine-2-carboxamide;

(2S,4R)-1-(1-(4-chlorophenyl)cyclopropanecarbonyl)-4-(2-chlorophenylsulfonyl)-N-((S)-1-(ethylamino)-1,2-dioxopexan-3-yl)pyrrolidine-2-carboxamide; and (2S,4R)-1-(1-(4-chlorophenyl)cyclopropanecarbonyl)-4-(2-chlorophenylsulfonyl)-N—((S)-1-(ethylamino)-1,2-dioxohexan-3-yl)pyrrolidine-2-carboxamide.

17. A pharmaceutical composition comprising the compound according to claim 1 and a therapeutically inert carrier.

18. A compound according to claim 1, wherein said compound is (2S,4R)-1-(1-(5-chloro-3-fluoropyridin-2-yl)cyclopropanecarbonyl)-4-(2-chlorophenylsulfonyl)-N—((S)-1-(cyclopropylamino)-1,2-dioxopentan-3-yl)pyrrolidine-2-carboxamide.

19. The compound according to claim 1 selected from the group consisting of (2S,4R)-1-(1-(4-chlorophenyl)cyclopropanecarbonyl)-4-(2-chlorophenylsulfonyl)-N-((S)-1-cyclohexyl-4-(cyclopropylamino)-3,4-dioxobutan-2-yl)pyrrolidine-2-carboxamide;

(2S,4R)—N—((S)-(butylamino)-1,2-dioxopentan-3-yl)-1-(1-(4-chlorophenyl)cyclopropanecarbonyl)-4-(2-chlorophenylsulfonyl)pyrrolidine-2-carboxamide;

(2S,4R)—N—((S)-1-(butylamino)-1,2-dioxohexan-3-yl)-1-(1-(4-chlorophenyl)cyclopropanecarbonyl)-4-(2-chlorophenylsulfonyl)pyrrolidine-2-carboxamide;

(2S,4R)—N—((S)-1-(benzylamino)-1,2-dioxopentan-3-yl)-1-(1-(4-chlorophenyl)cyclopropanecarbonyl)-4-(2-chlorophenylsulfonyl)pyrrolidine-2-carboxamide;

(2S,4R)-1-(4-chlorophenyl)cyclopropanecarbonyl)-4-(2-chlorophenylsulfonyl)-N—((S)-4-(cyclopropylamino)-3,4-dioxobutan-2-yl)pyrrolidine-2-carboxamide;

(2S,4R)—N—((S)-1-(benzylamino)-1,2-dioxohexan-3-yl)-1-(1-(4-chlorophenyl)cyclopropanecarbonyl)-4-(2-chlorophenylsulfonyl)pyrrolidine-2-carboxamide;

(2S,4R)-1-(1-(4-chlorophenyl)cyclopropanecarbonyl)-4-(2-chlorophenylsulfonyl)-N-((3S)-1,2-dioxo-1-(pentan-2-ylamino)pentan-3-yl)pyrrolidine-2-carboxamide;

(2S,4R)-1-(1-(4-chlorophenyl)cyclopropanecarbonyl)-4-(2-chlorophenylsulfonyl)-N-((3S)-1,2-dioxo-1-(pentan-2-ylamino)hexan-3-yl)pyrrolidine-2-carboxamide;

(2S,4R)-1-(1-(4-chlorophenyl)cyclopropanecarbonyl)-N—((S)-1-(cyclopropylamino)-1,2-dioxopentan-3-yl)-4-(2,4-dichlorophenylsulfonyl)pyrrolidine-2-carboxamide;

(2S,4R)-4-(2-chloro-4-fluorophenylsulfonyl)-1-(1-(4-chlorophenyl)cyclopropanecarbonyl)-N—((S)-1-(cyclopropylamino)-1,2-dioxopentan-3-yl)pyrrolidine-2-carboxamide;

(2S,4R)-1-(1-(4-chlorophenyl)cyclopropanecarbonyl)-4-(2-chlorophenylsulfonyl)-N—((S)-1,2-dioxo-1-(2,2,2-trifluoroethylamino)hexan-3-yl)pyrrolidine-2-carboxamide;

(2S,4R)-1-(1-(4-chlorophenyl)cyclopropanecarbonyl)-4-(2-chlorophenylsulfonyl)-N—((S)-1-(isopropylamino)-1,2-dioxohexan-3-yl)pyrrolidine-2-carboxamide;

(2S,4R)-1-(1-(4-chlorophenyl)cyclopropanecarbonyl)-N—((S)-1-(cyclopropylamino)-1,2-dioxohexan-3-yl)-4-(2,4-dichlorophenylsulfonyl)pyrrolidine-2-carboxamide;

(2S,4R)-1-(1-(4-chlorophenyl)cyclopropanecarbonyl)-4-(2-chlorophenylsulfonyl)-N—((S)-1-(ethylamino)-1,2-dioxopentan-3-yl)pyrrolidine-2-carboxamide; and (2S,4R)-1-(1-(4-chlorophenyl)cyclopropanecarbonyl)-4-(2-chlorophenylsulfonyl)-N—((S)-1-(ethylamino)-1,2-dioxohexan-3-yl)pyrrolidine-2-carboxamide.

\* \* \* \* \*